US009216950B2

(12) United States Patent
Shiau et al.

(10) Patent No.: US 9,216,950 B2
(45) Date of Patent: Dec. 22, 2015

(54) AGONISTS OF SRC HOMOLOGY-2 CONTAINING PROTEIN TYROSINE PHOSPHATASE-1 AND TREATMENT METHODS USING THE SAME

(75) Inventors: Chung-Wai Shiau, Taipei (TW); Kuen-Feng Chen, Taipei (TW)

(73) Assignees: NATIONAL TAIWAN UNIVERSITY, Taipei (TW); NATIONAL YANG-MING UNIVERSITY, Taipei (TW); DCB-USA LLC, Wilmington, DE (US)

( * ) Notice: Subject to any disclaimer, the term of this patent is extended or adjusted under 35 U.S.C. 154(b) by 0 days.

(21) Appl. No.: 14/235,620

(22) PCT Filed: Aug. 3, 2012

(86) PCT No.: PCT/US2012/049446
§ 371 (c)(1),
(2), (4) Date: Jan. 28, 2014

(87) PCT Pub. No.: WO2013/020014
PCT Pub. Date: Feb. 7, 2013

(65) Prior Publication Data
US 2014/0200239 A1 Jul. 17, 2014

Related U.S. Application Data

(60) Provisional application No. 61/514,555, filed on Aug. 3, 2011.

(51) Int. Cl.
| | | |
|---|---|---|
| C07C 255/57 | (2006.01) |
| C07D 471/04 | (2006.01) |
| C07D 215/233 | (2006.01) |
| C07C 275/40 | (2006.01) |
| C07C 311/29 | (2006.01) |
| C07C 255/59 | (2006.01) |
| C07D 213/68 | (2006.01) |
| C07D 213/81 | (2006.01) |
| C07D 215/40 | (2006.01) |
| C07C 255/54 | (2006.01) |
| C07C 275/36 | (2006.01) |
| C07C 311/21 | (2006.01) |

(52) U.S. Cl.
CPC ............ *C07C 255/57* (2013.01); *C07C 255/54* (2013.01); *C07C 255/59* (2013.01); *C07C 275/36* (2013.01); *C07C 275/40* (2013.01); *C07C 311/21* (2013.01); *C07C 311/29* (2013.01); *C07D 213/68* (2013.01); *C07D 213/81* (2013.01); *C07D 215/233* (2013.01); *C07D 215/40* (2013.01); *C07D 471/04* (2013.01)

(58) Field of Classification Search
None
See application file for complete search history.

(56) References Cited

U.S. PATENT DOCUMENTS 5,145,843 A * 9/1992 Arnold et al. .................... 514/63
7,528,255 B2 * 5/2009 Riedl et al. .................... 546/290

FOREIGN PATENT DOCUMENTS

WO 2012112570 8/2012

OTHER PUBLICATIONS

Gouley et al., 69 J. Am. Chem. Soc. 303-6 (1947) (CAS Abstract).*
Nam et al., 19(13) Bioorg. & Med. Chem. Letts. 3517-3520 (CAS Abstract).*
Chen et al. Sorafenib derivatives include apoptosis through inhibition of STAT3 independent of Raf., European Journal of Medicinal Chemistry, Apr. 2011, vol. 46, pp. 2845-2851; p. 2846, Fig 1, compound 1.
Chen et al. Blockade of STAT3 activation by sorafenib derivatives through enhancing SHP-1 phosphatase activity, European Journal of Medicinal Chemistry, Jul. 2012, vol. 55, pp. 220-227; entire document.

* cited by examiner

*Primary Examiner* — Timothy R Rozof
(74) *Attorney, Agent, or Firm* — WPAT, P.C.; Anthony King

(57) ABSTRACT

The present invention provides new compounds of formula I, II or III, which have Src homology-2 containing protein tyrosine phosphatase-1 (SHP-1) agonist activity. Also provided are treatment methods using the compounds of formula I, II or III.

15 Claims, 38 Drawing Sheets

Formula I

Formula II

Formula III

General synthetic procedure for Formula I, II, III: a, $K_2CO_3$, DMF; b, pyridine, THF; c. $Et_3N$, dioxane

A

B

A

B

C

A

(D)

(E)

(F)

(C)

(D)

(B)

(C)

AGONISTS OF SRC HOMOLOGY-2 CONTAINING PROTEIN TYROSINE PHOSPHATASE-1 AND TREATMENT METHODS USING THE SAME

FIELD OF THE INVENTION

The present invention relates to new compounds having Src homology-2 containing protein tyrosine phosphatase-1 (SHP-1) agonist activity and treatment methods using the same.

BACKGROUND OF THE INVENTION

SHP-1, a protein-tyrosine phosphatase with two Src homology 2 (SH2) domains, is a regulator of various intracellular signaling molecules, such as signal transducer and activator of transcription 3 (STAT3), KIT, CD22, CD5, CD72, SHPS-1, TIMP (metalloproteinases), CDK2, p27, SRC, ZAP70, IL-10, NF-κB, Lck, 3BP2, Lyn and cyclin D1. STAT3 is a transcription factor which regulates cell growth and survival by modulating the expression of target genes. It acts as an oncogene which is constitutively active in many cancers including liver, lung, head and neck, prostate, and breast as well as myeloma and leukemia. A key regulator of STAT3 activity is SHP-1. From a mechanistic perspective, SHP-1 exhibits protein phosphatase activity which reduces the level of Phospho-STAT3 (P-STAT) and subsequently blocks the dimerization of P-STAT3. Therefore, expression of target genes, such as cyclin D1 and survivin transcribed by STAT3, is significantly reduced. In addition, studies of SHP-1 protein and SHP-1 mRNA showed that expression level of SHP-1 was low in most cancer cells; and genetic increase in SHP-1 in cancer cells resulted in the suppression of cell growth, suggesting that the SHP-1 gene acts as a tumor suppressor. From the drug discovery point of view, development of a small molecule which can reduce P-STAT3 and increase SHP-1 level is a promising direction for cancer therapy. SHP-1 also play an important role in bone remodeling, a process of bone-forming osteoblasts and bone-resorbing osteoclasts. Loss function of SHP-1 results in osteoclast and eventually leads to osteoporosis. Therefore, enhancement of SHP-1 activity might be a direction for osteoporosis patient. In addition, increase of SHP-1 is benefit for the macrophages of multiple sclerosis patients

BRIEF SUMMARY OF THE INVENTION

The present invention is based on the unexpected finding that newly designed compounds act as SHP-1 agonists and have the ability to reduce P-STAT3, and are useful for treating certain diseases, such as cancer. Specifically, the compounds of the invention do not block activity of kinases, such as Raf-1 and VEGFR2.

Particularly, in one aspect, the invention provides a compound of formula I

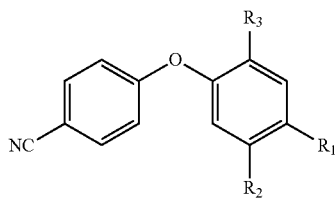

I wherein $R_1$, $R_2$, and $R_3$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted heteroaryl, optionally substituted aralkyl, optionally substituted heteroarakyl, $—(C)_m NHC(X)NH(C)_n R_a—$, $—(C)_p NHC(X)R_b—$, $—(C)_q NHS(O)_2 R_c$, $—(C)_r(X) NHR_d—$, or $—(C)_s NH(C)_t R_e$;

wherein $R_a$, $R_b$, $R_c$, $R_d$ and $R_e$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl;

X=O or S; and m, n, p, q, r, s, t=0, 1, or 2.

In another aspect, the present invention provides a compound of Formula II, including a compound of Formula II(a), a compound of Formula II(b), or a compound of Formula II(c),

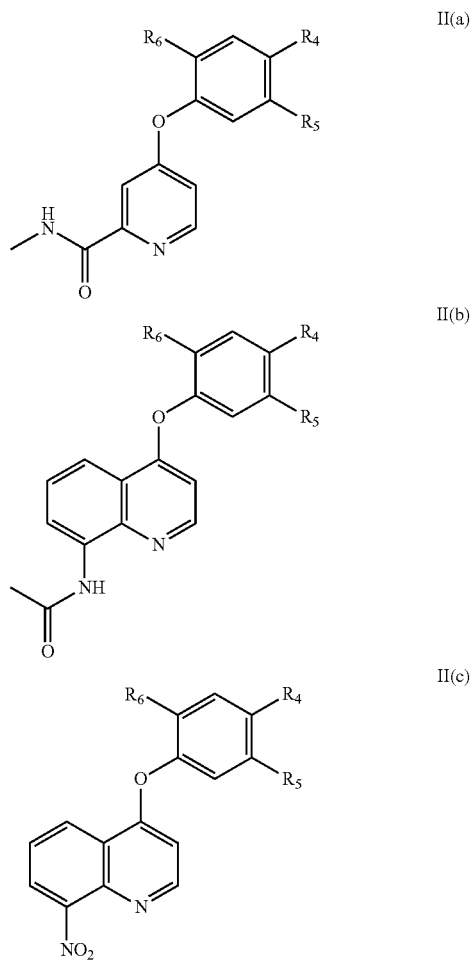

wherein $R_4$, $R_5$ and $R_6$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl, $—(C)_m NHC(X)NH(C)_n$ $R_a—$, —(C)$_p$NHC(X)R$_b$—, —(C)$_q$NHS(O)$_2$R$_c$, —(C)$_r$(X)NHR$_d$—, or —(C)$_n$NH(C)R$_e$;

wherein R$_a$, R$_b$, R$_c$, R$_d$ and R$_e$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl;

X=O or S; and m, n, p, q, r, s, t=0, 1, or 2.

In a further aspect, the invention provides a compound of Formula III

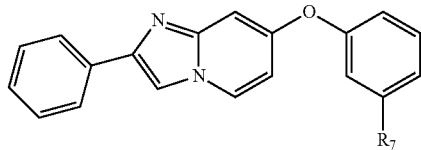

III wherein R$_7$ is hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl, —(C)$_m$NHC(X)NH(C)$_n$ R$_a$—, —(C)$_p$NHC(X)R$_b$—, —(C)$_q$NHS(O)$_2$R$_c$, —(C)$_r$(X)NHR$_d$—, or —(C)$_s$NH(C)R$_e$;

wherein R$_a$, R$_b$, R$_c$, R$_d$ and R$_e$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl;

X=O or S; and m, n, p, q, r, s, t=0, 1, or 2.

The present invention also provides a pharmaceutical composition comprising one or more of the above-described compounds. The pharmaceutical composition of the invention may be used for increasing expression levels or biological activity of SHP-1 in a cell, or treating a disease or condition characterized by decreased expression levels or biological activity of Src homology-2 containing protein tyrosine phosphatase-1, which includes but is not limited to cancer (e.g. hepatocellular carcinoma, leukemia, lung cancer, breast cancer, renal cancer, thyroid cancer, head and neck cancer, sclerosis and osteoporosis. Also within the scope of this invention is the use of any of the above-described compounds for increasing expression levels or biological activity of SHP-1 in a cell, or treating a disease or condition characterized by decreased expression levels or biological activity of SHP-1 as described herein and for the manufacture of a medicament for treating the same.

Also provided is a method for increasing SHP-1 expression levels or biological activity in a cell, comprising contacting the cell with an effective amount of a compound or a pharmaceutical composition as described herein.

Further provided is a method for treating a disease or condition characterized by decreased expression levels or biological activity of SHP-1 in a subject in need thereof, comprising administering to the subject an effective amount of a compound or a pharmaceutical composition as described herein.

The various embodiments of the present invention are described in details below. Other characteristics of the present invention will be clearly presented by the following detailed descriptions and drawings about the various embodiments and claims.

It is believed that a person of ordinary knowledge in the art where the present invention belongs can utilize the present invention to its broadest scope based on the descriptions herein with no need of further illustration. Therefore, the following descriptions should be understood as of demonstrative purpose instead of limitative in any way to the scope of the present invention.

BRIEF DESCRIPTION OF THE SEVERAL VIEWS OF THE DRAWINGS

For the purpose of illustrating the invention, there are shown in the drawings embodiments which are presently preferred. It should be understood, however, that the invention is not limited to the preferred embodiments shown.

In the drawings.

DETAILED DESCRIPTION OF THE INVENTION

Figure 1:
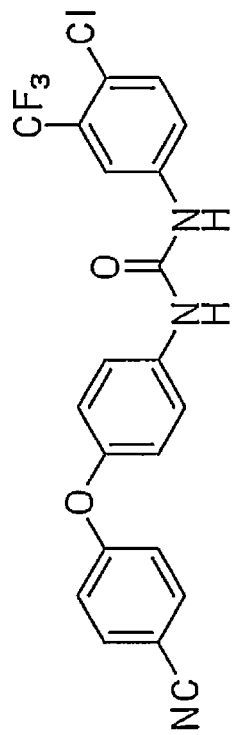
FIG. 1 shows the chemical structure of sorafenib and compound SC-1.
Figure 1:
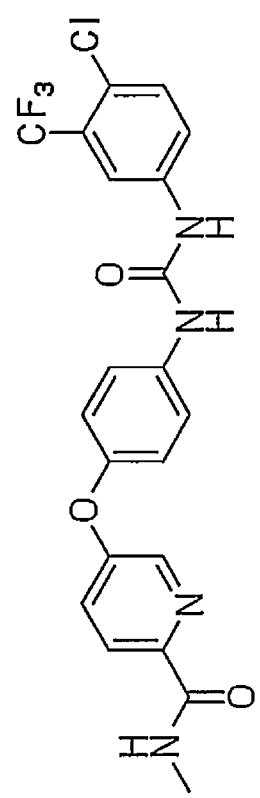

Unless defined otherwise, all technical and scientific terms used herein have the same meaning as commonly understood by a person skilled in the art to which this invention belongs. All publications mentioned herein are incorporated herein by reference to disclose and describe the methods and/or materials in connection with which the publications are cited.

As used herein, the singular forms "a", "an", and "the" include plural referents unless the context clearly dictates otherwise. Thus, for example, reference to "a sample" includes a plurality of such samples and equivalents thereof known to those skilled in the art.

Sorafenib (BAY43-9006, Nexavar) has been used clinically for renal carcinoma and hepatocellular carcinoma (HCC). It is known as a multiple kinase inhibitor that represses the activity of Raf-1 and other tyrosine kinases such as VEGFR2, VEGFR3, Flt-3, PDGFR, and FGFR-1.

In this invention, we studied the relationship between the structure of sorafenib and its bioactivity and modified the structure of sorafenib. We accordingly developed a number of sorafenib derivatives without the ability to block the kinase activity, and unexpectedly found that these compounds exhibit good therapeutic effects in certain diseases, such as cancer, at least comparable with that of sorafenib. According to the invention, the newly designed compounds of the invention act as SHP-1 agonists and are useful for treating a disease or condition characterized by decreased expression levels or biological activity of SHP-1, such as cancer (e.g. hepatocellular carcinoma, hepatocellular carcinoma, leukemia, lung cancer, breast cancer, renal cancer, thyroid cancer, head and neck cancer, sclerosis and osteoporosis). The compounds of the invention also provide a new theraptic option for patients with the resistance to kinase inhibitors. These tumors generate kinase mutation after treatment and constitutely in the phosphorylated active form, even in the present of a kinase inhibitor. Therefore, upregulation of a tumor suppressor, especially SHP-1, to repress the active mutation form of kinases is a promising direction for chemo-resistance patients. In other words, the compounds of the invention, acting through a new targeting mechanism (kinase independent), provide alternative therapeutic options that may be helpful in the treatment of cancer with resistance to conventional medical therapeutics.

In one aspect, the present invention provides a compound of formula I

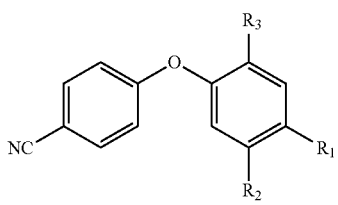

I wherein $R_1$, $R_2$, and $R_3$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl, —(C)$_m$NHC(X)NH(C)$_n$R$_a$—, —(C)$_p$NHC(X)R$_b$—, —(C)$_q$NHS(O)$_2$R$_c$, —(C)$_r$(X)NHR$_d$—, or —(C)$_s$NH(C)$_t$R$_e$;

wherein $R_a$, $R_b$, $R_c$, $R_d$ and $R_e$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl;

X=O or S; and m, n, p, q, r, s, t=0, 1, or 2.

In one embodiment, the compound of formula I includes those in which $R_1$, $R_2$, and $R_3$ are independently hydrogen, optionally substituted lower alkyl, —(C)$_m$NHC(X)NH(C)$_n$R$_a$—, —(C)$_p$NHC(X)R$_b$—, —(C)$_q$NHS(O)$_2$R$_c$, or —(C)NH(C)$_t$R$_e$.

In another embodiment, the compound of formula I includes those in which $R_a$, $R_b$, $R_c$, $R_d$ and $R_e$ are independently phenyl or naphthyl, optionally substituted with 1 to 3 groups selected from the group consisting of halo, optionally substituted lower alkyl (such as halo-substituted lower alkyl, e.g. trifluoromethyl), optionally substituted alkoxyl (e.g. such as halo-substituted lower alkoxyl, e.g. trifluoromethyl) and optionally substituted aryloxy (e.g. cyano-substituted phenoxy).

In certain examples, the compound of formula I is one of the compounds SC-1, SC-48, SC-49, SC-54, SC-55, SC-56, SC-58, SC-43, SC-44, SC-45, SC-50, SC-51, SC-52, SC-59, SC-60 and SC-40 as listed in table 1.

TABLE 1

| Cpd | $R_1$ | $R_2$ | $R_3$ |
|---|---|---|---|
| SC-1 | (substituent with CF$_3$, Cl, urea linkage) | H | H |
| SC-48 | (substituent with two OMe groups, urea linkage) | H | H |
| SC-49 | (substituent with CF$_3$, Cl, urea linkage with CH$_2$) | H | H |

TABLE 1-continued
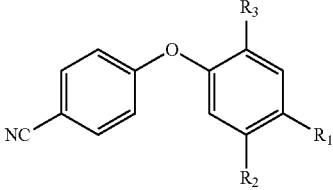
| Cpd | R₁ | R₂ | R₃ |
|---|---|---|---|
| SC-54 | 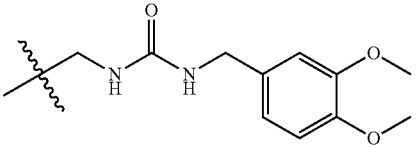 [SMILES: *CNC(=O)NCc1ccc(OC)c(OC)c1] | H | H |
| SC-55 | 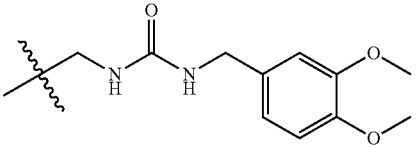 [SMILES: *CNC(=O)NCc1ccc(OC)c(OC)c1] | H | H |
| SC-56 | 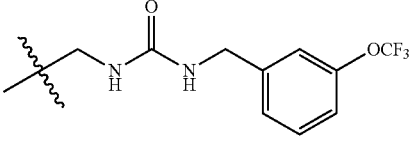 [SMILES: *CNC(=O)NCc1cccc(OC(F)(F)F)c1] | H | H |
| SC-58 | 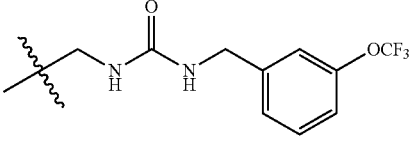 [SMILES: *CNC(=O)NCc1cccc(OC(F)(F)F)c1] | H | H |
| SC-43 | H | 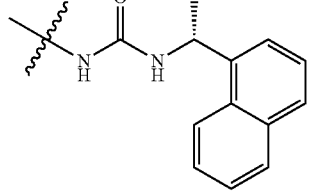 | H |
| SC-44 | H | 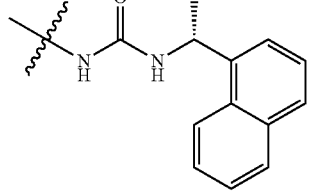 | H |
| SC-45 | H | 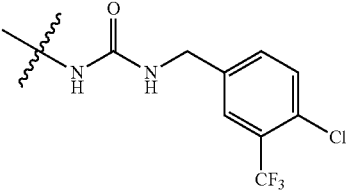 [SMILES: *NC(=O)NCc1ccc(Cl)c(C(F)(F)F)c1] | H |

TABLE 1-continued
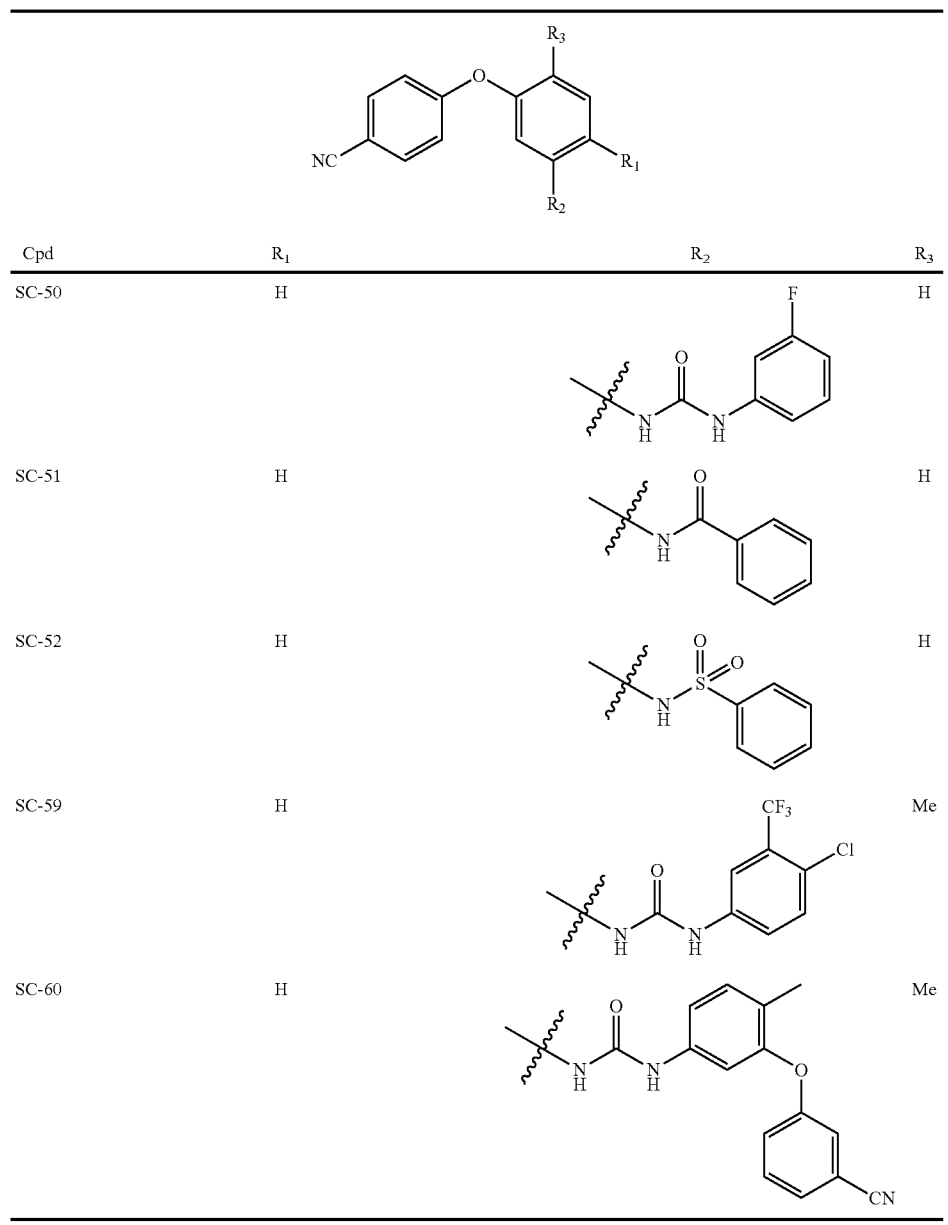
In another aspect, the present invention provides a compound of Formula II, including a compound of formula II(a), a compound of formula II(b) or a compound of formula II(c),
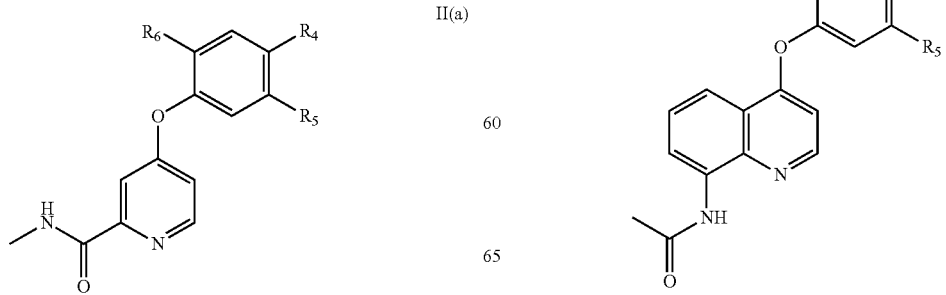

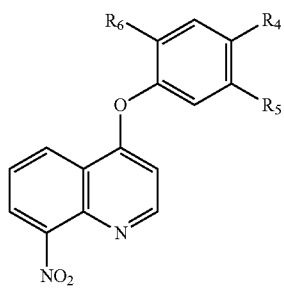

II(c)

wherein $R_4$, $R_5$ and $R_6$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl, —(C)$_m$NHC(X)NH(C)$_n$ R$_a$—, —(C)$_p$NHC(X)R$_b$—, —(C)$_q$NHS(O)$_2$R$_c$, —(C)$_r$(X)NHR$_d$—, or —(C)$_n$NH(C)$_s$R$_e$;

wherein R$_a$, R$_b$, R$_c$, R$_d$ and R$_e$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl;

X=O or S; and m, n, p, q, r, s, t=0, 1, or 2.

In one embodiment, the compound of formula II includes those in which $R_4$, $R_5$ and $R_6$ are independently hydrogen, optionally substituted lower alkyl, —(C)$_m$NHC(X)NH(C)$_n$ R$_a$—, —(C)$_p$NHC(X)R$_b$—, —(C)$_q$NHS(O)$_2$R$_c$, or —(C)NH (C)$_r$R$_e$.

In another embodiment, the compound of formula II includes those in which R$_a$, R$_b$, R$_c$, R$_d$ and R$_e$ are independently phenyl or naphthyl, optionally substituted with 1 to 3 groups selected from the group consisting of halo, optionally substituted lower alkyl (such as halo-substituted lower alkyl, e.g. trifluoromethyl), optionally substituted alkoxyl (e.g. such as halo-substituted lower alkoxyl, e.g. trifluoromethyl) and optionally substituted aryloxy (e.g. cyano-substituted phenoxy).

In certain examples, the compound of formula II is one of the compounds SC-31, SC-32, SC-33, SC-34 and SC-35, as listed in Table 2.

TABLE 2

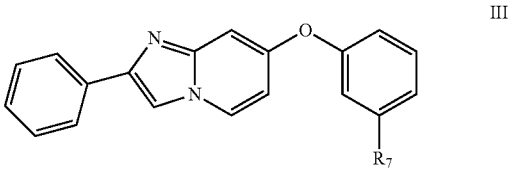

| Cpd | R$_4$ | R$_5$ | R$_6$ |
|---|---|---|---|
| SC-31 | H | ![urea-3-fluorophenyl] | H |
| SC-32 | H | ![NH-CH2-3-OCF3-phenyl] | H |
| SC-33 | H | ![sulfonamide-3-CF3-phenyl] | H |
| SC-34 | H | ![benzamide] | H |
| SC-35 | H | ![phenylsulfonamide] | H |

In a further aspect, the present invention provides a compound of Formula III

III wherein R$_7$ is hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl, —(C)$_m$NHC(X)NH(C)$_n$ R$_a$—, —(C)$_p$NHC(X)R$_b$—, —(C)$_q$NHS(O)$_2$R$_c$, —(C)$_r$(X)NHR$_d$—, or —(C)$_s$NH(C)$_r$R$_e$;
wherein R$_a$, R$_b$, R$_c$, R$_d$ and R$_e$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl;

X=O or S; and m, n, p, q, r, s, t=0, 1, or 2.

In one embodiment, the compound of formula III includes those in which wherein $R_7$ is independently hydrogen, optionally substituted lower alkyl, —(C)$_m$NHC(X)NH(C)$_n$R$_a$—, —(C)$_p$NHC(X)R$_b$—, —(C)$_q$NHS(O)$_2$R$_c$, or —(C)$_s$NH(C)$_t$R$_e$.

In another embodiment, the compound of formula III includes those in which $R_a$, $R_b$, $R_c$, $R_d$ and $R_e$ are independently phenyl or naphthyl, optionally substituted with 1 to 3 groups selected from the group consisting of halo, optionally substituted lower alkyl (such as halo-substituted lower alkyl, e.g. trifluoromethyl), optionally substituted alkoxyl (e.g. such as halo-substituted lower alkoxyl, e.g. trifluoromethyl) and optionally substituted aryloxy (e.g. cyano-substituted phenoxy).

In certain examples, the compound of formula III is one of the compounds SC-36, SC-37 and SC-38, as listed in Table 3.

TABLE 3

| Cpd | $R_7$ |
|---|---|
| SC-36 | HN-CH$_2$-C$_6$H$_4$-OCF$_3$ (3-position) |
| SC-37 | HN-SO$_2$-C$_6$H$_4$-CF$_3$ (3-position) |
| SC-38 | HN-SO$_2$-C$_6$H$_5$ |

The term "halo" or "halogen" alone or in combination means all halogens, such as fluorine (F), chlorine (Cl), bromine (Br) or iodine (I).

The term "hydroxyl" refers to the group —OH.

The terms "thio" and "mercapto" are used interchangeably and refer to the group-SH."

The term "alkyl" alone or in combination refers to an alkane-derived radical containing, unless otherwise stated, 1-20 carbon atoms ($C_1$-$C_{20}$), preferably 1-15 carbon atoms ($C_1$-$C_{15}$), more preferably 1-10 carbon atoms ($C_1$-$C_{10}$). It is a straight chain alkyl, branched alkyl or cycloalkyl, preferably, straight or branched alkyl groups containing from 1-15, more preferably 1 to 8 even more preferably 1-6, yet more preferably 1-4 and most preferably 1-2, carbon atoms, such as methyl, ethyl, propyl, isopropyl, butyl, t-butyl and the like. The term "lower alkyl" is used herein to describe the straight chain alkyl groups as described above. Preferably, cycloalkyl groups are monocyclic, bicyclic or tricyclic ring systems of 3-8, more preferably 3-6, ring members per ring, such as cyclipropyl, cyclopentyl, cyclohexyl, adamantly and the like. Alkyl also includes a straight chain or branched aljyl group that contains or is interrupted by a cycloalkyl portion. The straight chain or branched alkyl group is attached at any available point to produce a stable compound. Examples of this include, but are not limited to, 4-(isopropyl)-cyclohexylene or 2-methyl-cyclopropylpentyl. A substituted with 1 to 3 groups or substituents of halo, hydroxyl, alkoxy, alkythio, alkylsulfinyl, alkylsylfinyl, acyloxy, aryloxy, heteroaryloxy, amine optionally mono- or disubstituted with alkyl, aryl or heteroaryl groups, amidino, urea optionally substituted with alkyl, aryl, heteroaryl or heterocyclyl groups, aminosulfinyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

The term "alkenyl" alone or in combination means a straight, branched, or cyclic hydrocarbon containing 2-20, preferably 2-17, more preferably 2-10, even more preferably 2-8, most preferably 2-4, carbon atoms and at least one, preferably 1-3, more preferably 1-2, most preferably one, carbon to carbon double bind. In the case of a cycloalkenyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopronyl, butenyl, cyclohexenyl, cyclohexenylalkyl and the like. A substituted alkenyl is the straight chain alkenyl, branched alkenyl or cycloalkenyl groups defined previously, independently substituted with 1 to 3 groups or substituents of halo, hydroxyl, aryloxy, alkylthio, alkylsulfinyl, alkylsulfonyl, independently substituted with alkyl, aryl or heteroaryl groups, amidino, urea optionally substituted with alkyl, aryl, heteroaryl or heterocycloyl groups, aminosulfonyl optionally N-mono- or N,N-di-substituted with alkyl, aryl or heteroaryl groups, alkylsulfonylamino, alkylcarbonylamino, arylcarbinylamino, aryloxycarbonyl, heteroaryloxycarbonyl, or the like attached at any available point to produce a stable compound.

The term "alkynyl" alone or in combination means a straight, branched, or cyclic hydrocarbon containing 2-20, preferably 2-17, more preferably 2-10, even more preferably 2-8, most preferably 2-4, carbon atoms and at least one, preferably 1-3, more preferably 1-2, most preferably one, carbon to carbon triple bond. Examples of alkynyl groups include ethynyl, propynyl, isopropynyl, butynyl, and the like. A substituted alkynyl is the straight chain alkynyl, branched alkynyl groups defined previously, independently substituted with 1 to 3 groups or substituents of halo, hydroxyl, aryloxy, alkylthio, alkylsulfinyl, alkylsulfonyl, independently substituted with alkyl, aryl or heteroaryl groups, amidino, urea optionally substituted with alkyl, aryl, heteroaryl or heterocycloyl groups, aminosulfonyl optionally N-mono- or N,N-di-substituted with alkyl, aryl or heteroaryl groups, alkylsulfonylamino, alkylcarbonylamino, arylcarbinylamino, aryloxycarbonyl, heteroaryloxycarbonyl, or the like attached at any available point to produce a stable compound.

The term "alkyl alkenyl' refers to a group-R—CR'=CR"R'", where R is lower alkyl, or substituted lower alkyl, R', R", R'" may independently be hydrogen, halogen, lower, alkyl, substituted lower alkyl, acyl, aryl, substituted aryl, hetaryl, or substituted hetaryl as defined below.

The term "alkyl alkynyl' refers to a group-R—CCR', where R is lower alkyl, or substituted lower alkyl, R' is hydrogen, halogen, lower, alkyl, substituted lower alkyl, acyl, aryl, substituted aryl, hetaryl, or substituted hetaryl as defined below.

The term "alkoxy" denotes the group —OR, where R is lower alkyl, substituted lower alkyl, acyl, aryl, substituted aryl, arakyl, substituted arakyl, heteroalkyl, heteroarylalkyl, cycloalkyl, substituted cycloalkyl, cycloheteroalkyl, or substituted cycloheteroalkyl as definded.

The term "alkylthio" or "thioalkoxy" denotes the group- SR, $S(O)_{n=1-2}$—R, where R is lower alkyl, substituted lower alkyl, acyl, aryl, substituted aryl, arakyl, or substituted arakyl as defined herein.

The term "acyl" denotes groups-C(O)R, where R is hydrogen, lower alkyl, substituted lower alkyl, aryl, substituted aryl, and the like as defined herein.

The term "aryloxy' denotes groups-OAr, where Ar is an aryl, substituted aryl, heteroaryl, or substituted heteroaryl group as defined herein.

The term "amido" denoteds the group-C(O)NRR', where R and R' may independently by hydrogen, lower alkyl, substituted lower alkyl, aryl, substituted aryl, and the like as defined herein.

The term "carboxyl" denoteds the group-C(O)OR, where R is hydrogen, lower alkyl, substituted lower alkyl, aryl, substituted aryl, and the like as defined herein.

The term "aryl" alone or in combination means phenyl or napnthyl optionally carbocyclic fused with a cycloalkyl of preferably 5-7, more preferably 5-6, ring members and/or optionally substituted with 1 to 3 groups or substituents of halo, hydroxyl, aryloxy, alkylthio, alkylsulfinyl, alkylsulfonyl, independently substituted with alkyl, aryl or heteroaryl groups, amidino, urea optionally substituted with alkyl, aryl, heteroaryl or heterocycloyl groups, aminosulfonyl optionally N-mono- or N,N-di-substituted with alkyl, aryl or heteroaryl groups, alkylsulfonylamino, alkylcarbonylamino, arylcarbinylamino, aryloxycarbonyl, heteroaryloxycarbonyl, or the like.

The term "heterocycle" refers to a saturated, unsaturated, or aromatic carbocyclic group having a single ring (e.g., morpholino, pyridyl or furyl) or multiple condensed rings (e.g., naphthpyridyl, quinoxaryl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthioi, acetylene, amino, amido, carboxyl, hydroxyl, aryl, aryloxy, heterocycle, hetaryl, substituted hetaryl, nitro, cyano, thiol, sulfamino and the like.

The term "heteroaryl" alone or in combinations means a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group O, S, and N, and optionally substituted with 1 to 3 groups or substituents of halo, hydroxyl, alkoxy, alkythio, alkylsulfinyl, alkylsylfinyl, acyloxy, aryloxy, heteroaryloxy, amine optionally mono- or disubstituted with alkyl, aryl or heteroaryl groups, amidino, urea optionally substituted with alkyl, aryl, heteroaryl or heterocyclyl groups, aminosulfinyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intend to include oxidized S or N, such as sulfinyl, sulfonyl and N-oxide of a tertiary ring nitrogen. A carbon or nitrogen atom is the point of attachement of the heteroaryl ring structure such that a stable aromatic ring is retained. Examples of heteroaryl groups are pyridinyl, pyridazinyl, pyrazinyl, quinazolinyl, purinyl, indonyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl and the like. A substituted heteroaryl contains a substituent attached an available carbon or nitrogen to produce a stable compound.

The term "heterocyclyl" alone or in combination means a non-aromatic cyclialkyl group having from 5 to 10 atoms in which from 1 to 3 carbon atoms in the ring are replaced by heteroatoms of O, S, N, and are optionally benzo fused or fused heteroaryl of 5-6 ring members and/or are optionally substituted as in the case of cycloalkyl. Heterocyclyl is also intended to include oxidized S or N, such as sulfinyl, sulfonyl and N-oxide of a tertiary ring nitrogen. The point of attachment is at a carbon or nitrogen atom. Example of heterocyclyl group are tetrahydrofuranyl, dihydropyridinyl, piperifinyl, pyrrolidinyl, piperazinyl, dihydrobenzofuryl, dihydroindolyl, and the like. A substituted heterocyclyl contains a substituent nitrogen attached at an available carbon or nitrogen to produce a stable compound.

The term "substituted heteroaryl" refers to a heterocycle optionally mono or poly substituted with one or more functional groups, e.g., halogen, lower alkyl, lower alkoxy, alkylthio acetylene, amino, amido, carboxyl, hydroxyl, aryl, aryloxy, heterocycle, substituted heterocycle, hetaryl, substituted hetaryl, nitro, cyano, thiol, sulfamido and the like.

The term "arakyl" refers to the group-R—Ar where Ar is an aryl group and R is lower alkyl or substituted lower alkyl group. Aryl groups can optionally be unsubstituted or substituted with, e.g., halogen, lower alkyl, lower alkoxy, alkylthio acetylene, amino, amido, carboxyl, hydroxyl, aryl, aryloxy, heterocycle, substituted heterocycle, hetaryl, substituted hetaryl, nitro, cyano, thiol, sulfamido and the like.

The term "heteroalkyl" refers to the group —R-Het where Het is a heterocycle group and R is a lower alkyl group. Heteroalkyl groups can optionally be unsubstituted or substituted with halogen, lower alkyl, lower alkoxy, alkylthio acetylene, amino, amido, carboxyl, hydroxyl, aryl, aryloxy, heterocycle, substituted heterocycle, hetaryl, substituted hetaryl, nitro, cyano, thiol, sulfamido and the like.

The term "heteroarylalkyl" refers to the group —R-Het AR where HetAr is an heteroaryl group and R is a lower alkyl group. Heteroarylalkyl groups can optionally be unsubstituted or substituted with halogen, lower alkyl, lower alkoxy, alkylthio acetylene, amino, amido, carboxyl, hydroxyl, aryl, aryloxy, heterocycle, substituted heterocycle, hetaryl, substituted hetaryl, nitro, cyano, thiol, sulfamido and the like.

The term "cycloalkyl" refers to a divalent cyclic or polycyclic alkyl group containing 3 to 15 carbon atoms.

The term "substituted cycloalkyl" refers to a cycloalkyl group comprising one or more substituents with, e.g., halogen, lower alkyl, lower alkoxy, alkylthio acetylene, amino, amido, carboxyl, hydroxyl, aryl, aryloxy, heterocycle, substituted heterocycle, hetaryl, substituted hetaryl, nitro, cyano, thiol, sulfamido and the like.

The term "cycloheteroalkyl" refers to a cycloalkyl group wherein one or more of the ring carbon atoms is replaced with a heteroatom (e.g., N, O, S, or P).

The term "substituted cycloheteroalkyl" refers to a cycloheteroalkyl group as herein defined which contains one or more substituents, such as halogen, lower alkyl, lower alkoxy, alkylthio acetylene, amino, amido, carboxyl, hydroxyl, aryl, aryloxy, heterocycle, substituted heterocycle, hetaryl, substituted hetaryl, nitro, cyano, thiol, sulfamido and the like.

The term "alkyl cycloalkyl" denoted the group-R'-cycloalkyl where cycloalkyl is a cycloalkyl group and R is a lower alkyl or substituted lower alkyl. Cycloalkyl groups can optionally be unsubstituted or substituted with e.g., halogen, lower alkyl, lower alkoxy, alkylthio acetylene, amino, amido, carboxyl, hydroxyl, aryl, aryloxy, heterocycle, substituted heterocycle, hetaryl, substituted hetaryl, nitro, cyano, thiol, sulfamido and the like.

The term "alkyl cycloheteroalkyl" denoted the group-R'-cycloheteroalkyl where R is a lower alkyl or substituted lower alkyl. Cycloheteroalkyl groups can optionally be unsubstituted or substituted with e.g., halogen, lower alkyl, lower alkoxy, alkylthio acetylene, amino, amido, carboxyl, hydroxyl, aryl, aryloxy, heterocycle, substituted heterocycle, hetaryl, substituted hetaryl, nitro, cyano, thiol, sulfamido and the like.

The compounds of the invention can be prepared by conventional chemical procedure such as those described in advances organic chemistry written by Francis Carey and Richard Sundberg and review journal "Account of Chemical research."

Particularly, the procedure shown in the general scheme as below exemplifies synthesis of certain compounds of the invention.

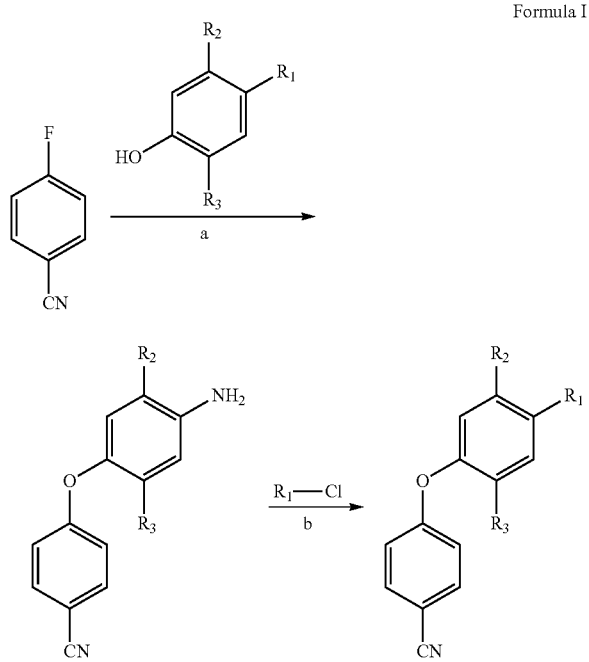

General synthetic procedure for Formula I, II, III: a, K$_2$CO$_3$, DMF; b, pyridine, THF; c. Et$_3$N, dioxane The compounds of the invention thus synthesized can be further purified by chromatography or crystallization or any other prior method known in the art.

The present invention also provides a pharmaceutical composition comprising one or more of the above-described compounds and a pharmaceutically acceptable carrier. The pharmaceutical composition of the invention may be used for increasing expression levels or biological activity of SHP-1 in a cell, or treating a disease or condition characterized by decreased expression levels or biological activity of SHP-1. Also within the scope of this invention is the use of any of the above-described compounds for increasing expression levels or biological activity of SHP-1 in a cell, or treating a disease or condition characterized by decreased expression levels or biological activity of SHP-1 as described herein and for the manufacture of a medicament for treating the same.

The present invention also provides a method for increasing SHP-1 expression levels or biological activity in a cell, comprising contacting the cell with an effective amount of a compound or a pharmaceutical composition as described herein. Further provided is a method for treating a disease or condition characterized by decreased expression levels or biological activity of SHP-1 in a subject in need thereof, comprising administering to the subject an effective amount of a compound or a pharmaceutical composition as described herein.

The term "treating" or "treatment" includes prophylaxis of the specific disorder or condition, or alleviation of the symptoms associated with a specific disorder or condition and/or preventing or eliminating said symptoms.

The compounds of the present invention can be used for the treatment of diseases or conditions characterized by decreased expression levels or biological activity of SHP-1. A compound of the invention can be administered to a human patient by itself or in pharmaceutical compositions where it is mixed with suitable carriers or excipients at doses to treat or ameliorate various conditions characterized by decreased expression levels or biological activity of SHP-1. Increased or decreased expression levels or biological activity of a factor (e.g. SHP-1) can be readily detected by the gene product of the factor such as a protein or RNA, in a sample from a subject (e.g. from blood or biopsy tissue) and assaying it in vitro for RNA levels, structure and/or activity of the expressed proteins and the like, using detection methods known in the art such as enzyme-linked immunosorbent assay (ELISA), Western blotting and Northern blotting. Particular examples of the diseases or conditions characterized by decreased expression levels or biological activity of SHP-1 according to the invention include, but are not limited to, cancer (e.g. hepatocellular carcinoma, leukemia, lung cancer, breast cancer, renal cancer, and osteoporosis.

A "subject" is particularly a mammal, such as a human, but can also be a companion animal (e.g., dogs, cats, and the like), farm animals (e.g., cows, sheep, pigs, horses, and the like) or laboratory animals (e.g., rats, mice, guinea pigs, and the like) in need of the treatment as described herein.

"An effective amount" as used herein refers to the amount of an active agent required to confer therapeutic effects on a subject, either alone or in combination with one or more other active agents. Effective amounts vary, as recognized by those skilled in the art, depending on route of administration, excipient usage, and co-usage with other active agents.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation.

The pharmaceutical compositions of the present invention may be manufactured in a manner known in the art, e.g., by means of conventional mixing, dissolving, emulsifying, encapsulating, entrapping, or lyophilizing processes. Pharmaceutical compositions for use in accordance with the present invention thus may be formulated in conventional manner using one or more physiologically acceptable carriers comprising excipients and/or auxiliaries that facilitate processing of the active compounds into preparations, which can be used pharmaceutically. As used herein, "acceptable" means that the carrier must be compatible with the active ingredient of the composition (and preferably, capable of stabilizing the active ingredient) and not deleterious to the subject to be treated. Proper formulation is dependent upon the route of administration chosen.

In particular, for injection, the compounds of the invention may be formulated in, for example, physiologically compatible buffers, such as Hank's solution, Ringer's solution, or physiological saline buffer. For oral administration, the compounds of the invention may be formulated by combining the active compounds with pharmaceutically acceptable carriers known in this art, such as lactose, sucrose, mannitol, sorbitol, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP), to enable the compounds of the invention to be formulated as tablets, pills, dragees, capsules, liquids, gels, syrups, slurries, suspensions and the like. For administration by inhalation, the compounds of the invention can be formulated in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas.

Without further elaboration, it is believed that the above description has adequately enabled the present invention. The following specific example is, therefore, to be construed as merely illustrative, and not limitative of the remainder of the disclosure in any way whatsoever. All of the publications, including patents, cited herein are hereby incorporated by reference in their entireties.

Example 1

Chemical Synthesis 1.1 Materials

Proton nuclear magnetic resonance ('H-NMR) spectra were recorded on Bruker DPX300 (400 MHz) instruments. Chemical shifts are reported as ☐☐values (ppm) downfield from internal deuterated Chloroform of the indicated organic solution. Peak multiplicities are expressed as follows: s, singlet; d, doublet; t, triplet; q, quartet; dd, doublet of doublet; ddd, doublet of doublet of doublets; dt, doublet of triplet; brs, broad singlet; m, multiplet. Coupling constants (J values) are given in hertz (Hz). Reaction progress was determined by thin layer chromatography (TLC) analysis on silica gel 60 F254 plate (Merck). Chromatographic purification was carried on silica gel columns 60 (0.063-0.200 mm or 0.040-0.063 mm, Merck), basic silica gel. Commercial reagents and solvents were used without additional purification. Abbreviations are used as follows: $CDCl_3$, deuterated chloroform; DMSO-d6, dimethyl sulfoxide-d6; EtOAc, ethyl acetate; DMF, N,N-dimethylformamide; MeOH, methanol; THF, tetrahydrofuran; EtOH, ethanol; DMSO, dimethyl sulfoxide; NMP, N-methylpyrrolidone. High resolution mass spectra were recorded on a FINNIGAN MAT 95S mass spectrometer.

1.2 Methods

Figure 2:
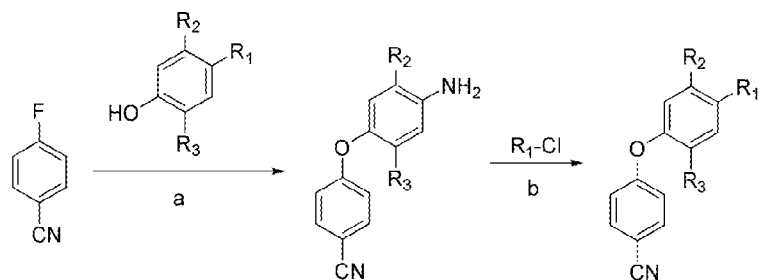
FIG. 2 shows the general synthetic procedure for formulae I, II and III of the invention.
Figure 2:
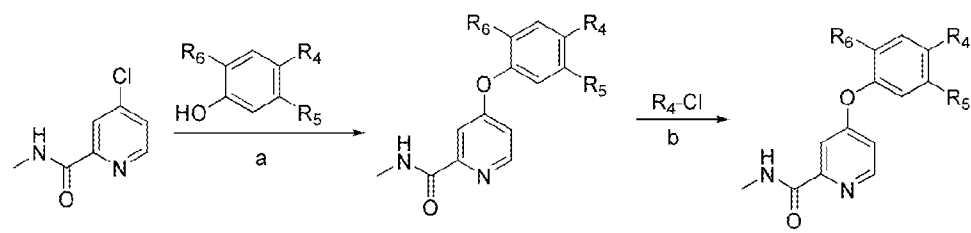
Figure 2:
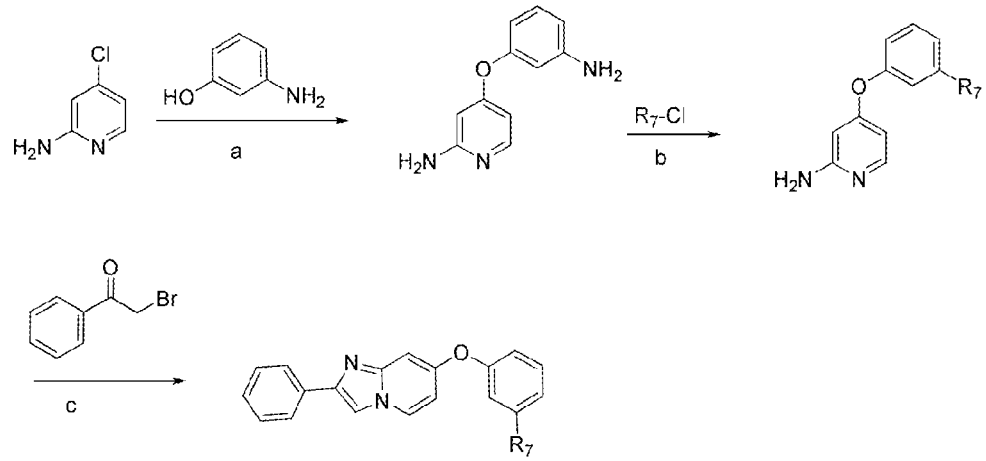

The structural design of the compounds of the invention is described below. First, to address the relationship between Raf kinase repression and downregulation of P-STAT3 by sorafenib, we used a chemical approach to reduce the hydrogen bonding interaction between the amide group of sorafenib with Raf by replacing amido group by a phenylcyano group (compound 1, FIG. 1). We also modified SC-1 based on functional groups which contain different size, hydrogen donor, hydrogen acceptor, hydrophobic and hydrophilic ability to generate a series of compounds SC-48, SC-49, SC-54, SC-55, SC-56, SC-58, SC-43, SC-44, SC-45, SC-50, SC-51, SC-52, SC-59, SC-60 and SC-40. In addition, we replaced the urea functional group in the sorafenib backbone with various amide and sulfonamide yielding compounds 2-11. Further, we replaced the pyridine ring with quinoline and used it as a platform to carry out structural modification, generating a series of compounds 12-19 and 20-25. These SC-1 derivatives were synthesized according to a general procedure described above in formula II FIG. 2. Moreover, we extend the length of compound by adding one phenyl ring to explore the structure activity relationship with different functional group 36-38.

1.2.1 Synthesis Procedures for Compound 1 (Formula I)

To a 50 mL THF solution of triphosgen (0.30 g, 1.0 mmol), 4-chloro-3-(trifluoromethyl)aniline (0.21 g, 1.1 mmol) and 2 equivalent of triethyl amine were added. The mixture was heated to 50° C. for 30 min After the temperature was back to room temperature, 4-(4-aminophenoxy)benzonitrile in the 10 mL THF solution was added to the mixture and heated to 50° C. for another 30 min. The mixture was evaporated, diluted with water and extracted with EtOAc. The extract was washed with brine, dried over anhydrous magnesium sulfate, and concentrated under reduced pressure to give 1. (0.34 g, 80%)

1.2.1.1.

1-(4-Chloro-3-(trifluoromethyl)phenyl)-3-(4-(4-cyanophenoxy)phenyl)urea (1)

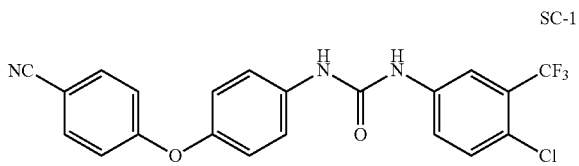 [SMILES: N#Cc1ccc(Oc2ccc(NC(=O)Nc3ccc(Cl)c(C(F)(F)F)c3)cc2)cc1]

SC-1

$^1$H NMR (400 MHz, CDCl$_3$): δ 9.17 (s, 1H), 8.94 (s, 1H), 8.10 (s, 1H), 7.81 (d, 2H, J=6.8), 7.63-7.59 (m, 2H), 7.54 (d, 2H, J=7.2 Hz), 7.10 (d, 2H, J=6.8 Hz), 7.05 (d, 2H, J=7.2 Hz); $^{13}$C NMR (100 MHz, methanol-d$_4$): δ 163.7, 163.6, 154.8, 151.4, 151.2, 140.1, 137.7, 137.4, 135.3, 132.9, 129.7, 129.4, 129.1, 128.8, 128.3, 125.6, 125.5, 125.4, 124.2, 122.9, 122.4, 122.3, 122.1, 120.2, 119.7, 118.8, 118.7, 118.6, 118.6, 106.5, 106.4; HRMS calculated for C$_{21}$H$_{13}$ClF$_3$N$_3$O$_2$ (M+H): 431.0648. Found: 431.0656.

1.2.1.2.

1-(3-(4-cyanophenoxy)phenyl)-3-(4-chloro-3-(trifluoromethyl)phenyl)urea (43)

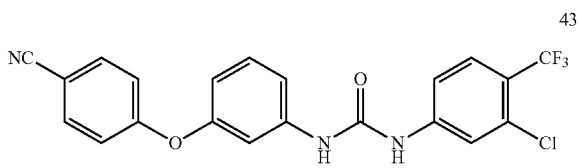 [SMILES: N#Cc1ccc(Oc2cccc(NC(=O)Nc3ccc(C(F)(F)F)c(Cl)c3)c2)cc1]

43

$^1$H NMR (400 MHz, DMSO): δ 9.17 (s, 1H), 9.03 (s, 1H), 8.04 (d, J=2.4 Hz, 1H), 7.83 (d, J=8.8 Hz, 2H), 7.64-7.55 (m, 2H), 7.41-7.32 (m, 2H), 7.23 (d, J=7.2 Hz, 1H), 7.11 (d, J=8.0 Hz, 2H), 6.75 (dd, J=8.0 Hz, 2.4 Hz, 1H); HRMS calculated for C$_{21}$H$_{12}$N$_3$O$_2$F$_3$Cl [M–H]$^-$: 430.0570. Found: 430.0576.

1.2.1.3.

4-(3-(3-(trifluoromethyl)benzen-sulfonylamino)phenoxy)benzonitrile (44)

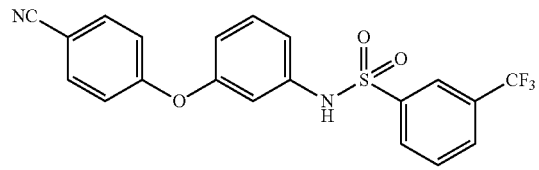

44

$^1$H NMR (400 MHz, CDCl$_3$): δ 8.00 (s, 1H), 7.96 (d, J=8.0 Hz, 1H), 7.81 (d, J=8.0 Hz, 1H), 7.65-7.54 (m, 3H), 7.26 (t, J=8.0 Hz, 1H), 7.08 (s, 1H), 7.05-6.97 (m, 1H), 6.94-6.86 (m, 3H), 6.84 (t, J=2.0 Hz, 1H), 6.81 (dd, J=8.4 Hz, 2.0 Hz, 1H); HRMS calculated for C$_{20}$H$_{12}$N$_2$O$_3$F$_3$S [M–H]$^-$: 417.0521. Found: 417.0518.

1.2.1.4.

4-(3-(3-(trifluoromethoxy)benzylamino)phenoxy)benzonitrile (45)

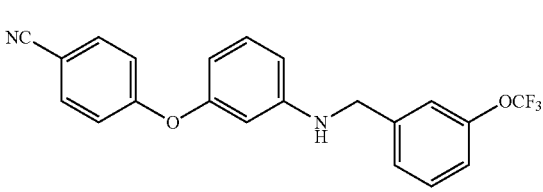

45

$^1$H NMR (400 MHz, CDCl$_3$): δ 7.61 (d, J=8.8 Hz, 2H), 7.43 (t, J=8.0 Hz, 1H), 7.33 (d, J=8.4 Hz, 1H), 7.29-7.16 (m, 3H), 7.04 (d, J=8.8 Hz, 2H), 6.55 (dd, J=8.0 Hz, 2.4 Hz, 1H), 6.46 (dd, J=8.0 Hz, 2.0 Hz, 1H), 6.34 (t, J=2.4 Hz, 1H), 4.41 (s, 2H); HRMS calculated for C$_{21}$H$_{16}$N$_2$O$_2$F$_3$ [M+H]$^+$: 385.1164. Found: 385.1157.

1.2.1.5.

1-(4-(4-cyanophenoxy)phenyl)-3-(3,4-dimethoxybenzyl)urea (48)

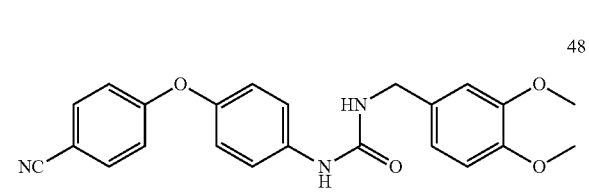 [SMILES: COc1ccc(CNC(=O)Nc2ccc(Oc3ccc(C#N)cc3)cc2)cc1OC]

48

$^1$H NMR (400 MHz, CDCl3): δ 7.56 (d, J=6.8 Hz, 2H), 7.34 (d, J=8.8 Hz, 2H), 6.98-6.94 (m, 4H), 6.88-6.75 (m, 4H), 6.56 (brs, 1H), 4.36 (s, 2H), 3.84 (s, 6H); HRMS calculated for $C_{23}H_{20}N_3O_4$ [M−H]⁻: 402.1454. Found: 402.1462.

1.2.1.6.

1-(4-chloro-3-(trifluoromethyl)phenyl)-3-(4-(4-cyanophenoxy)benzyl)urea (49)

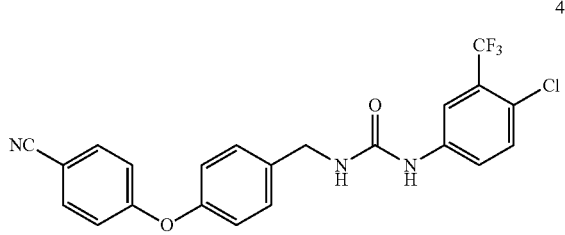

¹H NMR (400 MHz, CDCl₃): δ 7.76 Hz (s, 1H), 7.51-7.39 (m, 3H), 7.29 (dd, J=8.8 Hz, 2.4 Hz, 1H), 7.13 (d, J=8.4 Hz, 3H), 6.83 (dd, J=8.8 Hz, 4.8 Hz, 4H), 5.93 (t, J=6.0 Hz, 1H), 4.24 (d, J=6.0 Hz, 2H); HRMS calculated for $C_{22}H_{14}N_3O_2F_3Cl$ [M−H]⁻: 444.0727. Found: 444.0732.

1.2.1.7.

1-(3-(4-cyanophenoxy)phenyl)-3-(3-fluorophenyl)urea (50)

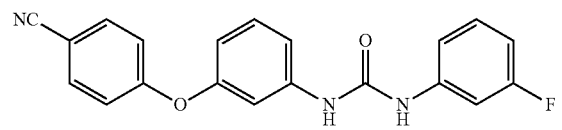

¹H NMR (400 MHz, MeOD): δ 7.66 (d, J=9.2 Hz, 2H), 7.60 (s, 1H), 7.41-7.34 (m, 2H), 7.22 (q, J=8.0 Hz, 1H), 7.18 (dd, J=8.0 Hz, 2.0 Hz, 1H), 7.10-7.02 (m, 3H), 6.71 (dd, J=8.8 Hz, 2.4 Hz, 2H); HRMS calculated for $C_{20}H_{13}N_3O_2$ [M−H]⁻: 346.0992. Found: 346.0999.

1.2.1.8.

N-(3-(4-cyanophenoxy)phenyl)benzamide (51)

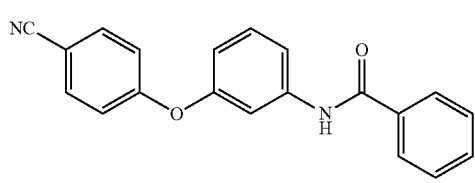

¹H NMR (400 MHz, CDCl₃): δ 8.82 (s, 1H), 7.75 (d, J=7.6 Hz, 2H), 7.53 (s, 1H), 7.46-7.35 (m, 4H), 7.28 (t, J=8.0 Hz, 2H), 7.22 (t, J=8.0 Hz, 1H), 6.90 (d, J=8.8 Hz, 2H), 6.72 (dd, J=8.0 Hz, 2.0 Hz, 1H); HRMS calculated for $C_{20}H_{13}N_2O_2$ [M−H]⁻: 313.0977. Found: 313.0971.

1.2.1.9.

N-(3-(4-cyanophenoxy)phenyl)benzenesulfonamide (52)

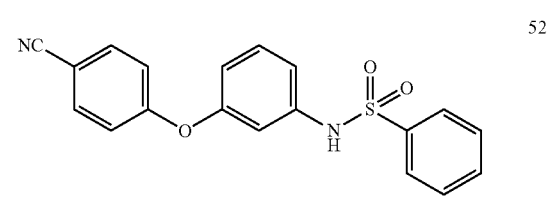 [SMILES: N#Cc1ccc(Oc2cccc(NS(=O)(=O)c3ccccc3)c2)cc1]

¹H NMR (400 MHz, CDCl₃): δ 7.79 (d, J=8.4 Hz, 2H), 7.53 (t, J=4.4 Hz, 3H), 7.42 (t, J=8.0 Hz, 2H), 7.20 (t, J=8.0 Hz, 1H), 6.93 (dd, J=8.0 Hz, 2.0 Hz, 1H), 6.86-6.83 (m, 3H), 6.73 (dd, J=8.0 Hz, 2.0 Hz, 1H); HRMS calculated for $C_{19}H_{13}N_2O_3S$ [M−H]⁻: 349.0647. Found: 2349.0643.

1.2.1.10.

1-(4-(4-cyanophenoxy)benzyl)-3-(3,4-dimethoxybenzyl)urea (54)

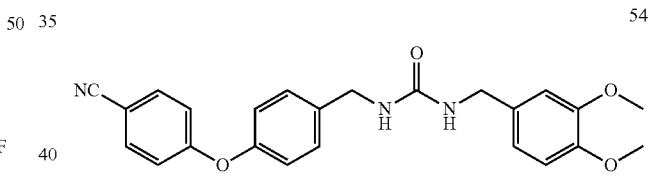

¹H NMR (400 MHz, DMSO): δ 7.81 (d, J=9.2 Hz, 2H), 7.33 (d, J=8.4 Hz, 2H), 7.06 (dd, J=15.6 Hz, 9.2 Hz, 4H), 6.86 (d, J=9.2 Hz, 2H), 6.76 (dd, J=8.0 Hz, 2.0 Hz, 1H), 6.45 (t, J=6.0 Hz, 1H), 6.38 (t, J=6.0 Hz, 1H), 4.23 (d, J=5.2 Hz, 2H), 4.14 (d, J=5.2 Hz, 2H), 3.69 (s, 6H); HRMS calculated for $C_{24}H_{24}N_3O_4$ [M+H]⁺: 418.1767. Found: 418.1773.

1.2.1.11.

1-(4-(4-cyanophenoxy)benzyl)-3-(3-(trifluoromethoxy)benzyl)urea (55)

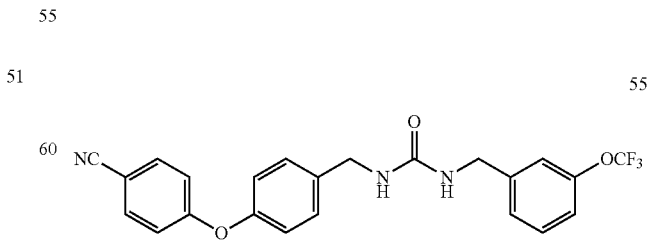

¹H NMR (400 MHz, CDCl₃): δ 7.49 (d, J=9.2 Hz, 2H), 7.17 (t, J=8.0 Hz, 1H), 7.10 (d, J=8.4 Hz, 2H), 7.00-6.92 (m,

3H), 6.88 (d, J=9.2 Hz, 2H), 6.84 (d, J=8.4 Hz, 2H), 6.17-6.05 (m, 2H), 4.10 (m, 4H); HRMS calculated for C$_{23}$H$_{19}$N$_3$O$_3$F$_3$ [M+H]$^+$: 442.1379. Found: 442.1381.

1.2.1.12.

(R)-1-(4-(4-cyanophenoxy)phenyl)-3-(1-(naphthalen-1-yl)ethyl)urea (56)

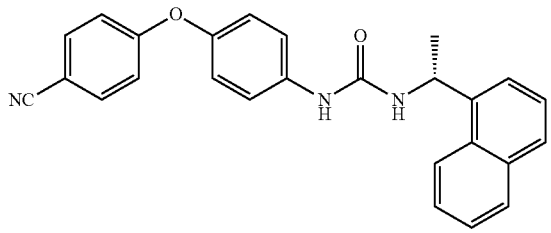

56

$^1$H NMR (400 MHz, MeOD): δ 8.17 (d, J=8.0 Hz, 1H), 7.87 (d, J=8.0 Hz, 1H), 7.78 (d, J=8.0 Hz, 1H), 7.65 (d, J=8.8 Hz, 2H), 7.58 (d, J=7.2 Hz, 1H), 7.53 (d, J=7.2 Hz, 1H), 7.50-7.45 (m, 2H), 7.41 (d, J=8.8 Hz, 2H), 6.99 (t, J=9.2 Hz, 4H), 5.74 (d, J=6.8 Hz, 1H), 1.63 (d, J=6.8 Hz, 3H); HRMS calculated for C$_{26}$H$_{20}$N$_3$O$_2$[M−H]$^−$: 406.1556. Found: 406.1563.

1.2.1.13.

1-(4-chloro-3-(trifluoromethyl)benzyl)-3-(4-(4-cyanophenoxy)phenyl)urea (58)

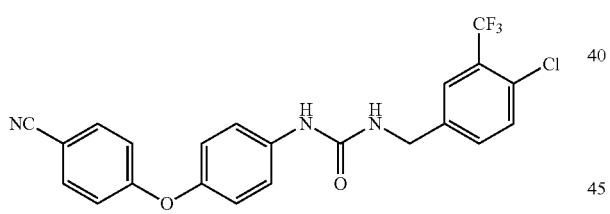

58

$^1$H NMR (400 MHz, MeOD): δ 7.74 (brs, 1H), 7.66 (d, J=9.2 Hz, 2H), 7.56 (d, J=2.0 Hz, 2H), 7.44 (d, J=9.2 Hz, 2H), 7.05-6.98 (m, 4H), 4.43 (s, 2H); HRMS calculated for C$_{22}$H$_{14}$N$_3$O$_2$F$_3$Cl [M−H]$^−$: 444.0727. Found: 444.0736.

1.2.1.14.

1-(4-chloro-3-(trifluoromethyl)phenyl)-3-(3-(4-cyanophenoxy)-4-methylphenyl)urea (59)

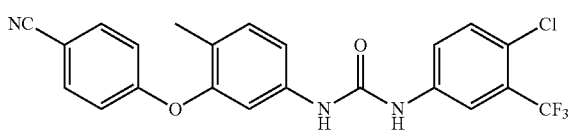

59

$^1$H NMR (400 MHz, MeOD): δ 7.87 (d, J=2.8 Hz, 1H), 7.60 (d, J=9.2 Hz, 2H), 7.54 (dd, J=8.4 Hz, 2.4 Hz, 1H), 7.39 (d, J=8.8 Hz, 1H), 7.25 (d, J=2.4 Hz, 1H), 7.18 (d, J=8.0 Hz, 1H), 7.12 (dd, J=8.0 Hz, 2.4 Hz, 1H), 6.93 (d, J=9.6 Hz, 2H), 2.02 (s, 3H); HRMS calculated for C$_{22}$H$_{14}$N$_3$O$_2$F$_3$Cl [M−H]$^−$: 444.0727. Found: 444.0725.

1.2.1.15.

1,3-bis(3-(4-cyanophenoxy)-4-methylphenyl)urea (60)

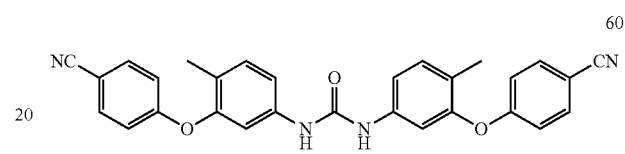

60

$^1$H NMR (400 MHz, DMSO): δ 8.77 (s, 2H), 7.80 (d, J=8.0 Hz, 4H), 7.29 (s, 2H), 7.24 (d, J=8.0 Hz, 2H), 7.13 (d, J=8.4 Hz, 2H), 6.98 (d, J=8.4 Hz, 4H), 2.02 (s, 6H); HRMS calculated for C$_{29}$H$_{21}$N$_4$O$_3$ [M−H]$^−$: 473.1614. Found: 473.1619.

1.2.2 General Procedures for Compound 2-25

In a 25 mL two-necked round flask, aniline derivatives (1 mmol) and catalytic amount of pyridine were placed in anhydrous THF (10 mL) at room temperature. Acyl chloride or sulfonyl chloride compounds were added to the mixture and stirred for 2 h at room temperature. The solvent was removed under vacuum and the crude residue purified by chromatography on a silica gel column using EtOAc/Hexane as eluent (1/10 to 1/2). This procedure afforded the expected coupling product as a white solid from 70% to 95% yield.

1.2.2.1.

N-Methyl-4-(4-(phenylsulfonamido)phenoxy)picolinamide (2)

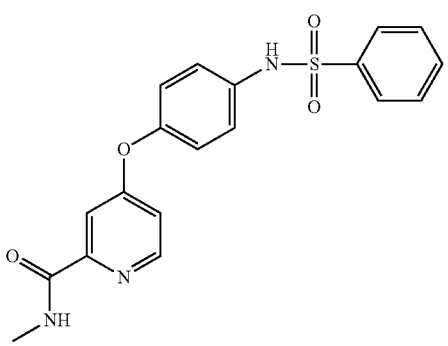 [SMILES: CNC(=O)c1cc(Oc2ccc(NS(=O)(=O)c3ccccc3)cc2)ccn1]

$^1$H NMR (400 MHz, CDCl$_3$): δ 8.36 (d, 1H, J=5.6 Hz), 8.01 (brs, 1H), 7.76 (d, 2H, J=7.6 Hz), 7.59 (s, 1H), 7.54 (t, 1H, J=8.0 Hz), 7.46 (t, 2H, J=8.0 Hz), 7.12 (d, 2H, J=8.8 Hz), 6.94 (d, 2H, J=8.8 Hz), 6.92-6.90 (m, 1H), 3.00 (d, 3H, J=5.2

Hz); $^{13}$C NMR (100 MHz, CDCl$_3$): δ 166.0, 164.6, 152.1, 151.0, 149.7, 138.9, 134.2, 133.0, 129.0, 127.1, 123.9, 121.6, 114.3, 109.9, 26.1; HRMS calculated for C$_{19}$H$_{17}$N$_3$O$_4$S (M+H): 383.0940. Found: 383.0941.

1.2.2.2.

N-Methyl-4-(4-(4-nitrophenylsulfonamido)phenoxy) picolinamide (3)

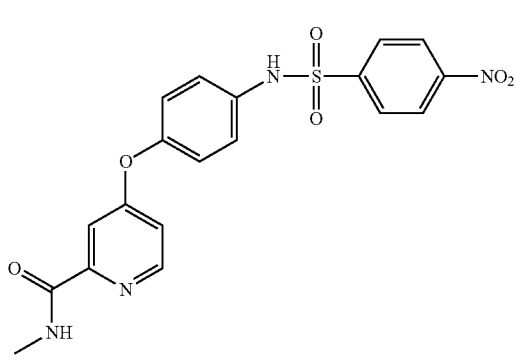 [SMILES: CNC(=O)c1cc(Oc2ccc(NS(=O)(=O)c3ccc([N+](=O)[O-])cc3)cc2)ccn1]

$^1$H NMR (400 MHz, CDCl$_3$): δ 8.39 (d, 1H, J=5.6 Hz), 8.30 (d, 2H, J=8.8 Hz), 8.07 (brs, 1H), 7.93 (d, 2H, J=8.8 Hz), 7.49 (s, 1H), 7.17 (d, 2H, J=8.8 Hz), 7.01-6.98 (m, 3H), 3.00 (d, 3H, J=5.2 Hz); HRMS calculated for C$_{19}$H$_{16}$N$_4$O$_6$S (M+H): 428.0791. Found: 428.0798.

1.2.2.3.

4-(4-(4-Fluorophenylsulfonamido)phenoxy)-N-methylpicolinamide (4)

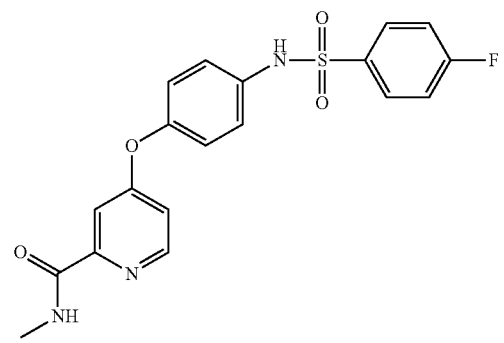 [SMILES: CNC(=O)c1cc(Oc2ccc(NS(=O)(=O)c3ccc(F)cc3)cc2)ccn1]

$^1$H NMR (400 MHz, CDCl$_3$): δ 8.37 (d, 1H, J=5.6 Hz), 8.00 (brs, 1H), 7.77-7.43 (m, 2H), 7.57 (s, 1H), 7.17-7.09 (m, 4H), 6.99-6.93 (m, 4H), 3.00 (d, 3H, J=4.8 Hz); NMR (100 MHz, CDCl$_3$): δ 166.5, 165.9, 164.6, 163.9, 152.1, 151.2, 149.7, 135.0, 134.0, 130.0, 129.9, 124.1, 121.7, 116.4, 116.2, 114.5, 109.8, 26.19; HRMS calculated for C$_{19}$H$_{16}$FN$_3$O$_4$S (M+H): 401.0846. Found: 401.0849.

1.2.2.4.

4-(4-(4-tert-Butylphenylsulfonamido)phenoxy)-N-methylpicolinamide (5)

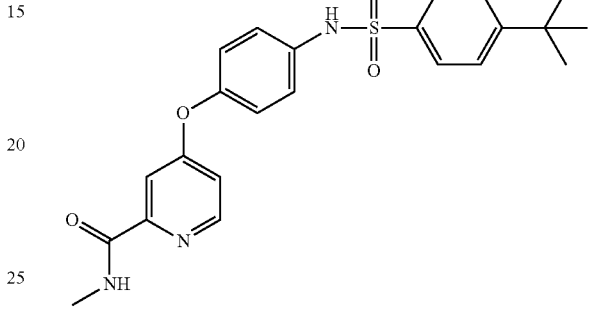

$^1$H NMR (400 MHz, CDCl$_3$): δ 8.33 (d, 1H, J=6.0 Hz), 8.21 (brs, 1H), 7.79 (brs, 1H), 7.69 (d, 2H, J=6.8 Hz), 7.62 (s, 1H), 7.44 (d, 2H, J=6.8 Hz), 7.15 (d, 2H, J=6.8 Hz), 6.91 (s, 2H, J=6.8 Hz), 6.88-6.86 (m, 1H), 2.98 (d, 3H, J=5.2 Hz); $^{13}$C NMR (100 MHz, CDCl$_3$): δ 166.0, 164.6, 156.8, 152.2, 150.8, 149.7, 136.1, 134.4, 127.0, 126.1, 123.6, 121.6, 114.1, 110.1, 35.1, 30.1, 26.1; HRMS calculated for C$_{23}$H$_{25}$N$_3$O$_4$S (M+H): 439.1566. Found: 439.1564.

1.2.2.5.

N-Methyl-4-(4-(naphthalene-2-sulfonamido)phenoxy)picolinamide (6)

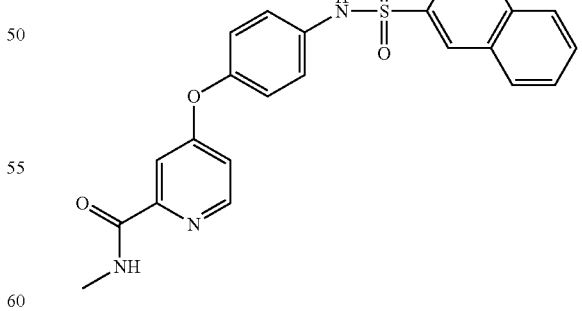

$^1$H NMR (400 MHz, CDCl$_3$): δ 8.34 (s, 1H), 8.30 (d, 1H, J=5.2 Hz), 8.05-8.02 (m, 1H), 7.89-7.83 (m, 4H), 7.74 (dd, 1H, J=8.4, 1.6 Hz), 7.60-7.52 (m, 3H), 7.16 (d, 2H, J=8.8 Hz), 6.88 (d, 2H, J=8.8 Hz), 6.84-6.82 (m, 1H); $^{13}$C NMR (100 MHz, CDCl$_3$): 165.9, 164.6, 152.1, 151.0, 149.7, 135.9, 134.9, 134.2, 132.0, 129.4, 129.3, 128.9, 128.7, 127.9, 127.5, 123.9, 122.2, 121.6, 114.2, 110.1, 26.2; HRMS calculated for C$_{23}$H$_{19}$N$_3$O$_4$S (M+H): 433.1096. Found: 433.1079.

1.2.2.6. 4-(4-(2-Bromo-4-(trifluoromethyl)phenylsulfonamido)phenoxy)-N-methylpicolinamide (7)

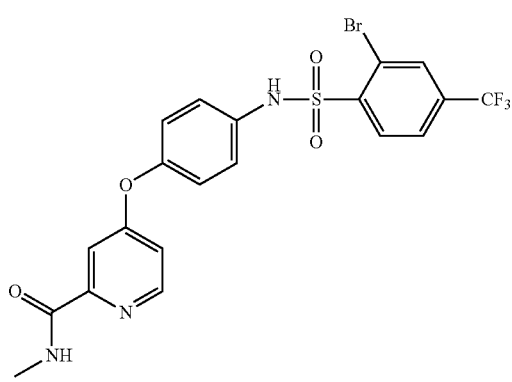 [SMILES: CNC(=O)c1cc(Oc2ccc(NS(=O)(=O)c3ccc(C(F)(F)F)cc3Br)cc2)ccn1]

$^1$H NMR (400 MHz, CDCl$_3$): δ 8.35 (d, 1H, J=5.6 Hz), 8.15 (d, 1H, J=8.0 Hz), 7.79 (brs, 1H), 7.96 (s, 1H), 7.67 (d, 2H, J=8.0 Hz), 7.57 (s, 1H), 7.18 (d, 2H, J=9.2 Hz), 6.95 (d, 2H, J=9.2 Hz), 6.90-6.88 (m, 1H), 2.98 (d, 3H, J=5.2 Hz); $^{13}$C NMR (100 MHz, CDCl$_3$): δ 165.7, 164.5, 152.2, 151.6, 149.8, 141.5, 136.1, 135.8, 135.5, 135.2, 132.7, 132.2 (m), 124.9 (m), 124.1, 123.5, 121.7, 120.8, 120.4, 114.5, 110.0, 26.1; HRMS calculated for C$_{20}$H$_{15}$BrF$_3$N$_3$O$_4$S (M+H): 528.9919. Found: 528.9917.

1.2.2.7.

N-Methyl-4-(4-(2-nitrophenylsulfonamido)phenoxy) picolinamide (8)

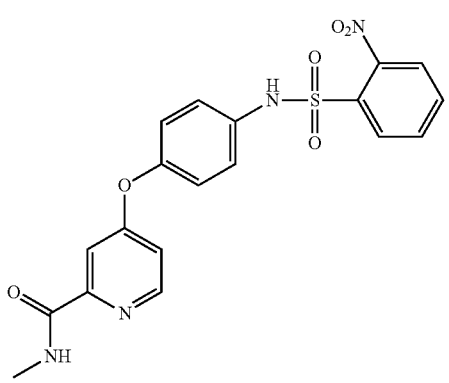 [SMILES: CNC(=O)c1cc(Oc2ccc(NS(=O)(=O)c3ccccc3[N+](=O)[O-])cc2)ccn1]

$^1$H NMR (400 MHz, CDCl$_3$): δ 8.37 (d, 1H, J=6.0 Hz), 7.98 (brs, 1H), 7.86-7.83 (m, 2H), 7.72-7.68 (m, 2H), 7.55 (s, 1H), 7.24 (d, 2H, J=8.8 Hz), 6.98 (d, 2H, J=8.8 Hz), 6.94-6.92 (m, 1H), 2.98 (d, 3H, J=4.8 Hz); HRMS calculated for C$_{19}$H$_{16}$N$_4$O$_6$S (M+H): 428.0791. Found: 428.0796.

1.2.7.8

4-(4-(3,5-Bis(trifluoromethyl)benzamido)phenoxy)-N-methylpicolinamide (9)

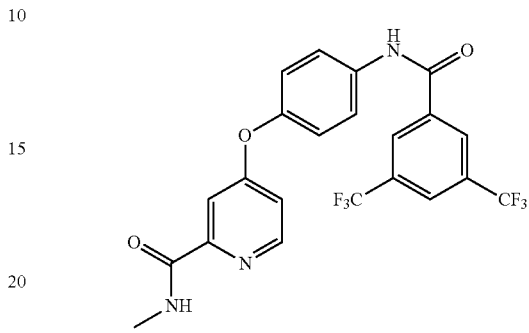

$^1$H NMR (400 MHz, CDCl$_3$): δ 9.92 (s, 1H), 8.40 (s, 1H), 8.33 (d, 1H, J=5.6 Hz), 8.10 (q, 1H, J=5.2 Hz), 7.90 (s, 1H), 7.71 (d, 2H, J=8.8 Hz), 7.40 (d, 1H, J=2.8 Hz), 6.99-6.97 (m, 1H), 6.93 (d, 2H, J=8.8 Hz), 2.91 (d, 3H, J=4.8 Hz); $^{13}$C NMR (100 MHz, methanol-d$_4$): δ 167.8, 166.8, 165.1, 153.4, 151.8, 151.6, 138.6, 137.6, 133.6, 133.3, 133.0, 132.6, 129.4 (d), 126.2 (m), 126.0, 124.2, 123.2, 122.4, 115.2, 110.7, 26.4; HRMS calculated for C$_{22}$H$_{15}$F$_6$N$_3$O$_3$ (M+H): 483.1018. Found: 483.1017.

1.2.2.9

4-(4-(5-Fluoro-2-(trifluoromethyl)benzamido)phenoxy)-N-methylpicolinamide (10)

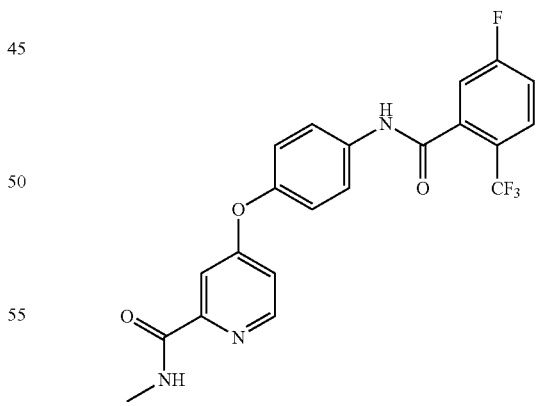

$^1$H NMR (400 MHz, CDCl$_3$): δ 8.66 (d, 1H, J=12.4 Hz), 8.31-8.26 (m, 2H), 7.93 (s, 1H), 7.70-7.65 (m, 3H), 7.56 (t, 1H, J=2.4 Hz), 7.24-7.19 (m, 1H), 7.02 (d, 2H, J=6.4 Hz), 6.89-6.87 (m, 1H), 2.90 (d, 3H, J=3.2 Hz); $^{13}$C NMR (100 MHz, methanol-d$_4$): δ 166.2, 164.5, 162.9, 160.4, 160.0, 159.9, 152.2, 150.4, 149.7, 135.0, 130.6 (m), 129.8 (m), 128.3, 128.1, 127.7, 127.4, 124.5, 122.5, 122.4, 122.3, 121.8, 121.5, 117.2, 117.0, 114.1, 110.1, 26.1; HRMS calculated for $C_{21}H_{15}F_4N_3O_3$ (M+H): 433.1050. Found: 433.0152.

1.2.2.10.

N-Methyl-4-(4-(4-(trifluoromethyl)benzamido)phenoxy)picolinamide (11)

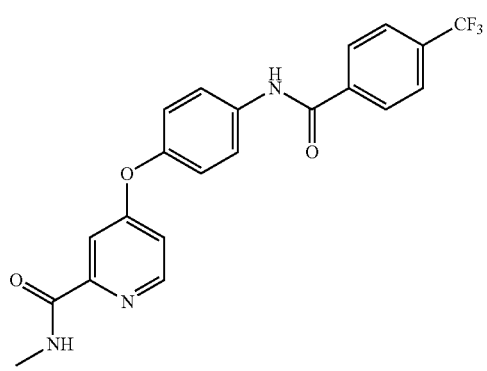 [SMILES: CNC(=O)c1cc(Oc2ccc(NC(=O)c3ccc(C(F)(F)F)cc3)cc2)ccn1]

$^1$H NMR (400 MHz, CDCl$_3$): δ 9.45 (s, 1H), 8.31 (d, 1H, J=5.6 Hz), 8.15 (s, 1H), 8.08 (d, 2H, J=8.0 Hz), 7.71-7.65 (m, 3H), 7.50 (d, 1H, J=2.4 Hz), 7.47 (t, 1H, J=8.0 Hz), 6.96-6.91 (m, 3H), 2.92 (d, 3H, J=5.2 Hz); $^{13}$C NMR (100 MHz, CDCl$_3$): δ 166.4, 164.8, 164.7, 151.8, 149.9, 149.8, 138.8, 135.5, 131.4, 131.1, 130.8, 130.7, 130.5, 129.1, 128.1, 125.0, 124.3 (m), 122.6, 122.3, 121.2, 114.4, 109.5, 26.1; HRMS calculated for $C_{21}H_{16}F_3N_3O_3$ (M+H): 415.1144. Found: 415.1146.

1.2.2.11.

2-Nitro-N-(4-(quinolin-4-yloxy)phenyl)-4-(trifluoromethyl)benzenesulfonam-ide (12)

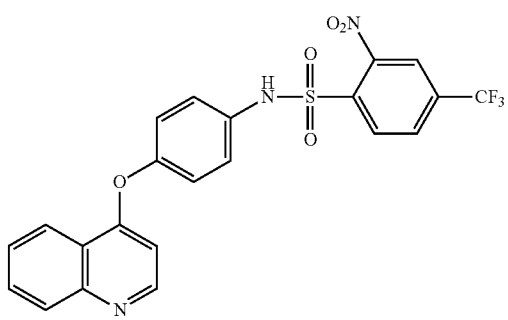 [SMILES: O=[N+]([O-])c1cc(C(F)(F)F)ccc1S(=O)(=O)Nc1ccc(Oc2ccnc3ccccc23)cc1]

$^1$H NMR (400 MHz, CDCl$_3$): δ 8.71 (d, 1H, J=5.2 Hz), 8.28 (d, 1H, J=8.4 Hz), 8.12 (d, 1H, J=8.4 Hz), 8.10 (s, 1H), 8.05 (d, 1H, J=8.4 Hz), 7.89 (d, 1H, J=8.4 Hz), 7.80-7.76 (m, 1H), 7.61-7.57 (m, 1H), 7.31 (d, 2H, J=8.8 Hz), 7.13 (d, 1H, J=8.8 Hz), 6.53 (d, 1H, J=5.2 Hz); HRMS calculated for $C_{22}H_{14}F_3N_3O_5S$ (M+H): 489.0606. Found: 489.0610.

1.2.2.12.

2-Nitro-N-(4-(8-nitroquinolin-4-yloxy)phenyl)-4-(trifluoromethyl)benzenesulfonamide (13)

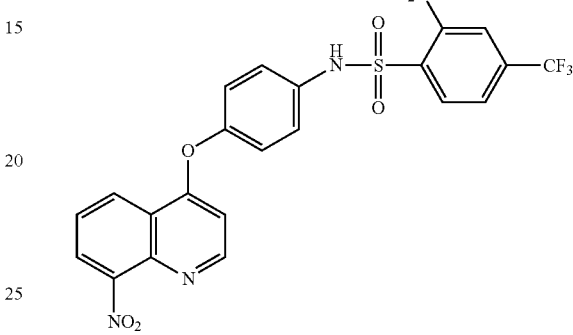

$^1$H NMR (400 MHz, CDCl$_3$): δ 8.78 (d, 1H, J=5.2 Hz), 8.51 (d, 1H, J=8.8 Hz), 8.19 (s, 1H), 8.12-8.02 (m, 3H), 7.89 (t, 1H, J=9.6 Hz), 7.62 (t, 1H, J=8.4 Hz), 7.34 (d, 2H, J=9.6 Hz), 7.15 (d, 2H, J=9.6 Hz), 6.91 (d, 1H, J=6.8 Hz), 6.59 (d, 1H, J=5.2 Hz), 6.55 (d, 1H, J=6.8 Hz); HRMS calculated for $C_{22}H_{13}F_3N_4O_7S$ (M+H): 534.0457. Found: 534.0423.

1.2.2.13

2-Bromo-N-(4-(quinolin-4-yloxy)phenyl)-4-(trifluoromethyl)benzenesulfonamide (14)

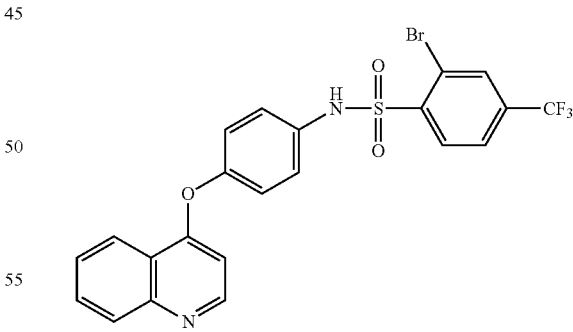

$^1$H NMR (400 MHz, CDCl$_3$): δ 8.65 (d, 1H, J=5.2 Hz), 8.25 (d, 1H, J=8.4 Hz), 8.18 (d, 1H, J=8.4 Hz), 8.07 (d, 1H, J=8.4 Hz), 7.98 (s, 1H), 7.73 (t, 1H, J=7.6 Hz), 7.67 (d, 1H, J=8.4 Hz), 7.54 (t, 1H, J=7.6 Hz), 7.24 (d, 2H, J=8.8 Hz), 7.05 (d, 2H, J=8.8 Hz), 6.43 (d, 1H, J=5.2 Hz); $^{13}$C NMR (100 MHz, CDCl$_3$): δ 161.3, 152.6, 150.9, 149.7, 141.4, 135.9, 135.6, 135.3, 132.7, 132.4, 132.2 (m), 130.3, 129.1, 126.3, 124.9 (m), 124.4, 123.5, 122.1, 122.0, 121.9, 121.6, 121.3, 120.8, 120.4, 116.3, 104.4; HRMS calculated for C$_{22}$H$_{14}$BrF$_3$N$_2$O$_3$S (M+H): 521.9861. Found: 521.9858.

1.2.2.14.

2-Bromo-N-(4-(8-nitroquinolin-4-yloxy)phenyl)-4-(trifluoromethyl)benzenesulfonamide (15)

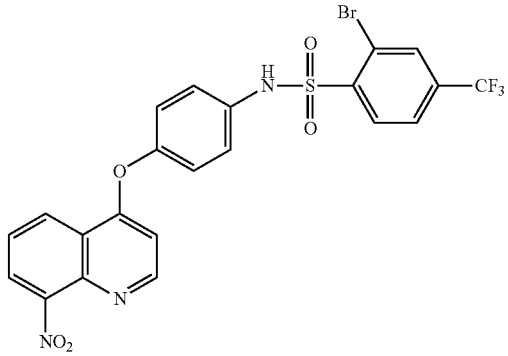 [SMILES: O=[N+]([O-])c1cccc2c(Oc3ccc(NS(=O)(=O)c4ccc(C(F)(F)F)cc4Br)cc3)ccnc12]

$^1$H NMR (400 MHz, CDCl$_3$): δ 8.76 (d, 1H, J=5.2 Hz), 8.49 (d, 1H, J=8.4 Hz), 8.18 (d, 1H, J=8.4 Hz), 8.04 (d, 1H, J=7.6 Hz), 7.99 (s, 1H), 7.68 (d, 1H, J=8.4 Hz), 7.60 (t, 1H, J=8.4 Hz), 7.25 (d, 2H, J=8.4 Hz), 7.07 (d, 2H, J=8.4 Hz), 6.53 (d, 1H, J=5.2 Hz); HRMS calculated for C$_{22}$H$_{13}$BrF$_3$N$_3$O$_5$S (M+H): 566.9711. Found: 566.9706.

1.2.2.15. N-(4-(Quinolin-4-yloxy)phenyl)-3,5-bis(trifluoromethyl)benzamide (16)

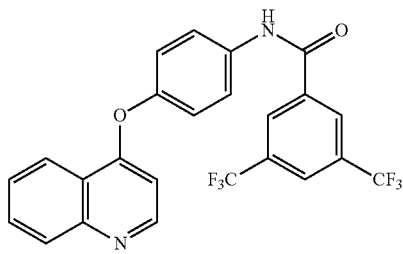 [SMILES: O=C(Nc1ccc(Oc2ccnc3ccccc23)cc1)c1cc(C(F)(F)F)cc(C(F)(F)F)c1]

$^1$H NMR (400 MHz, CDCl$_3$): δ 10.02 (s, 1H), 8.59 (d, 1H, J=5.6 Hz), 8.37 (s, 2H), 8.34 (d, 1H, J=8.4 Hz), 7.99 (d, 1H, J=8.4 Hz), 7.92 (s, 1H), 7.80 (d, 2H, J=9.2 Hz), 7.70 (t, 1H, J=7.6 Hz), 6.56 (t, 1H, J=7.6 Hz), 7.14 (d, 2H, J=9.2 Hz), 6.52 (d, 1H, J=5.2 Hz); $^{13}$C NMR (100 MHz, DMSO-d$_6$): δ 162.6, 161.0, 151.5, 150.0, 149.2, 137.0, 136.1, 131.0, 130.7, 130.4, 130.3, 130.0, 128.8, 128.5 (m), 126.4, 125.2 (m), 124.5, 122.5, 121.7, 121.5, 121.3, 120.6, 104.3; HRMS calculated for C$_{24}$H$_{14}$F$_6$N$_2$O$_2$ (M+H): 476.0959. Found: 476.0958.

1.2.2.16

N-(4-(8-Nitroquinolin-4-yloxy)phenyl)-3,5-bis(trifluoromethyl)benzamide (17)

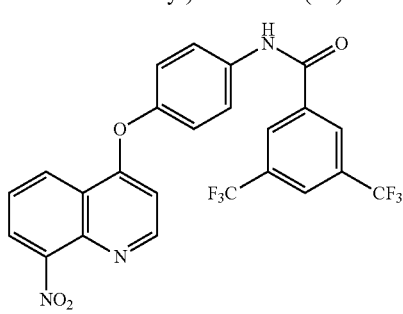

$^1$H NMR (400 MHz, CDCl$_3$): δ 9.05 (s, 1H), 8.69 (d, 1H, J=5.0 Hz), 8.59 (d, 1H, J=5.0 Hz), 8.35 (s, 2H), 8.06 (d, 1H, J=7.8 Hz), 7.97 (s, 1H), 7.80 (d, 2H, J=9.0 Hz), 7.63 (t, 1H, J=8.6 Hz), 7.16 (d, 2H, J=9.0 Hz), 6.62 (d, 1H, J=5.0 Hz); HRMS calculated for C$_{24}$H$_{13}$F$_6$N$_3$O$_4$ (M+H): 521.0810. Found: 521.0814.

1.2.2.17 2-Fluoro-N-(4-(quinolin-4-yloxy)phenyl)-5-(trifluoromethyl)benzamide (18)

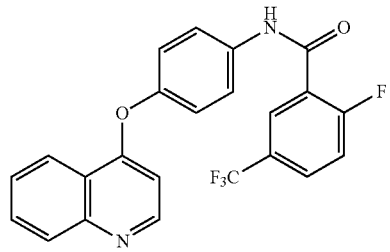 [SMILES: O=C(Nc1ccc(Oc2ccnc3ccccc23)cc1)c1cc(C(F)(F)F)ccc1F]

$^1$H NMR (400 MHz, CDCl$_3$): δ 8.83 (d, 1H, J=12.8 Hz), 8.68 (d, 1H, J=5.2 Hz), 8.39-8.30 (m, 2H), 8.11 (d, 1H, J=8.4 Hz), 7.79-7.67 (m, 4H), 7.58 (t, 1H, J=8.0 Hz), 7.27-7.22 (m, 1H), 7.18 (d, 2H, J=9.2 Hz), 6.56 (d, 1H, J=5.2 Hz); $^{13}$C NMR (100 MHz, methanol-d$_4$): δ 164.4, 164.2, 163.8, 161.7, 151.9, 151.8, 149.7, 137.5, 132.1 (m), 131.2 (m), 128.9 (m), 128.3, 128.1, 127.9, 126.5, 126.3, 123.7, 123.6, 123.0, 122.7, 122.6, 119.1, 119.8, 118.7, 118.5, 105.2; HRMS calculated for C$_{23}$H$_{14}$F$_4$N$_2$O$_2$ (M+H): 426.0991. Found: 426.0991.

1.2.2.18.

2-Fluoro-N-(4-(8-nitroquinolin-4-yloxy)phenyl)-5-(trifluoromethyl)benzami-de (19)

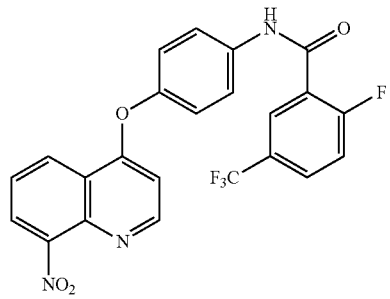 [SMILES: O=C(Nc1ccc(Oc2ccnc3c([N+](=O)[O-])cccc23)cc1)c1cc(C(F)(F)F)ccc1F]

$^1$H NMR (400 MHz, CDCl$_3$): δ 8.81 (d, 1H, J=5.2 Hz), 8.59 (d, 1H, J=8.8 Hz), 8.53-8.47 (m, 2H), 8.06 (d, 1H, J=7.6 Hz), 7.83-7.77 (m, 3H), 7.64 (t, 1H, J=7.6 Hz), 7.37-7.32 (m, 1H), 7.23-7.20 (m, 2H), 6.68 (d, 1H, J=5.2 Hz); HRMS calculated for C$_{23}$H$_{13}$F$_4$N$_3$O$_4$(M+H): 471.0842. Found: 471.0850.

1.2.2.19

N-(3-Methyl-4-(8-nitroquinolin-4-yloxy)phenyl)-3,5-bis(trifluoromethyl)benzamide (20)

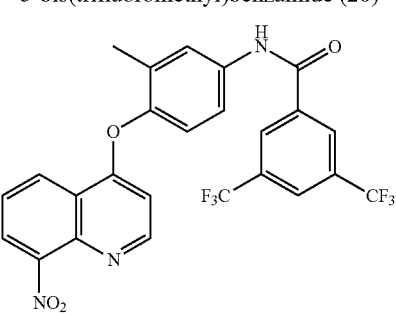

¹H NMR (400 MHz, CDCl₃): δ 9.86 (s, 1H), 8.45 (d, 1H, J=5.2 Hz), 8.38 (s, 2H), 8.31 (d, 1H, J=8.4 Hz), 7.92 (s, 1H), 7.89 (d, 1H, J=8.4 Hz), 7.69-7.63 (m, 2H), 7.53 (t, 1H, J=7.6 Hz), 7.33 (s, 1H), 7.28 (d, 1H, J=8.4 Hz), 6.33 (d, 1H, J=5.2 Hz); HRMS calculated for $C_{25}H_{15}F_6N_3O_4$ (M+H): 535.0967 Found: 535.0956.

1.2.2.20.

N-(4-(8-Aminoquinolin-4-yloxy)-3-methylphenyl)-3,5-bis(trifluoromethyl)benzamide (21)

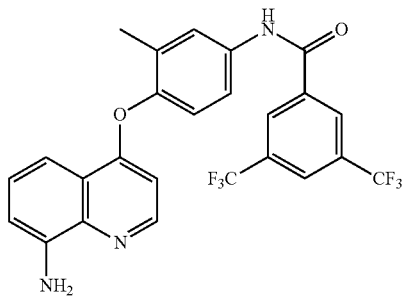 [SMILES: Cc1cc(NC(=O)c2cc(C(F)(F)F)cc(C(F)(F)F)c2)ccc1Oc1ccnc2c([N+](=O)[O-])cccc12]

¹H NMR (400 MHz, CDCl₃): δ 8.49 (d, 1H, J=2.0 Hz), 8.27 (s, 1H), 8.02 (s, 1H), 7.94 (s, 1H), 7.65 (d, 1H, J=8.0 Hz), 7.48-7.45 (m, 2H), 7.37-7.32 (m, 2H), 6.96 (d, 1H, J=7.6 Hz), 4.95 (s, 2H), 2.16 (s, 3H); HRMS calculated for $C_{25}H_{17}F_6N_3O_2$ (M+H): 505.1225. Found: 505.1216.

1.2.2.21.

N-(4-(8-Acetamidoquinolin-4-yloxy)-3-methylphenyl)-3,5-bis(trifluoromethyl)benzamide (22)

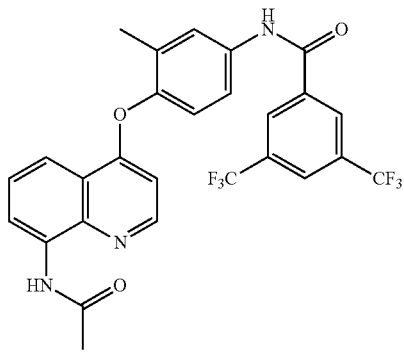 [SMILES: CC(=O)Nc1cccc2c(Oc3ccc(NC(=O)c4cc(C(F)(F)F)cc(C(F)(F)F)c4)cc3C)ccnc12]

¹H NMR (400 MHz, CDCl₃): δ 9.77 (s, 1H), 9.36 (s, 1H), 8.65 (d, 1H, J=7.2 Hz), 8.46 (s, 2H), 8.44 (d, 1H, J=5.2 Hz), 7.97 (s, 1H), 7.87 (d, 1H, J=8.4 Hz), 7.72 (d, 1H, J=8.4 Hz), 7.50 (d, 1H, J=2.0 Hz), 7.37 (t, 1H, J=8.0 Hz), 7.28 (d, 1H, J=8.4 Hz), 6.41 (d, 1H, J=5.2 Hz), 2.26 (s, 3H), 2.10 (s, 3H); ¹³C NMR (100 MHz, CDCl₃): δ 169.2, 163.0, 161.2, 152.0, 148.8, 139.5, 137.2, 136.7, 133.8, 132.6, 132.3, 132.0, 131.6, 127.8, 127.1, 126.3, 125.2 (m), 124.2, 121.5, 120.4, 118.8, 118.3, 116.7, 115.7, 113.8, 25.0, 15.4; HRMS calculated for $C_{27}H_{19}F_6N_3O_3$ (M+H): 547.1331. Found: 547.1325.

1.2.2.22.

N-(3-(8-Nitroquinolin-4-yloxy)phenyl)-3,5-bis(trifluoromethyl)benzamide (23)

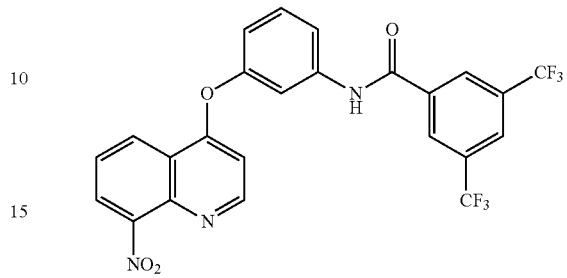

¹H NMR (400 MHz, CDCl₃): δ 8.78 (d, 1H, J=5.6 Hz), 8.58 (d, 1H, J=8.4 Hz), 8.52 (s, 1H), 8.31 (s, 2H), 8.22 (s, 1H), 8.08-8.04 (m, 2H), 7.71 (s, 1H), 7.64 (t, 1H, J=8.0 Hz), 7.53-7.49 (m, 2H), 7.03 (d, 1H, J=7.2 Hz), 6.71 (d, 1H, J=4.8 Hz); HRMS calculated for $C_{24}H_{13}F_6N_3O_4$ (M+H): 521.0810. Found: 521.0821.

1.2.2.23.

N-(3-(8-Aminoquinolin-4-yloxy)phenyl)-3,5-bis(trifluoromethyl)benzamide (24)

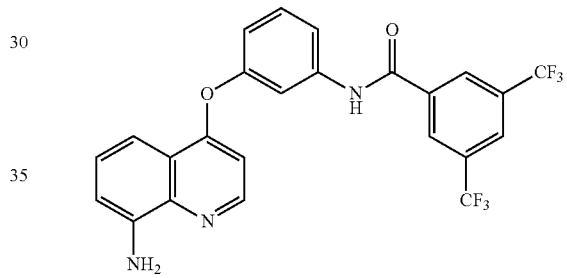

¹H NMR (400 MHz, CDCl₃): δ 8.55 (d, 1H, J=4.8 Hz), 8.29 (s, 2H), 8.05 (s, 1H), 7.90 (s, 1H), 7.60 (d, 1H, J=8.4 Hz), 7.55 (s, 1H), 7.70-7.43 (m, 2H), 7.34 (t, 1H, J=8.0 Hz), 7.01 (d, 1H, J=8.0 Hz), 6.96 (d, 1H, J=7.9 Hz), 6.63 (d, 1H, J=4.8 Hz); ¹³C NMR (100 MHz, CDCl₃): δ 163.1, 161.3, 155.3, 147.9, 143.6, 139.9, 138.8, 136.5, 132.7, 132.4, 132.1, 131.7, 130.6, 127.5 (d), 127.0, 126.8, 125.3 (m), 124.1, 122.0, 118.7, 117.4, 117.2, 113.1, 111.1, 110.0, 105.4; HRMS calculated for $C_{24}H_{15}F_6N_3O_2$ (M+H): 491.1068. Found: 491.1068.

1.2.2.24.

N-(3-(8-Acetamidoquinolin-4-yloxy)phenyl)-3,5-bis(trifluoromethyl)benzam-ide (25)

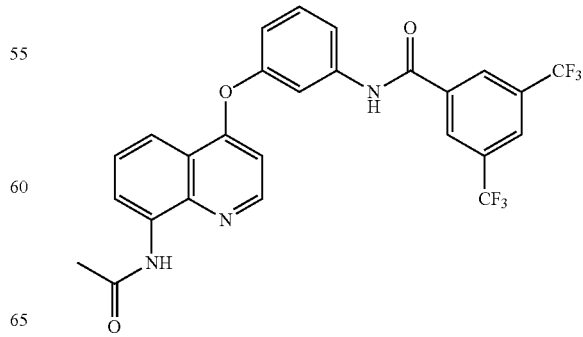

¹H NMR (400 MHz, CDCl₃): δ 9.77 (s, 1H), 8.74 (d, 1H, J=7.6 Hz), 8.54 (d, 1H, J=5.2 Hz), 8.48 (s, 1H), 8.39 (s, 2H), 8.04 (s, 1H), 7.87 (d, 1H, J=8.4 Hz), 7.67-7.60 (m, 2H), 7.50-7.43 (m, 2H), 7.37 (t, 1H, J=8.0 Hz), 7.00 (d, 1H, J=8.4 Hz), 6.65 (d, 1H, J=5.2 Hz), 2.30 (s, 3H); ¹³C NMR (100 MHz, CDCl₃): δ 169.3, 163.1, 161.7, 154.6, 148.7, 139.6, 136.6, 133.8, 132.7, 132.4, 132.1, 131.7, 130.8, 127.8 (d), 126.9, 126.5, 125.3 (m), 124.2, 121.5, 120.8, 117.7, 117.3, 116.8, 115.7, 113.2, 104.9, 25.0; HRMS calculated for C₂₆H₁₇F₆N₃O₃ (M+H): 533.1174. Found: 533.1167.

1.2.2.25

N-(3-(trifluoromethyl)benzene-sulfonyl)-3-(3-amino-4-nitrophenoxy)benzenamine (SC-40)

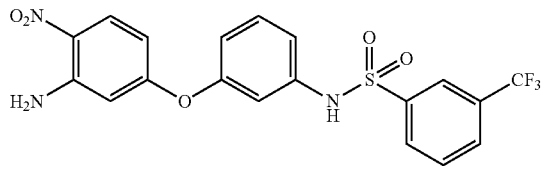 [SMILES: Nc1cc(Oc2cccc(NS(=O)(=O)c3cccc(C(F)(F)F)c3)c2)ccc1[N+](=O)[O-]]

¹H NMR (400 MHz, CDCl₃): δ 8.06 (d, J=9.6 Hz, 1H), 8.00 (s, 1H), 7.96 (d, J=8.0 Hz, 1H), 7.81 (d, J=8.0 Hz, 1H), 7.61 (t, J=8.0 Hz, 1H), 7.27 (t, J=8.0 Hz, 1H), 6.91-6.80 (m, 3H), 6.19 (dd, J=9.6 Hz, 2.4 Hz, 1H), 6.14 (d, J=2.4 Hz, 1H), 6.10 (brs, 2H); ¹³C NMR (100 MHz, CDCl₃): δ 163.1, 155.5, 146.7, 140.0, 137.6, 132.0, 131.6, 130.9, 130.3, 130.0, 129.9 (m), 128.8, 128.0, 124.4, 124.3, 124.2, 124.2, 124.0, 121.6, 117.8, 117.6, 113.6, 107.6, 104.3; LC-MS (ESI): M/Z 452 [M−H]⁻; HRMS calculated for C₁₉H₁₃N₃O₅F₃S [M−H]⁻: 452.0528. Found: 452.0529.

1.2.3 compound 36-38
1.2.3.1

3-(2-phenylH-imidazo[1,2-a]pyridin-7-yloxy)-N-(3-(trifluoromethoxy)benzyl)benzenemine (36)

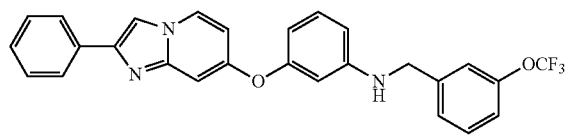 [SMILES: FC(F)(F)Oc1cccc(CNc2cccc(Oc3ccn4cc(-c5ccccc5)nc4c3)c2)c1]

¹H NMR (400 MHz, CDCl₃): δ 7.96 (d, J=8.0 Hz, 1H), 7.89 (d, J=8.0 Hz, 2H), 7.71 (s, 1H), 7.40 (t, J=7.2 Hz, 2H), 7.35-7.24 (m, 3H), 7.18 (s, 1H), 7.14 (t, J=8.0 Hz, 1H), 7.09 (d, J=7.6 Hz, 1H), 6.98 (d, J=2.4 Hz, 1H), 6.60 (dd, J=7.2 Hz, 2.4 Hz, 1H), 6.46-6.40 (m, 2H), 6.32 (t, J=2.4 Hz, 1H), 4.31 (s, 1H), 4.20 (s, 1H); HRMS calculated for C₂₇H₂₁N₃O₂F₃ [M+H]⁺: 476.1586. Found: 476.1592.

1.2.3.2

N-(3-(2-phenylimidazo[1,2-a]pyridin-7-yloxy)phenyl)-3-(trifluoromethyl)benzenesulfonamide (37)

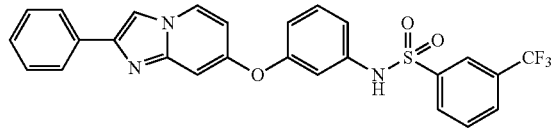 [SMILES: O=S(=O)(Nc1cccc(Oc2ccn3cc(-c4ccccc4)nc3c2)c1)c1cccc(C(F)(F)F)c1]

¹H NMR (400 MHz, CDCl₃): δ 8.03 (d, J=6.8 Hz, 2H), 7.92 (d, J=8.0 Hz, 1H), 7.87 (d, J=6.8 Hz, 2H), 7.76 (d, J=6.0 Hz, 2H), 7.60 (t, J=7.6 Hz, 1H), 7.39 (t, J=8.0 Hz, 2H), 7.30 (t, J=6.4 Hz, 1H), 7.21 (d, J=8.8 Hz, 1H), 6.96-6.90 (m, 2H), 6.83 (dd, J=13.6 Hz, 2.4 Hz, 1H), 6.82 (t, J=2.0 Hz, 2H), 6.60 (dd, J=7.2 Hz, 2.4 Hz, 1H); HRMS calculated for C₂₆H₁₉N₃O₃F₃S [M+H]⁺: 510.1099. Found: 510.1100.

1.2.3.3

N-(3-(2-phenylimidazo[1,2-c]pyridin-7-yloxy)phenyl)benzenesulfonamide (38)

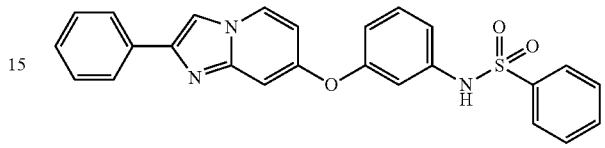

¹H NMR (400 MHz, DMSO): δ 8.52 (d, J=7.2 Hz, 1H), 8.33 (s, 1H), 7.93 (d, J=7.2 Hz, 2H), 7.76-7.70 (m, 2H), 7.66-7.54 (m, 3H), 7.43 (t, J=7.6 Hz, 2H), 7.33-7.26 (m, 2H), 6.92 (d, J=7.6 Hz, 1H), 6.84-6.76 (m, 3H), 6.64 (dd, J=7.6 Hz, 2.4 Hz, 1H); HRMS calculated for C₂₅H₂₀N₃O₃S [M+H]⁺: 442.1225. Found: 442.1216.

Example 2

Bioassay 2.1 Materials and Methods
2.1.1. Reagents and Antibodies

Sorafenib (Nexavar®) was kindly provided by Bayer Pharmaceuticals (West Haven, Conn.). Sodium vanadate and SHP-1 inhibitor were purchased from Cayman Chemical (Ann Arbor, Mich.). Antibodies for immunoblotting such as Raf-1, cylcin D1, and PARP were purchased from Santa Cruz Biotechnology (San Diego, Calif.). Other antibodies such as anti-pVEGFR2 (Y1175), VEGFR2, survivin, phospho-STAT3 (Tyr705), and STAT3 were from Cell Signaling (Danvers, Mass.).

2.1.2. Cell Culture

The Huh-7 HCC cell line was obtained from the Health Science Research Resources Bank (Osaka, Japan; JCRB0403). The PLC/PRF/5 (PLC5), Sk-Hep-1, and Hep3B cell lines were obtained from American Type Culture Collection (Manassas, Va.). The cells were maintained in DMEM supplemented with 10% FBS, 100 units/mL penicillin G, 100 μg/mL streptomycin sulfate and 25 μg/mL amphotericin B in a 37° C. humidified incubator in an atmosphere of 5% $CO_2$ in air. Other cell lines, including breast cancer cells e.g. MDAMB231, MDAMB468, MCF-7, and leukemia cancer cells e.g. HL-60, KG-1 and ML-1 are also provided for the assays described below.

2.1.3. Cell Death Detection ELISA

The effect of the compounds of the invention on cell viability was assessed by cell death ELISA assay (Roche Applied Science. Mannheim, Germany). Cells were treated with a test compound at 5 and 10 μM for 24 h, for example. The cells were collected and applied to the standard protocol provided by manufacture.

2.1.4. Apoptosis Analysis

Apoptotic cells were measured by flow cytometry (sub-G1). After treatment with various compounds, cells were trypsinized, collected by centrifugation and resuspended in PBS. After centrifugation, the cells were washed in PBS and resuspended in potassium iodide (PI) staining solution.

Specimens were incubated in the dark for 30 min at 37° C. and then analyzed with an EPICS Profile II flow cytometer (Coulter Corp., Hialeah, Fla.). All experiments were performed in triplicate 2.1.5. Phospho-STAT3-Level A PathScan Phospho-Stat3 (Tyr705) Sandwich ELISA Kit was used for the detection of phospho-STAT3 (Cell Signaling, Danvers, Mass.). Cells were pre-treated with IL-6 1 ng/ml and then exposed with various compounds at 10 μM for 24 h. After incubation with cell lysates, both non-phospho- and phospho-Stat3 proteins are captured by the coated antibody. The expression of phospho-STAT3 was measured at 450 nm absorbance.

2.1.6. Western Blot

Cells were treated with various compounds at 5 and 10 μM for 24 h. Cell lysates were analyzed by western blot.

2.1.7. Gene Knockdown Using siRNA

Smart-pool siRNA, including control (D-001810-10), Raf-1, SHP-1, SHP-2, and PTP-1B, were all purchased from Dharmacon Inc. (Chicago, Ill.). The procedure has been described previously (Chen K F et al. *J Biol Chem* 2009; 284:11121-11133).

2.1.8. PLC5 with Ectopic Expression of STAT3

STAT3 cDNA (KIAA1524) and STAT3-C were purchased from Addgene plasmid repository (http://www.addgene-.org/). Briefly, following transfection, cells were incubated in the presence of G418 (0.78 mg/mL). After 8 weeks of selection, surviving colonies, i.e., those arising from stably transfected cells, were selected and individually amplified.

2.1.9. Phosphatase and Kinase Activity

The RediPlate 96 EnzChek® Tyrosine Phosphatase Assay Kit (R-22067) was used for SHP-1 activity assay (Molecular Probes, Carlsbad, Calif.). The Raf-1 kinase cascade assay kit (Upstate-Millipore, Billerica, Mass.) was used to examine the Raf-1 kinase activity. The JAK2 kinase activity kit was purchased from Reaction Biology Corp. (Malvern, Pa.).

2.1.10. STAT3 Reporter Assay

Cells were seeded in 96-well plate and pre-treated with IL-6 at the dose 10 ng/μl for 30 min. The STAT3 reporter kit was purchased from SABiosciences (Frederick, Md.).

2.1.11. Xenograft Tumor Growth

Male NCr athymic nude mice (5-7 weeks of age) were obtained from the National Laboratory Animal Center (Taipei, Taiwan). All experimental procedures using these mice were performed in accordance with protocols approved by National Taiwan University. When Huh-7 tumors reached 100-200 mm$^3$, mice received sorafenib tosylate (10 mg/kg) p.o. (oral) once daily, or SC-1 (10 mg/kg) p.o. (oral) once daily. Controls received vehicle (Chen K F et al. Cancer Res. 2008; 68:6698-6707).

2.1.12. Statistical Analysis.

Comparisons of mean values were performed using the independent samples t test in SPSS for Windows 11.5 software (SPSS, Inc., Chicago, Ill.) (Chen K F et al. Cancer Res 2008; 68:6698-6707).

2.2 Results 2.2.1 Compound 1 does not Affect Raf Kinase Activity

Figure 3:
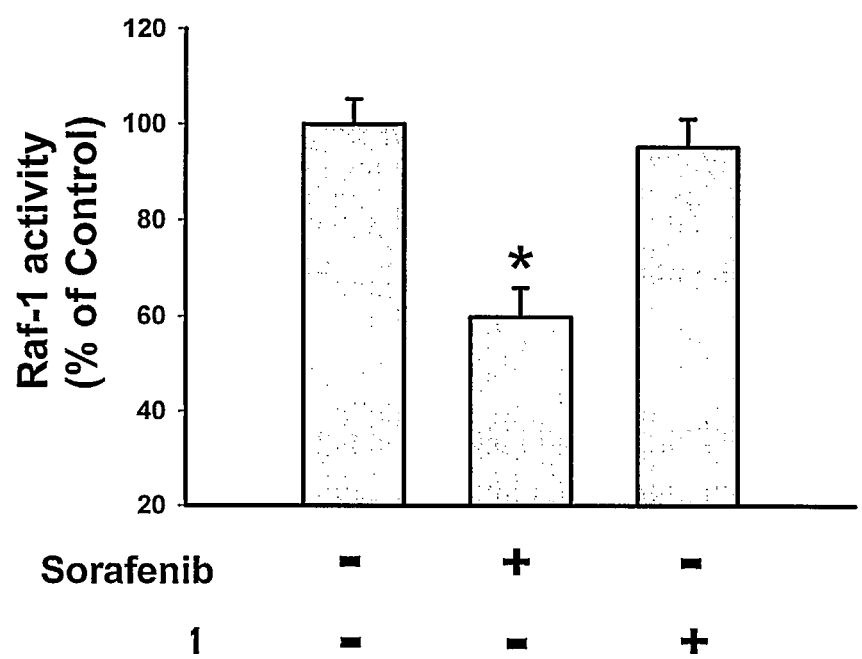
FIG. 3 shows Raf-1 activity in the cells treated by sorafenib and compound 1, respectively. Huh-7 cells were exposed to sorafenib or compound 1 at 10 μM for 24 hours and cell lysates were analyzed for raf-1 activity. Columns, mean; bars, SD (n=3). *P<0.05.

As above described, we synthesized a sorafenib derivative without providing hydrogen donor ability by replacing the pyridine ring and amide functional group with phenyl cyanide. Then, we tested compound 1 for its ability to inhibit Raf kinase activity in PLC5 cells, compared with that of sorafenib. As shown in FIG. 3, sorafenib was able to inhibit 50% of the Raf-1 kinase activity of the untreated cells in the PLC5 cells at 5 μM; however, compound 1 treated cells showed the same Raf-1 activity as vehicle control. The loss of Raf-1 inhibition can presumably be attributed to the loss of hydrogen bonding ability, as a result of the replacement of the pyridine ring and amide functional group with phenyl cyanide.

2.2.2. Structure Activity Relationship of Replacement of Urea Group and Pyridine Ring in Cell Death As above described, we replaced the urea functional group linkage of sorafenib with various amide and sulfonamide, generating compounds 2-11. These compounds were analyzed by MTT assay for cell growth inhibition in the PLC5 cells. Table 4 shows the results.

TABLE 4

| Cpd | R$_4$ | IC$_{50}$ (μM) in PLC5 cells |
|---|---|---|
| Sorafenib | | 8.3 |
| 1 | | 7.5 |
| 2 | 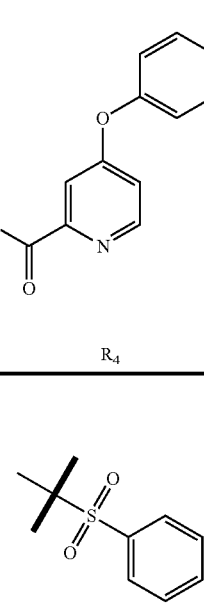 | >40 |
| 3 | 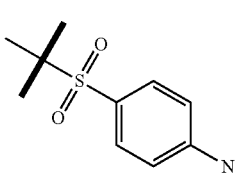 | >40 |
| 4 | 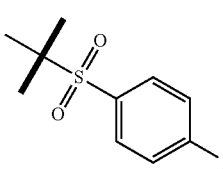 | >40 |
| 5 | 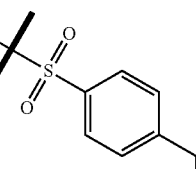 | >40 |
| 6 | 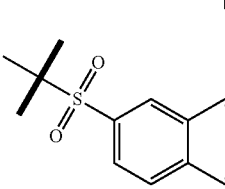 | >40 |

TABLE 4-continued

[Structure: 4-phenoxy-N-methylpyridine-2-carboxamide with R4 on aniline NH]

| Cpd | R4 | IC₅₀ (μM) in PLC5 cells |
|---|---|---|
| 7 | sulfonyl-tBu, 2-Br-4-CF₃-phenyl | >40 |
| 8 | sulfonyl-tBu, 2-NO₂-phenyl | >40 |
| 9 | pivaloyl, 3,5-bis(CF₃)-phenyl | >40 |
| 10 | pivaloyl, 2-F-5-CF₃-phenyl | >40 |
| 11 | pivaloyl, 4-CF₃-phenyl | >40 |

The results show that none of these derivatives within the electron donating or electron withdrawing group showed greater cell toxicity than sorafenib and compound 1.

Next, we changed the pyridine to a quinoline ring and amide linker to generate compounds 12-25. These compounds were also analyzed by MTT assay for cell growth inhibition in the PLC5 cells. Table 5 shows the results.

TABLE 5

[Structure: 4-(4-aminophenoxy)quinoline with R4 on aniline NH]

| Cpd | R4 | IC₅₀ (μM) in PLC5 cells |
|---|---|---|
| 12 | sulfonyl-tBu, 2-NO₂-4-CF₃-phenyl | >40 |
| 14 | sulfonyl-tBu, 2-Br-4-CF₃-phenyl | >40 |
| 16 | pivaloyl, 3,5-bis(CF₃)-phenyl | 16.0 |
| 18 | pivaloyl, 2-F-5-CF₃-phenyl | 21.1 |

TABLE 6

[Structure: 4-(4-aminophenoxy)-8-nitroquinoline with R4 on aniline NH]

| Cpd | R4 | IC₅₀ (μM) in PLC5 cells |
|---|---|---|
| 13 | sulfonyl-tBu, 2-NO₂-4-CF₃-phenyl | >40 |

TABLE 6-continued

[Structure: quinoline with 8-NO2, 4-O-phenyl-NH-R4]

| Cpd | R4 | IC50 (μM) in PLC5 cells |
|---|---|---|
| 15 | [2-Br-4-CF3-phenyl sulfonyl, t-Bu] | >40 |
| 17 | [3,5-bis(CF3)-phenyl C(=O)-, t-Bu] | >40 |
| 19 | [2-F-5-CF3-phenyl C(=O)-, t-Bu] | >40 |

TABLE 6

[Structure: quinoline with 8-NO2, 4-O-(R6-substituted phenyl)-NH-R4]

| Cpd | R4 | R6 | IC50 (μM) in PLC5 cells |
|---|---|---|---|
| 20 | [3,5-bis(CF3)-phenyl C(=O)-, t-Bu] | Me | >40 |
| 23 | [3,5-bis(CF3)-phenyl C(=O)-, t-Bu] | H | >40 |

TABLE 6-continued

[Structure: quinoline with 8-NH2, 4-O-(R6-substituted phenyl)-NH-R4]

| Cpd | R4 | R6 | IC50 (μM) in PLC5 cells |
|---|---|---|---|
| 21 | [3,5-bis(CF3)-phenyl C(=O)-, t-Bu] | Me | 25.4 |
| 24 | [3,5-bis(CF3)-phenyl C(=O)-, t-Bu] | H | 19.0 |

[Structure: quinoline with 8-NHC(=O)CH3, 4-O-(R6-substituted phenyl)-NH-R4]

| Cpd | R4 | R6 | IC50 (μM) in PLC5 cells |
|---|---|---|---|
| 22 | [3,5-bis(CF3)-phenyl C(=O)-, t-Bu] | Me | >40 |

TABLE 6-continued

| | | | |
|---|---|---|---|
| 25 | CF3-substituted phenyl ketone (3,5-bis(CF3)phenyl ketone group) | H | 10.8 |

The amide linker showed different conformation from the sulfonyl linker, exhibiting better activity than sulfonyl linker compounds. For example, compound 16 showed a better cell toxicity than compound 12. Compound 25 showed cytotoxicity comparable to sorafenib and 1. We concluded that the urea and amide linkers exhibited the most potent cell toxicity in PLC5 cells.

2.2.3. Mechanistic Validation of the Mode of Action of Sorafenib Derivatives

Figure 4:
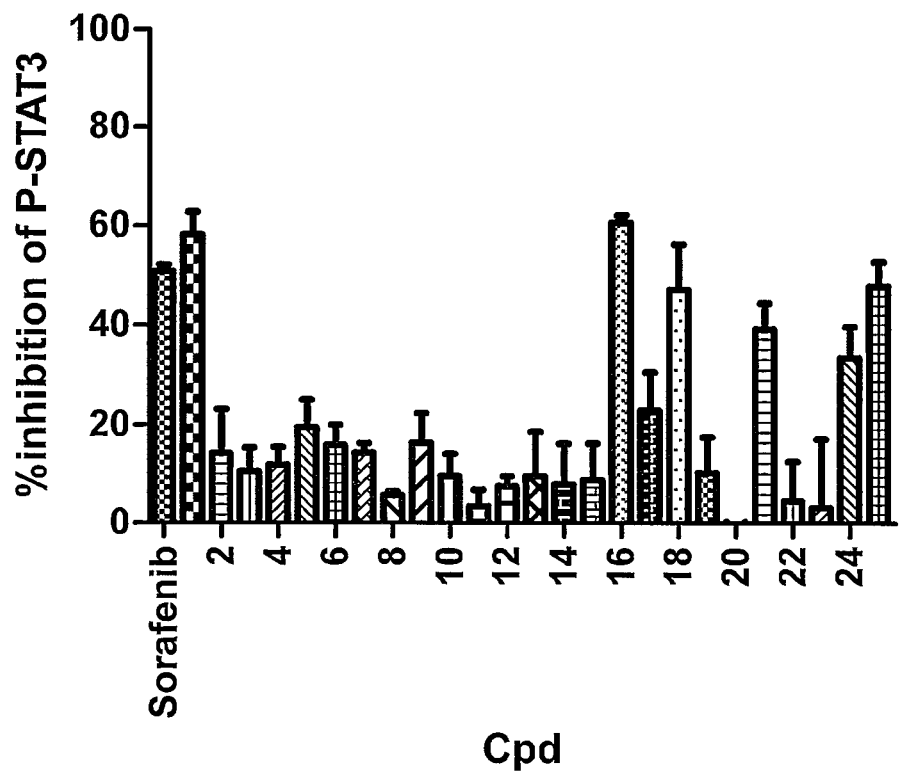
FIG. 4 shows the results of the ELISA analysis for the inhibitory effects of compounds 1-25 versus sorafenib, each at 10 μM, on the IL-6 stimulated P-STAT in PLC5 cells after 24 h of treatment. Columns, mean, bars, SD (N=3).

To check the dephosphorylation of STAT3 by sorafenib derivatives, we assessed P-STAT3 state in PLC5 cells exposed to 10 uM of each compound for 24 h by ELISA. As showed in FIG. 4, sulfonyl linker compounds showed no appreciable change in P-STAT3; however, compound 1 and some of the amide linker compounds showed a high degree of dephosphorylation of STAT3. The decreased level of P-STAT3 induced by these derivatives was correlated with cell toxicity. In the other words, these derivatives induced cell death in part through inhibition of STAT3.

Figure 5:
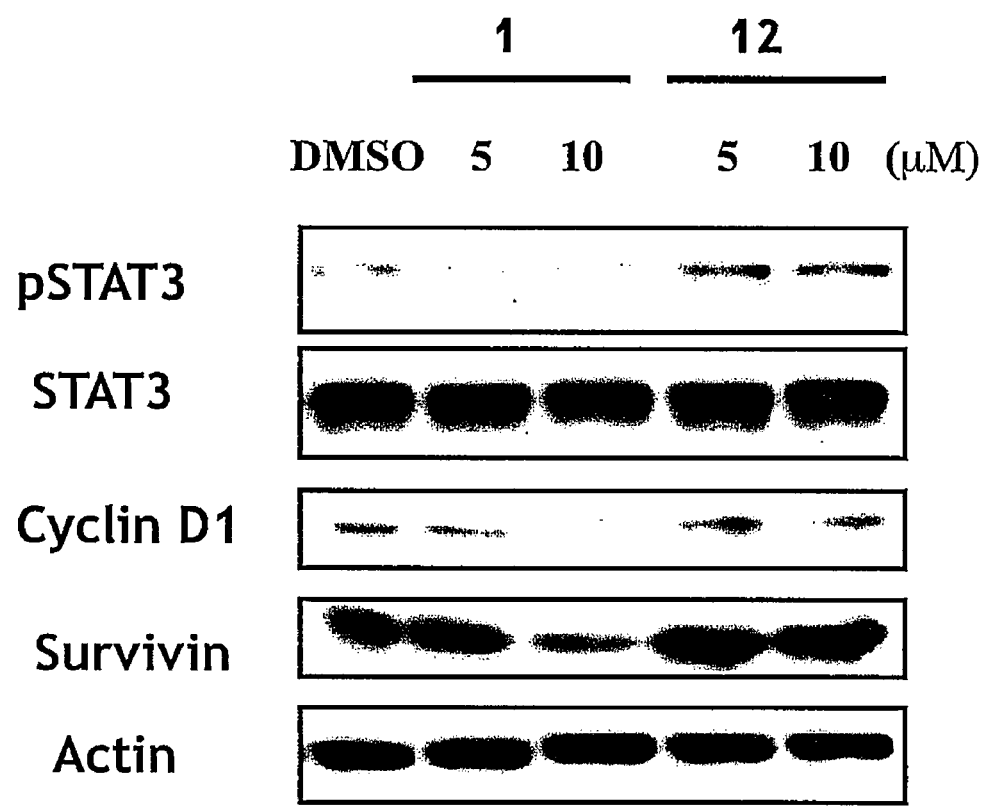
FIG. 5 shows the results of Western blot analysis for the effect of compounds 1 and 12, each at 5 μM and 10 μM on the phosporylation of P-STAT3, STAT3, cyclin D and survivin in PLC5 cells in FBS-containing medium after 24 h of treatment.
Figure 6:
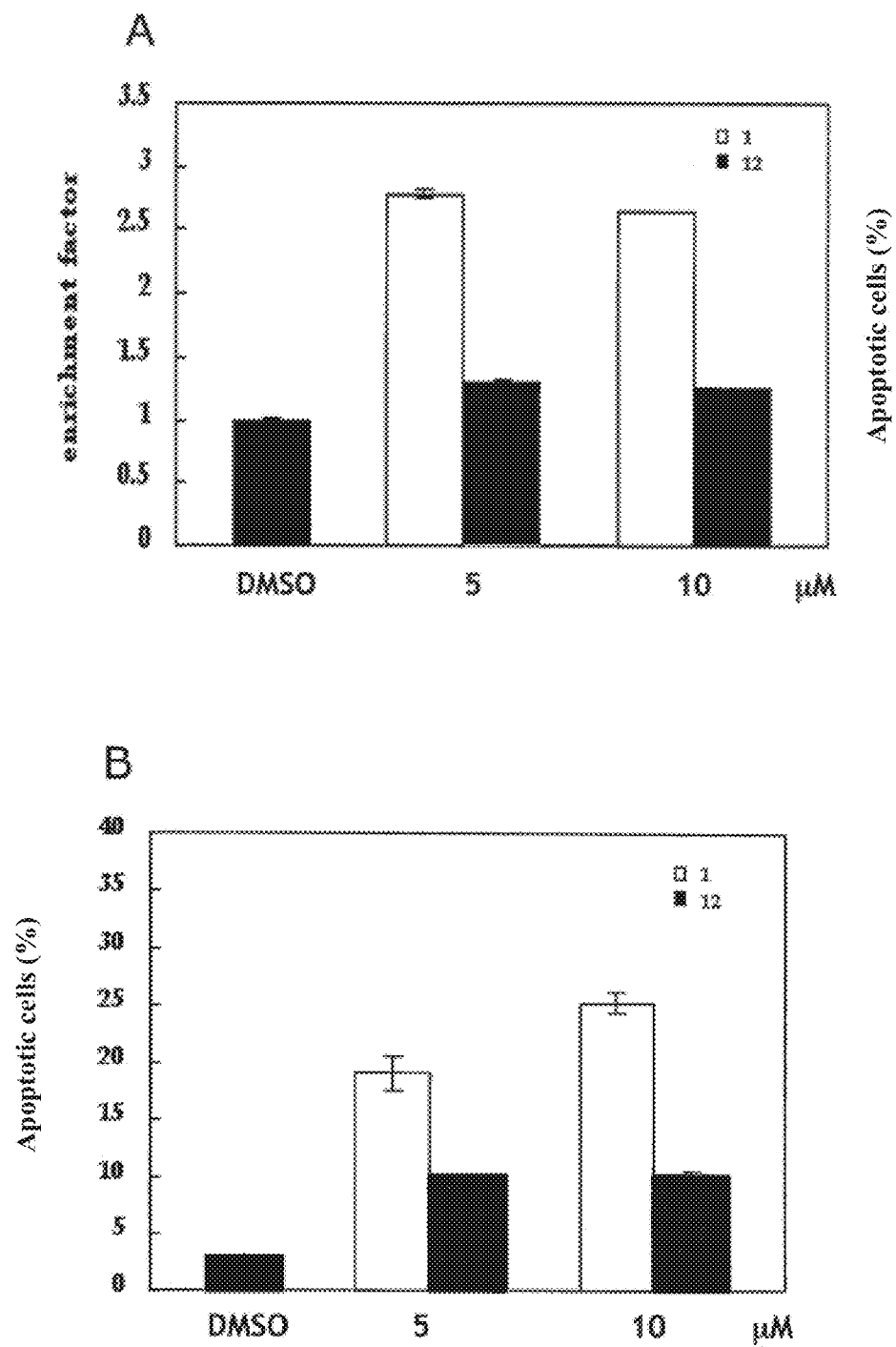
FIG. 6 shows (A) the results of ELISA analysis for cell death induced by compound 1 and 12, at 5, and 10 μM, after 24 h of treatment in PLC5 cells; and (B) shows the results of flow cytometry analysis of cell death induced by compound 1 and 12, at 5, and 10 μM, after 24 h of treatment in PLC5 cells.

In addition, we tested the downstream signal pathway after the inhibition of P-STAT3. Expression levels of the cyclin D1 and survivin, downstream target genes of STAT3, were assessed using compounds 1 and 12. As shown in FIG. 5, compound 1 with STAT3 inhibitory activity, was able to reduce cyclin D1 and survivin level, but compound 12 had no effect on either protein. Further, DNA fragmentation and flow cytometry analysis of PLC5 cells treated with compound 1 were conducted, and the results show that cell death was attributed to the inhibition of STAT3 and further induced the apoptotic signal (FIG. 6).

Our premise that sorafenib inhibition of Raf and STAT3 could be structurally dissociated was borne out by compound 1, which, devoid of Raf activity, exhibited the same level of downregulation of P-STAT3 as sorafenib did. We suggest that the cyanide group of compound 1 reduces its interaction with Raf. Subsequent modifications of sorafenib by changing the linker and pyridine ring to amide and quinoline (compounds 1, 16, and 25, respectively) resulted in a decrease in STAT3-repressing potency.

2.2.4. SC-1, a Sorafenib Derivative, Lacking Inhibitory Function of Raf-1 Showed Similar Cell Death Effect to Sorafenib in HCC Cell Lines.

Figure 7:
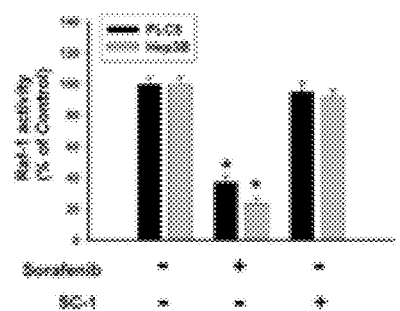
FIG. 7 shows (A) the effects of sorafenib and SC-1 on phospho-VEGFR2 in HUVEC cells, wherein the cells were exposed to sorafenib or SC-1 at 10 μM for 24 h; (B) the effects of sorafenib and SC-1 on Raf-1 activity, wherein the cells were exposed to sorafenib or SC-1 at 10 μM for 24 h. Points, mean; bars, SD (n=6).
Figure 7:
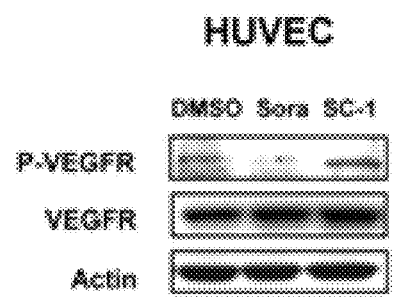

In this experiment, we again examined the effects of sorafenib and SC-1 on Raf-1 activity. Raf-1 immunoprecipitated from PLC5 or Hep3B cell extracts was incubated with MEK recombinant protein and the phospho-MEK was status assayed in the sorafenib or SC-1-treated cells. We observed a 20-40% reduction in Raf-1 kinase activity in the presence of sorafenib; however, SC-1 did not inhibit the activity of Raf-1, suggesting that SC-1 is not a Raf-1 inhibitor (FIG. 7A). In addition, we assayed the phosphorylation of VEGFR2, a key target of sorafenib in cancer treatment. The expression of p-VEGFR2 (Tyr1175) was decreased in PLC5 cells treated with sorafenib whereas SC-1 did not have significant effect (FIG. 7B). These data suggest that SC-1 derived from sorafenib does not affect kinase inhibition.

Figure 8:
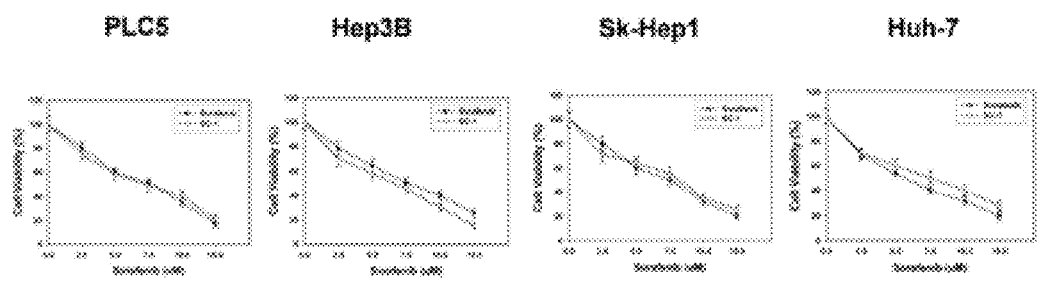
FIG. 8 shows (A) the dose-escalation effects of sorafenib and SC-1 on cell viability in four HCC cell lines, wherein cells were exposed to sorafenib or SC-1 at the indicated doses for 72 h and cell viability was assessed by MTT assay; and the dose-escalation effects of sorafenib and SC-1 on apoptosis in four HCC cell lines, wherein Cells were exposed to sorafenib or SC-1 at the indicated doses for 24 h, and cell lysates were analyzed by flowcytometry (B), or cell death ELISA (C). Points, mean; bars, SD (n=6).
Figure 8:
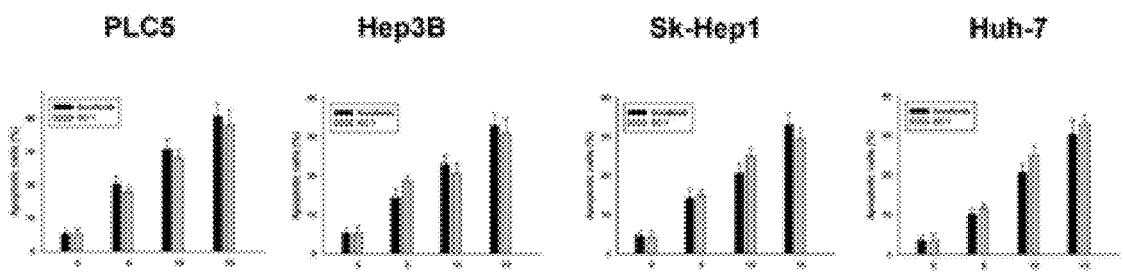
Figure 8:
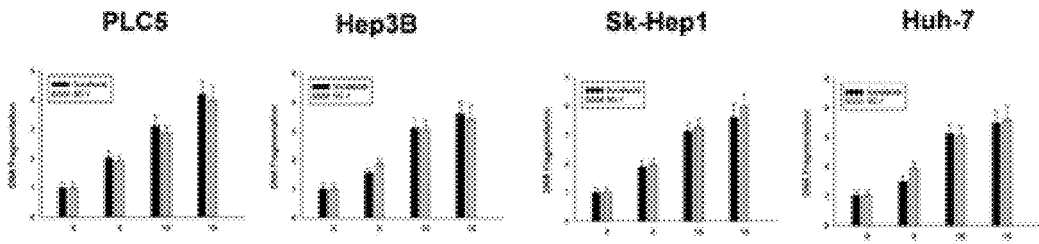

Next, we examined the anti-proliferation effects of sorafenib and SC-1. Both SC-1 and sorafenib decreased the viability of various HCC cells including PLC5, SK-Hep1, Huh7, and Hep3B in a dose-dependent manner (FIG. 8A). In addition, HCC cells treated with SC-1 or sorafenib showed a significant increase in sub-G1 phase population after 24 h exposure (FIG. 8B). Both drugs induced significant apoptotic cell death as detected by the induction of DNA fragmentation in SC-1 or sorafenib-treated HCC cells (FIG. 8C). These data indicate that SC-1 has a significant effect on apoptosis and as potent as sorafenib in inhibiting HCC cell growth even though SC-1 does not have the ability to block kinase activity, suggesting that the mechanism by which sorafenib induces apoptosis in HCC may not be related to its kinase inhibition activity.

2.2.5. STAT3 is a Vital to the Sensitizing Effect of Sorafenib and SC-1 in HCC Cell Lines.

Figure 9:
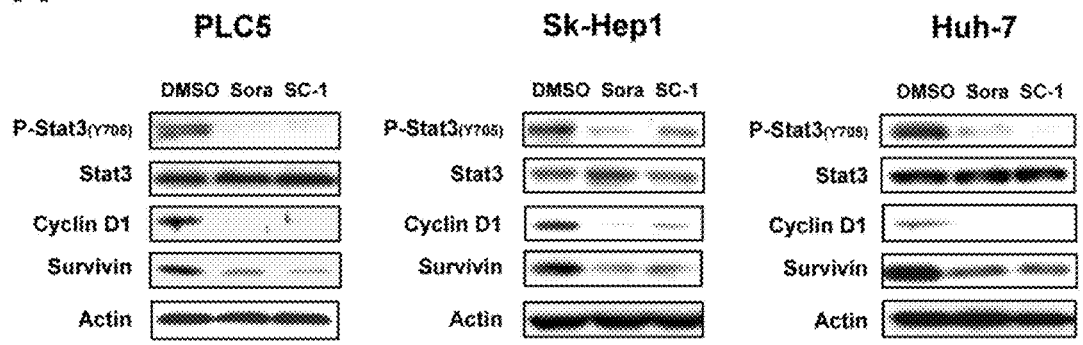
FIG. 9 shows (A) the effects of sorafenib or SC-1 on STAT3-related proteins, wherein cells were treated with sorafenib or SC-1 at 10 μM for 24 h; (B) the dose-escalation effects of sorafenib or SC-1 on phospho-STAT3 in PLC5 cells, wherein cells were treated with drugs at the indicated concentrations for 24 h; (C) the effects of sorafenib and SC-1 on STAT3 activity (left, Phospho-STAT3 ELISA; Right, luciferase reporter assay of STAT3), wherein cells were treated with sorafenib or SC-1 at 10 μM for 24 hs and phospho-STAT3 ELISA or luciferase activity was measured; (D) the protective effects of STAT3 on apoptosis induced by sorafenib in PLC5 cells, wherein cells (wild type or ectopic expression of STAT3) were exposed to sorafenib or SC-1 at 10 μM for 24 h, and apoptotic cells were analyzed by flow cytometry. Columns, mean; bars, SD (n=3). *P<0.05.
Figure 9:
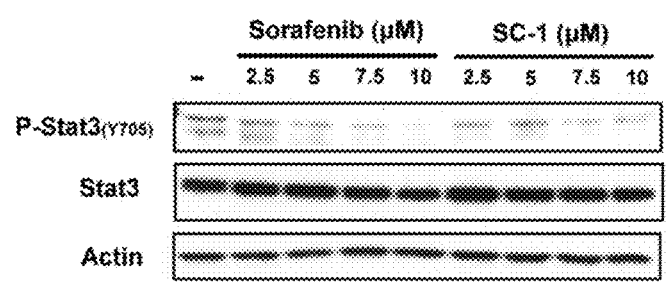
Figure 9:
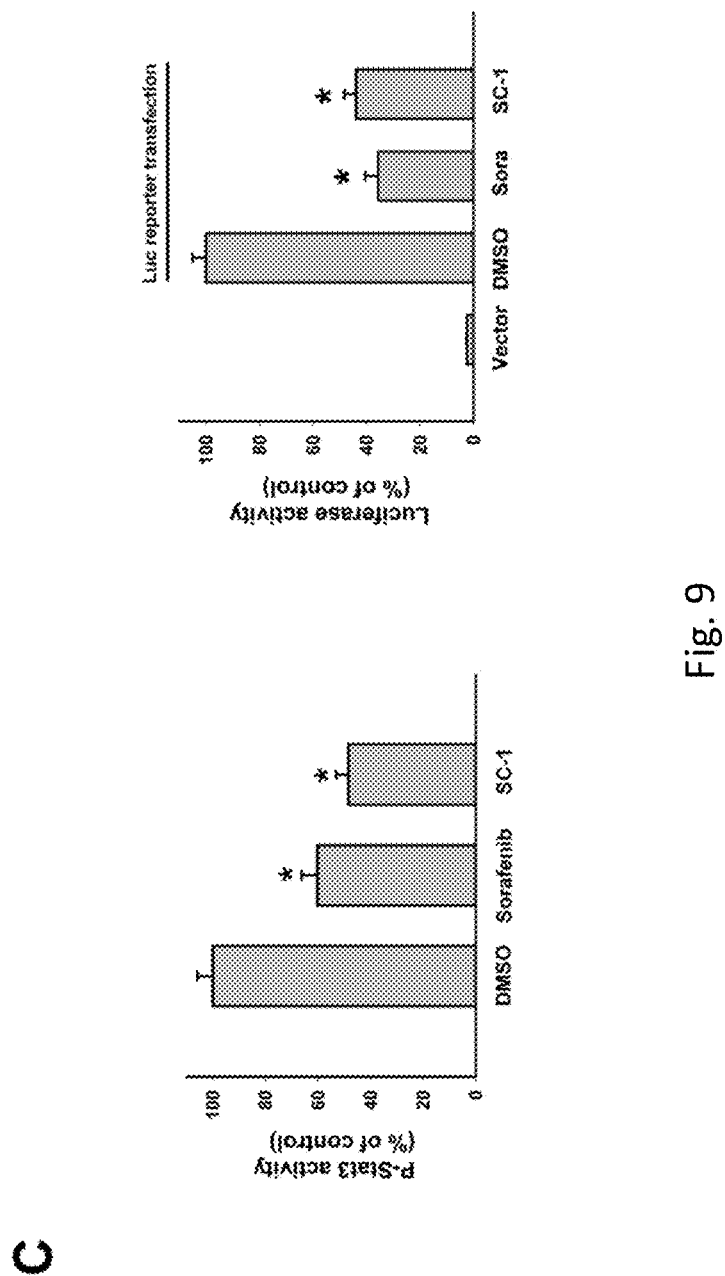
Figure 9:
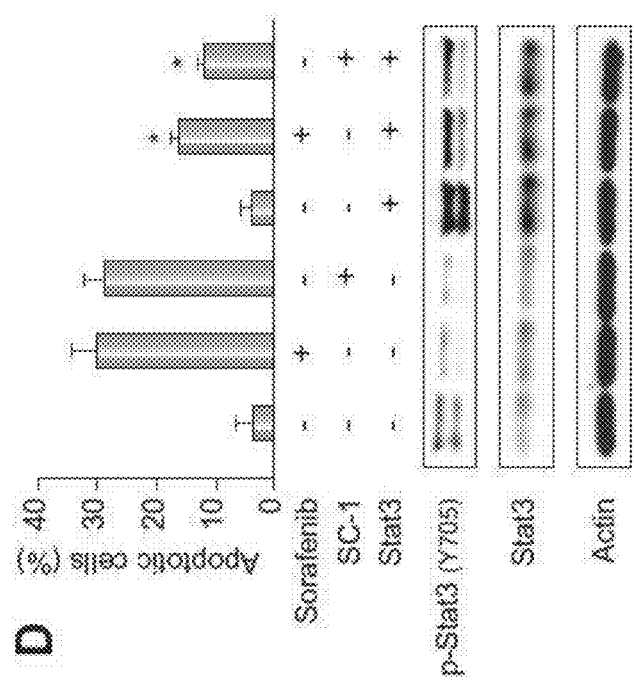

To verify whether down-regulation of p-STAT3 is dependent on the kinase inhibition of sorafenib, we further assayed the STAT3-related signaling pathway in SC-1-treated HCC cells. Given the fact that STAT3 was down-regulated by sorafenib and resulted in the induction of cell death, apoptotic related molecules including Mcl-1, cyclinD1, and survivin were examined. We found that suppression of p-STAT3 plays a role in mediating SC-1-induced or sorafenib-induced cell death. SC-1 reduced the expression of STAT3-related proteins in HCC cells. The phosphorylation of STAT3 at tyrosine 705 is critical for STAT3 transactivation. SC-1 as well as sorafenib down-regulated p-STAT3 at Y705 residue and suppressed Mcl-1 and cyclin D1 in all tested HCC cell lines including PLC5, Huh7, and Sk-Hep1 (FIG. 9A). Notably, total STAT3 protein was not affected by sorafenib and SC-1 (FIG. 9A). Moreover, SC-1 and sorafenib down-regulated p-STAT3 in a dose- and time-dependent manner (FIG. 9B). These data further suggest that sorafenib inhibited STAT3 by a kinase-independent mechanism.

We also assayed the activation status of p-STAT3 by STAT3 ELISA. Twenty-four hours before exposure to sorafenib or SC-1, Sk-Hep1 cells were pre-treated with recombinant IL-6 to mimic high expression level of STAT3 and then were treated with SC-1 or sorafenib for another 24 hours under the presence of IL-6. SC-1 or sorafenib-treated cell extracts were incubated with antibody against phosphorylated STAT3 at Y705. The ELISA results showed that sorafenib as well as SC-1 decreased the activity of p-STAT3 significantly (FIG. 9C, left). To evaluate the transcriptional activity, STAT3-binding region was cloned into Luc reporter. We found that transcription activity of STAT3 was significantly decreased in the presence of sorafenib or SC-1 (FIG. 9C, right). The firefly luciferase activity was evaluated and normalized by *Renilla luciferase*. These results showed that both sorafenib and SC-1 potently reduced the level of phosphorylation of STAT3 through the suppression of transcription. We then established STAT3-overexpressed stable clone of HCC cells to validate the effect of sorafenib in HCC. As shown in FIG. 9D, both sorafenib-induced and SC-1-induced apoptosis were abolished in STAT3-overexpressed HCC cells as evidenced by sub-G1 analysis, suggesting that STAT3 is a major mediator of sorafenib- and SC-1-induced apoptosis.

2.2.6. SHP-1 Phosphatase Plays a Role in the Effect of Sorafenib and SC-1 on Phospho-STAT3 and Apoptosis.

Figure 10:
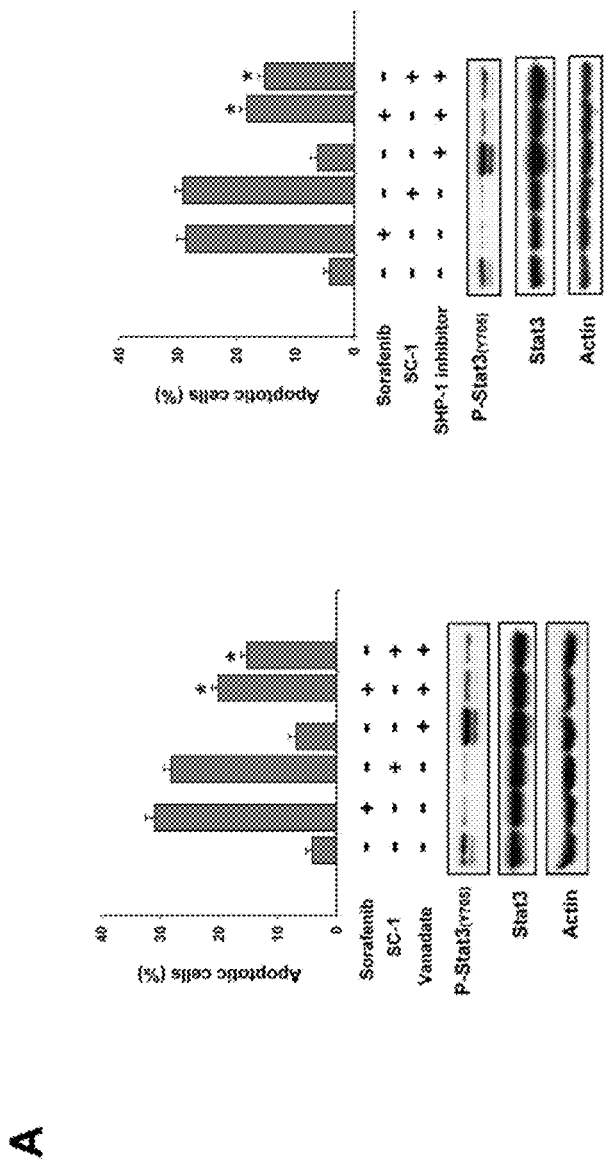
FIG. 10 shows inhibition of SHP-1 reverses effects of sorafenib and SC-1 on phospho-STAT3 and apoptosis. A, left, vanadate, a non-specific phosphatase inhibitor. Right, specific SHP-1 inhibitor. Columns, mean; bars, SD (n=3). *P<0.05. B, left, silencing SHP-1 by siRNA reduces effects of sorafenib or SC-1 on p-STAT3 in HCC cells. PLC5 cells were transfected with control siRNA or SHP-1 siRNA for 24 h then treated with sorafenib or SC-1 for another 24 h. Middle, the activity of SHP-1 in PLC5 cells. Columns, mean; bars, SD (n=3). *P<0.05. Right, effects of sorafenib or SC-1 on protein interactions between SHP-1 and STAT3. PLC5 cells were treated with sorafenib or SC-1 at 10 μM for 24 hours. C, knock-down of SHP-2 does not affect the effects of sorafenib or SC-1 on p-STAT3 and apoptosis. D, knock-down of PTP-1B does not affect effects of sorafenib on p-STAT3 and apoptosis. PLC5 cells were transfected with control siRNA or SHP-2 siRNA or PTP-1B siRNA for 24 h then treated with sorafenib or SC-1 at 10 μM for 24 h.
Figure 10:
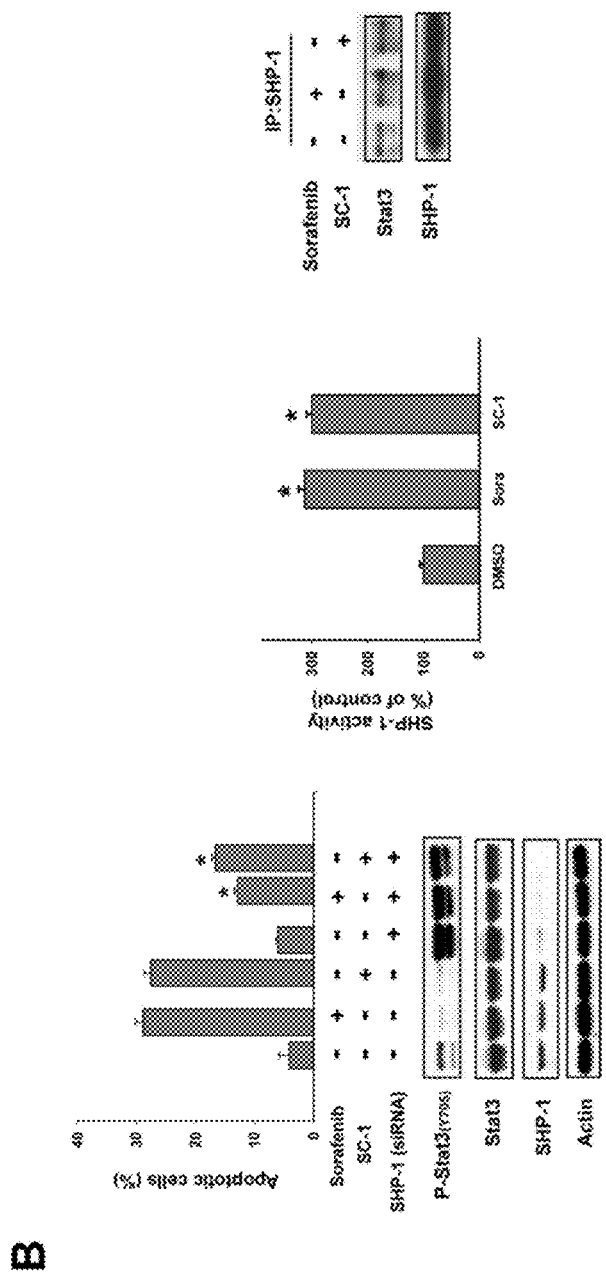
Figure 10:
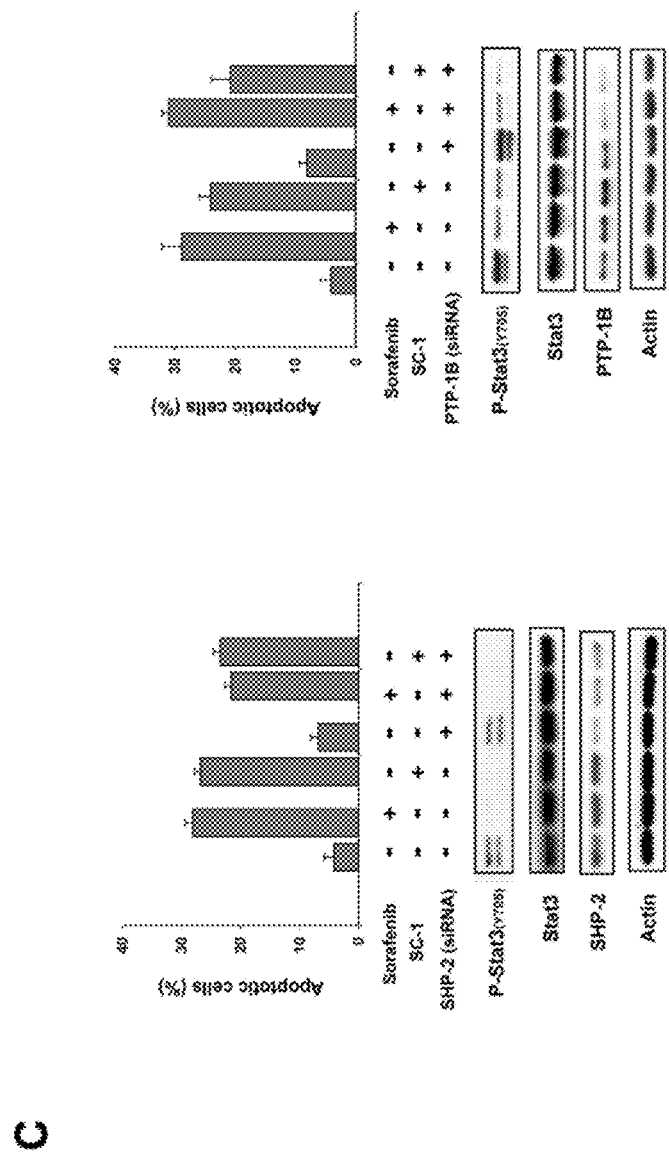

To further study how sorafenib inhibits STAT3 in HCC, we examined several protein phosphatases which may involved in regulating p-STAT3. Our results showed that sodium vanadate, a general phosphatase inhibitor, decreased apoptosis and increased p-STAT3 (FIG. 10A, left). These data suggest that sorafenib and SC-1 may affect p-STAT3 by targeting STAT3-related protein phosphatases. Furthermore, we found that SHP-1 phosphatase-specific inhibitor reversed sorafenib-induced cell death and inhibition of p-STAT3 (FIG. 10A, right). To further verify the role of SHP-1 in SC-1 and sorafenib-induced inhibition of p-STAT3, we applied siRNA specific to SHP-1 to examine the influence of sorafenib and SC-1. We found that silencing of SHP-1 reversed sorafenib- or SC-1-induced apoptosis and inhibition of p-STAT3 (FIG. 10B, left). In addition, both sorafenib and SC-1 increased SHP-1 activity up to 3-fold in comparison with control cells (P<0.05) (FIG. 10B, middle). Sorafenib or SC-1-treated PLC5 cells were immunoprecipitated by SHP-1 specific antibody, and then SHP-1-containing complex underwent fluorescence-based phospho-group assay. Notably, neither sorafenib nor SC-1 affected the interaction of STAT3 and SHP-1 as evidenced by SHP-1 immunoprecipitation (FIG. 10B, right). These data suggest that sorafenib induced cell death through SHP-1-dependent STAT3 inactivation.

In addition to SHP-1, other phosphatases such as SHP-2 and PTP-1B, have been reported to regulate p-STAT3. As shown in FIG. 10C, the effects of sorafenib on apoptosis and p-STAT3 were not reversed by silencing SHP-2 or PTP-1B, suggesting that neither SHP-2 nor PTP-1B played a role in mediating the effect of sorafenis or SC-1 on p-STAT3.

2.2.7. SC-1 Down-Regulates p-STAT3 and Induces Apoptosis in HUVEC Cells.

Figure 11:
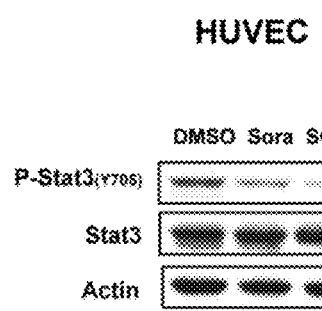
FIG. 11 shows that SC-1 down-regulates p-STAT3 and induces apoptosis in HUVEC cells. A, effects of sorafenib or SC-1 on p-STAT3 (left) and apoptosis (right) in HUVEC cells. Cells were exposed to sorafenib or SC-1 at 10 μM for 24 h. Apoptotic cells were assayed by flow cytometry (sub-G1). B, effects of SC-1 on TRAIL sensitization in HCC. PLC5 cells were treated with SC-1 (10 μM) and/or TRAIL (100 ng/ml) for 24 h. C, silencing Raf-1 does not affect the effects of the drugs on p-STAT3. PLC5 cells were transfected with control siRNA or Raf-1 siRNA for 24 h then treated with sorafenib or SC-1 at 10 μM for 24 h. D, effect of sorafenib and SC-1 on JAK2 activity. PLC5 cells were exposed to sorafenib or SC-1 at 10 μM for 24 h. Points, mean; bars, SD (n=6). E, effects of sorafenib and SC-1 on SOCS-1 and SOCS-3. Sk-Hep1 cells were pre-treated with IL-6 for 24 h then were treated with sorafenib or SC-1 at the indicated doses for another 24 h in the presence of IL-6. F, effects of STAT-C on apoptosis induced by SC-1 in PLC5 cells. Cells (wild type or ectopic expression of STAT3-C) were exposed to sorafenib or SC-1 at 10 μM for 24 h. G, effects of sorafenib and SC-1 on SHP-1. Columns, mean; bars, SD (n=3). *P<0.05.
Figure 11:
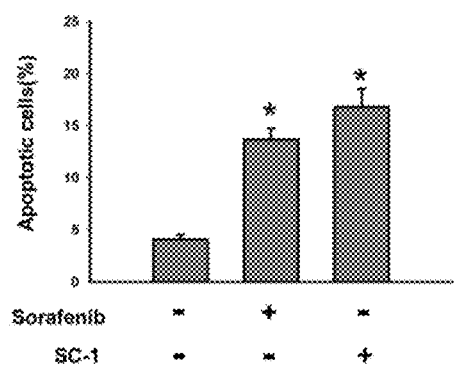
Figure 11:
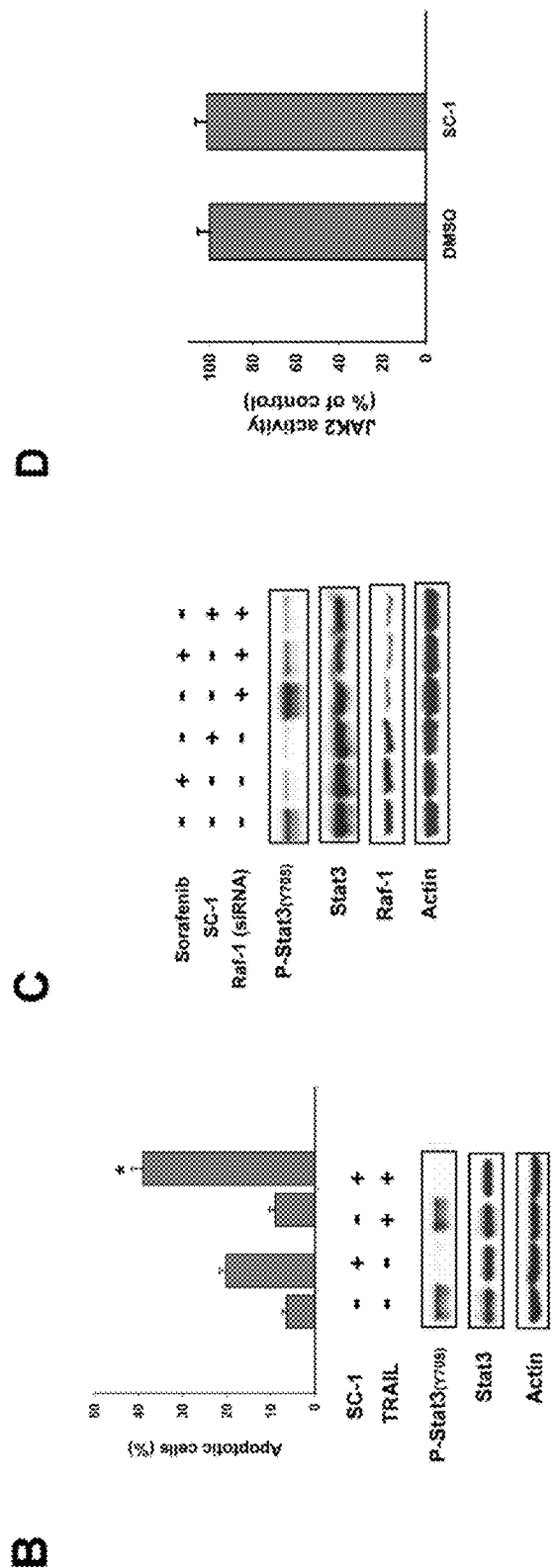
Figure 11:
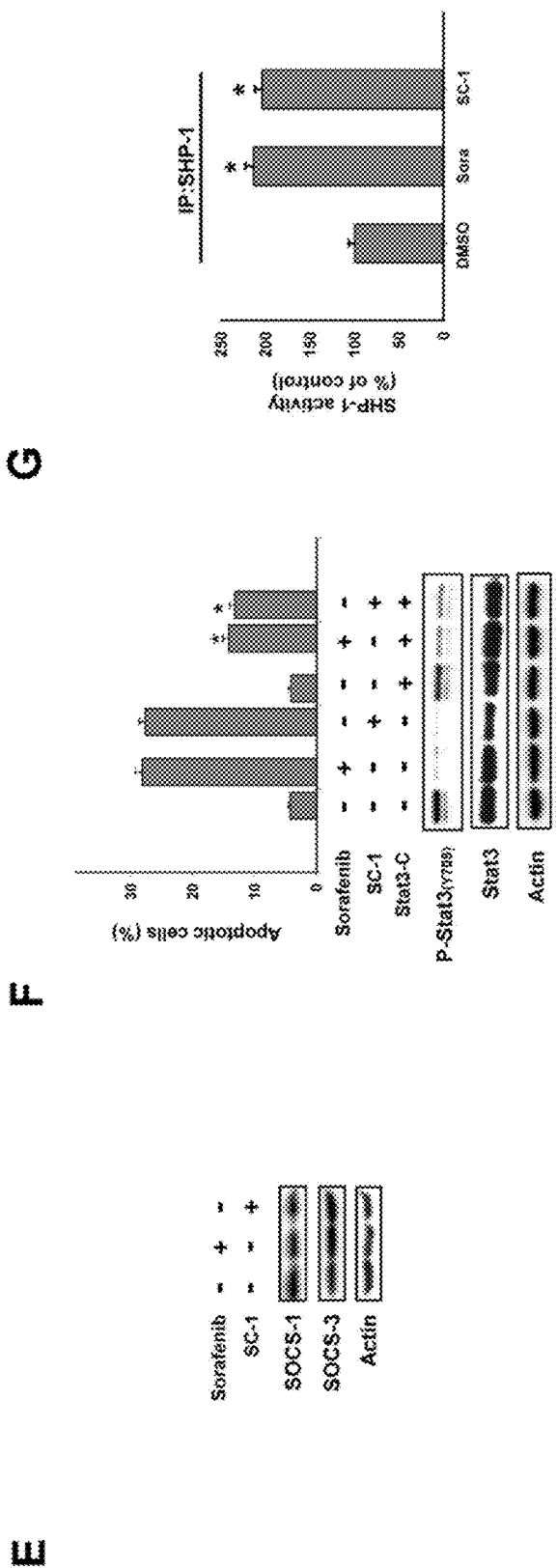

To clarify the effect of sorafenib on p-VEGFR2, a key target of sorafenib in cancer treatment, we examined the effect of sorafenib and SC-1 in HUVEC cells. As shown in FIG. 11A, left, sorafenib and SC-1 both down-regulated p-STAT3 in HUVEC cells and induced significant apoptotic cell death in HCC (P<0.05). Notably, sorafenib but not SC-1 down-regulated the phosphorylation of VEGFR in HUVEC cells (FIG. 7A, middle). These results indicate that neither Raf-1 nor VEGFR mediates the effect of sorafenib on apoptosis and p-STAT3.

Previous study has also suggested that Mcl-1 is crucial in mediating the effect of sorafenib on TRAIL-sensitization. Interestingly, our data showed that SC-1 also showed similar enhancement of TRAIL-induced apoptosis in HCC by the down-regulation of p-STAT3 (FIG. 11B). To further investigate whether inhibition of p-STAT3 by sorafenib is associated with Raf-1, we knocked down Raf-1 by using small interference RNA. Silencing Raf-1 did not affect the effects of sorafenib or SC-1 on p-STAT3 (FIG. 11C), indicating that Raf-1 does not mediate the effect of sorafenib on p-STAT3. Notably, neither sorafenib nor SC-1 altered the kinase activity of JAK2 (FIG. 11D), suggesting that JAK2 does not mediate effects of both compounds on p-STAT3. In addition, our data showed that sorafenib and SC-1 did not affect the protein levels of SOCS-1 and SOCS-3 (FIG. 11E). Interestingly, HCC cells with constitutively active STAT-3 (STAT3-C) were not completely resistant to SC-1 (FIG. 11F). As SC-1 enhanced the activity of SHP-1 (FIG. 11B, middle), our data suggest that besides STAT-3, other SHP-1-related molecules may also play a role in mediating the effect of SC-1. To examine whether sorafenib or SC-1 targets SHP-1 directly, PLC5 cells were immunoprecipitated with SHP-1 antibody then incubated with sorafenib or SC-1 for 6 hours. As shown in FIG. 11G, sorafenib and SC-1 increase the activity of SHP-1 in these lysates, suggesting that sorafenib and SC-1 targets SHP-1 directly.

2.2.8. Therapeutic Evaluation of Effect of SC-1 and Sorafenib on Huh7-Bearing Mice.

Figure 12:
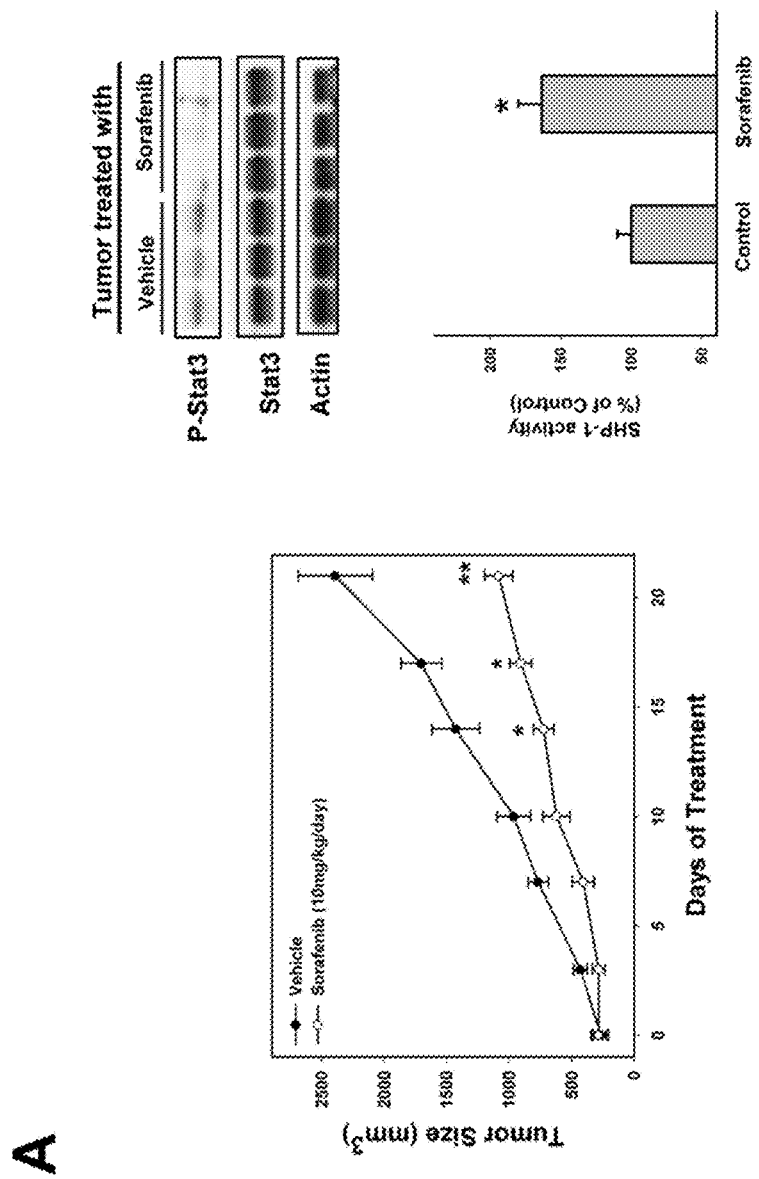
FIG. 12 shows in vivo effect of sorafenib and SC-1 on Huh-7 xeonograft nude mice A, sorafenib shows antitumor effect on Huh-7 tumors. Left, points, mean (n=6); bars, SE. *, P<0.05; **, P<0.01. Right Upper, western blot analysis of p-STAT3 and STAT3 in Huh-7 tumors. Right Lower, the activity of SHP-1 in Huh-7 tumors. B, SC-1 shows a significant antitumor effect on Huh-7 tumors. Left, points, mean (n=6); bars, SE. Right Upper, western blot analysis of p-STAT3 and STAT3 in Huh-7 tumors. Right Lower, the activity of SHP-1 in Huh-7 tumors.
Figure 12:
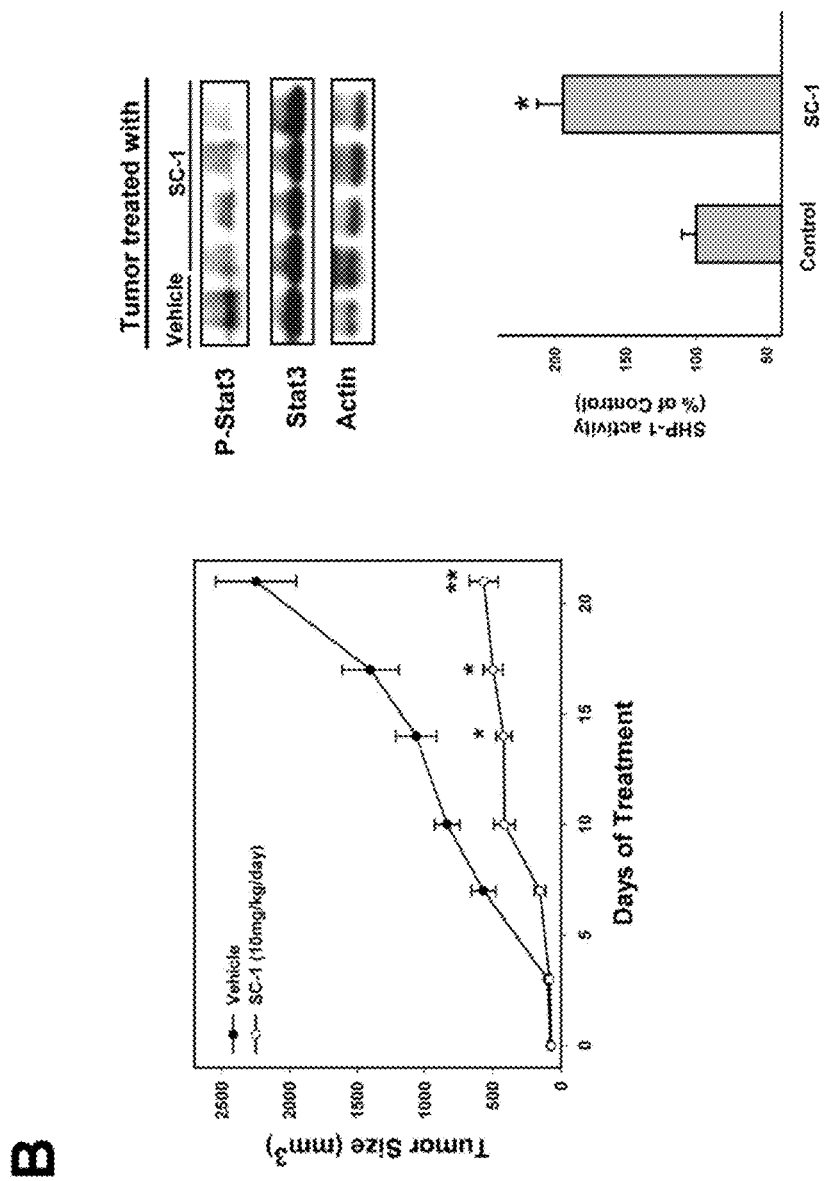

To verify the therapeutic effect of SC-1, we further applied SC-1 to HCC xenograft to evaluate its significance in vivo. First, Huh7-bearing mice received daily treatment with vehicle or sorafenib at the dose of 10 mg/kg/day orally. Sorafenib treatment significantly inhibited Huh7 xenograft tumor growth and sorafenib-treated animals had a tumor-size of less than half that of control mice (FIG. 12A, left). There were no apparent differences in body weight or toxicity in any mice (data not shown). In addition, tumor extract from vehicle and sorafenib-treated mice were immunoblotted for p-STAT3. p-STAT3 was down-regulated in sorafenib-treated tumor (FIG. 12A, right). p-STAT3/STAT3 was observed in the homogenates of three representative Huh7 tumors. Furthermore, we examined SHP-1 activity in sorafenib-treated Huh7 xenograft. Sorafenib treated tumor showed significant induction of SHP-1 activity in vivo (FIG. 12A, right). Taken together, these results confirmed that sorafenib could increase SHP-1 activity to repress p-STAT3 involved in tumor inhibition in the HCC xenograft model.

In addition, treatment with SC-1 had a strong inhibitory effect (P<0.05) and tumor size in this group was only 25% that of vehicle-treated mice at the end of treatment (FIG. 12B, left) Immunoblot for p-STAT3 and SHP-1 activity assay were also performed on a tumor sample from SC-1-treated animals. Interestingly, SC-1 induced significant rising of SHP-1 activity and down regulated p-STAT3 (FIG. 12B, right). These data indicate that SC-1, a SHP-1 agonist and a STAT3 inhibitor, exhibit therapeutic effects in inhibiting tumor growth.

2.2.9. Inhibition of Cancer Cell Growth

Figure 13:
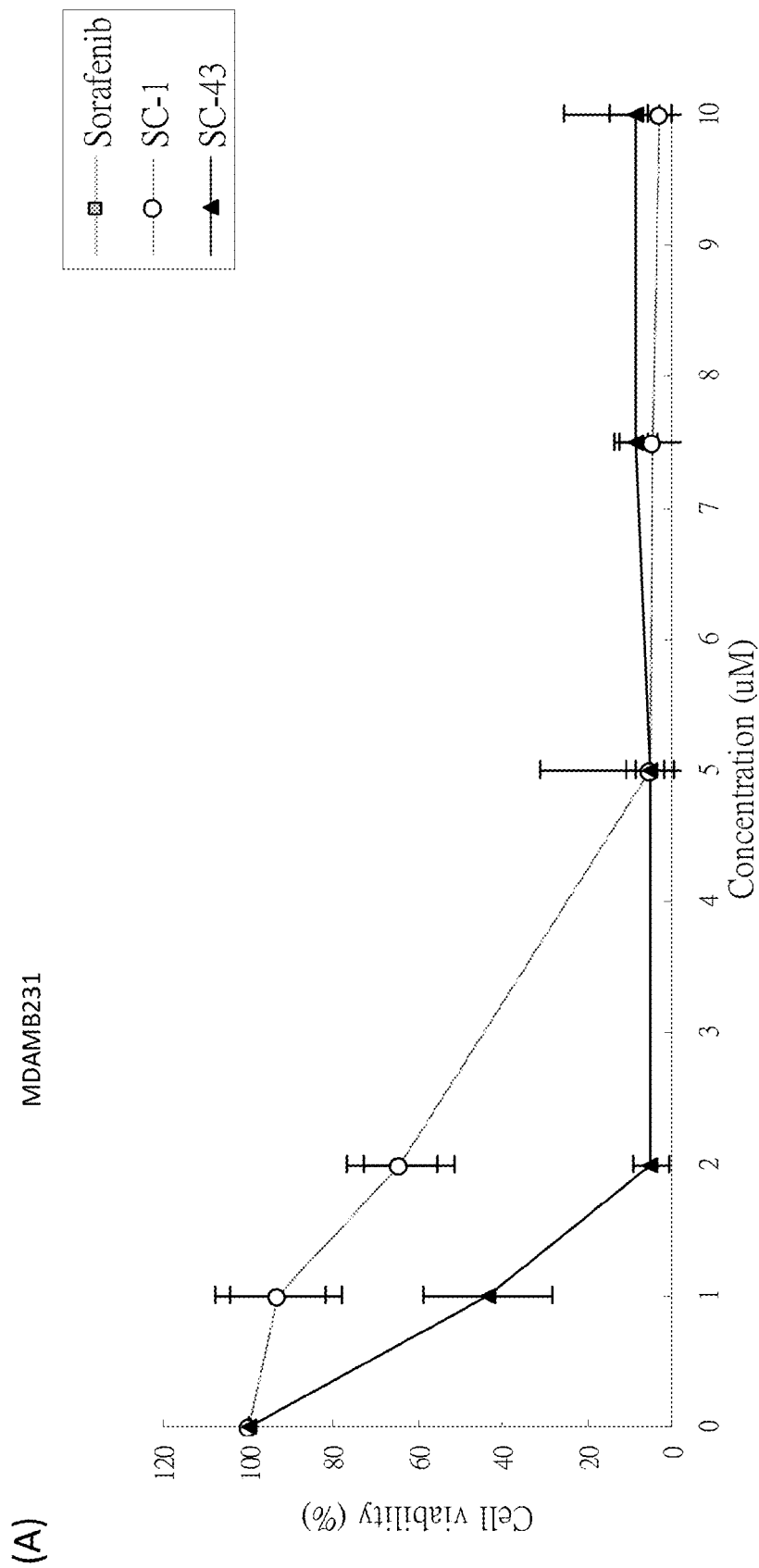
FIG. 13 shows the anti-proliferation effects of SC-1 and SC-43 in various cancer cell lines, including breast cancer cell lines (A) MDAMB231, (B) MDAMB468 and (C) MCF-7, and leukemia cancer cell lines (D) HL-60, (E) KG-1, and (F) ML-1.
Figure 13:
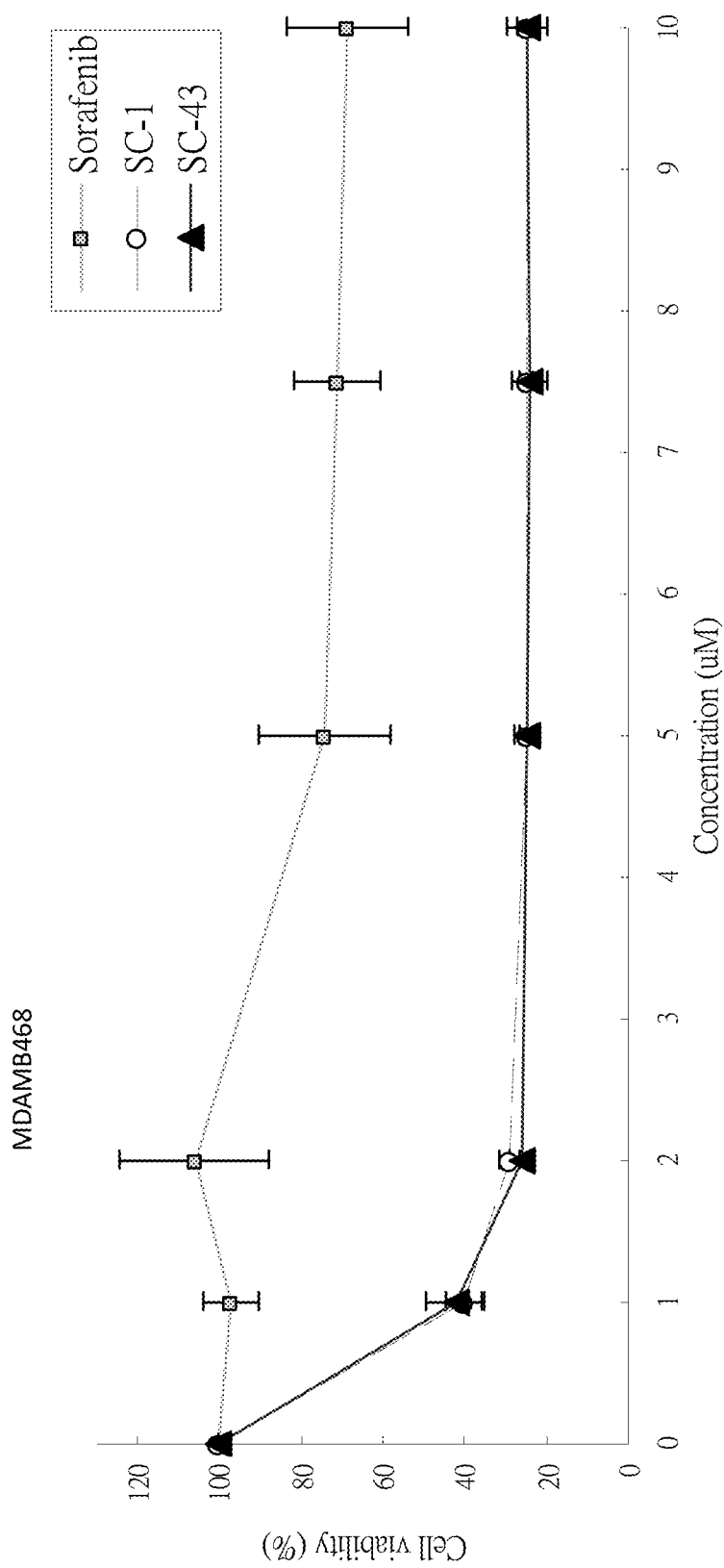
Figure 13:
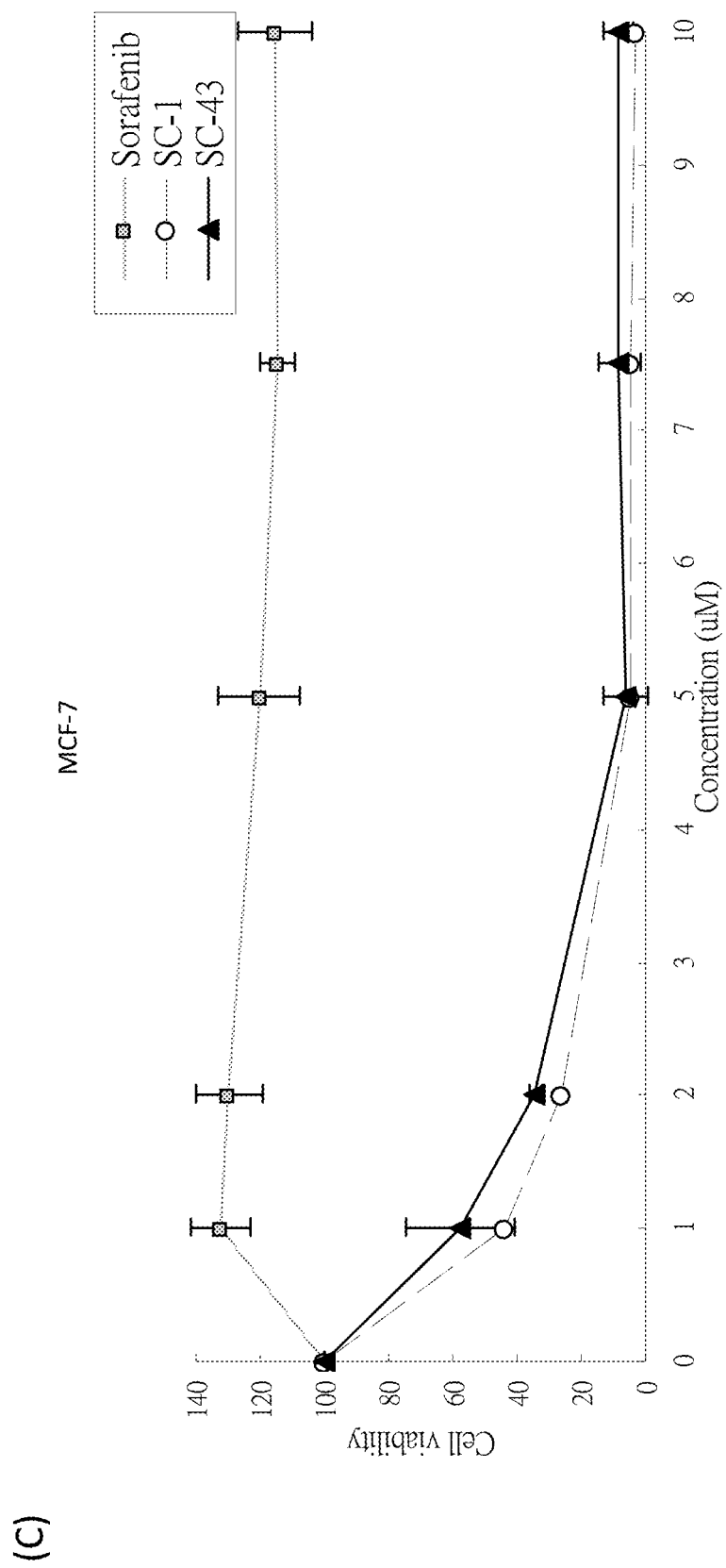
Figure 13:
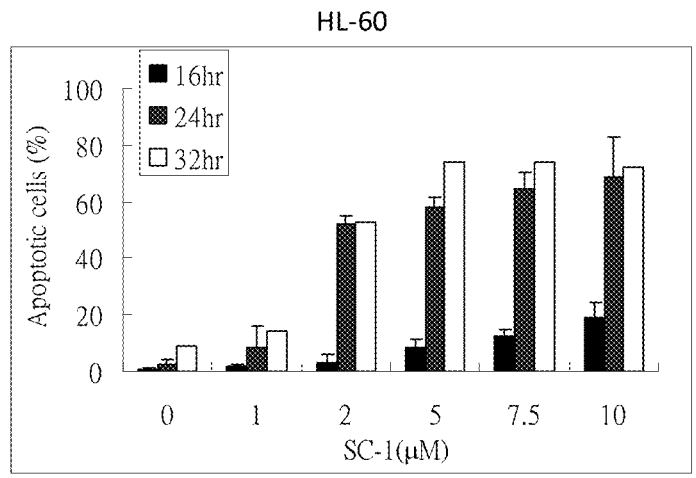
Figure 13:
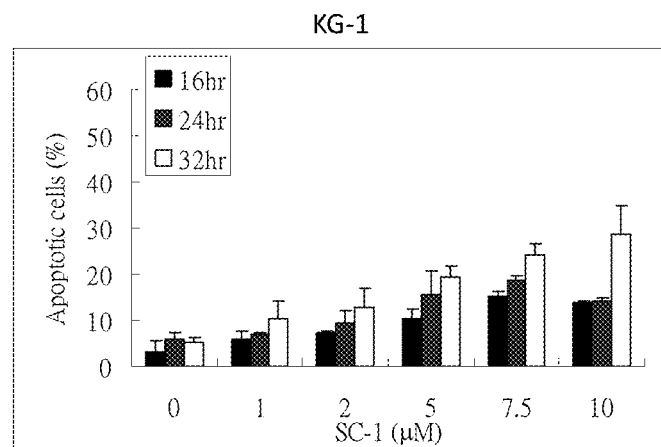
Figure 13:
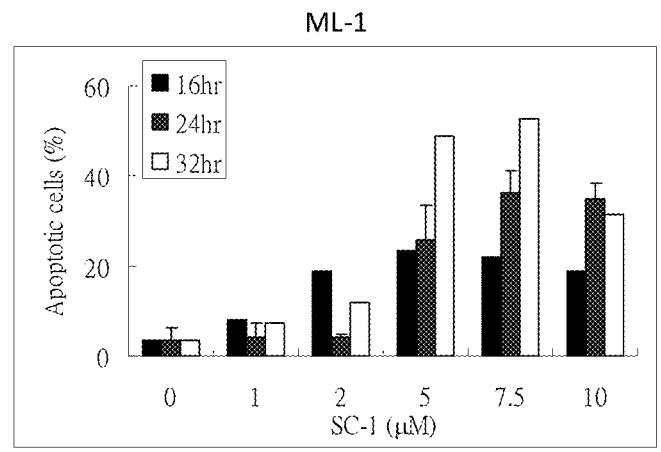

We also examined the effects of SC-1 and SC-43 in other cancer cell lines, including breast cancer cell lines e.g. MDAMB231, MDAMB468, MCF-7, and leukemia cancer cell lines e.g. HL-60, KG-1 and ML-1. FIG. 13 shows the results. These data show that the compounds of the invention are effective in inhibiting the growth of cancer cells.

2.2.10 Anti-Cancer Effects in HCC Cells

Figure 14:
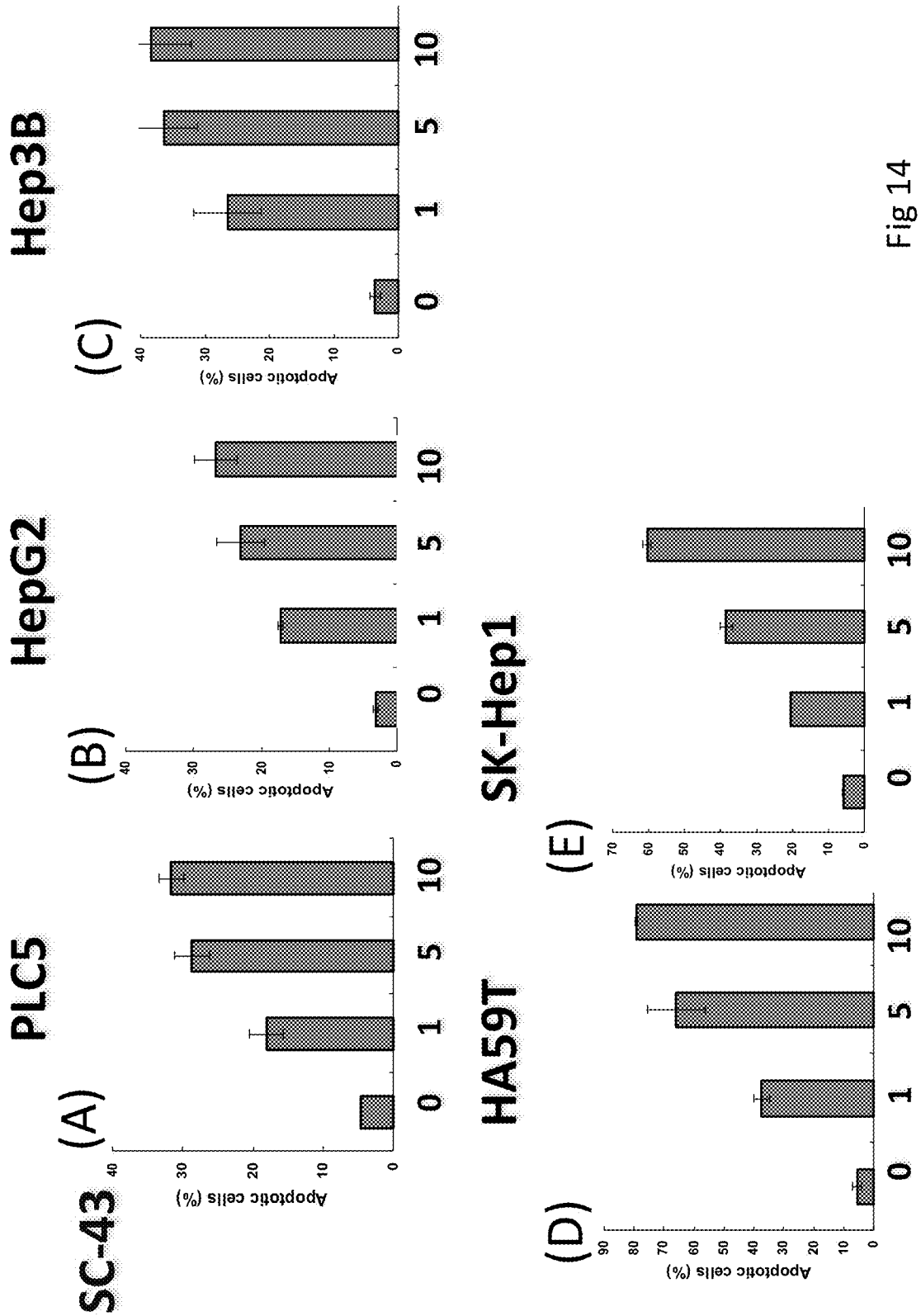
FIG. 14 shows that Sorafenib derivatives induce significant apoptosis in a dose-dependent manner, where (A), (B), (C), (D) and (E) refer to SC-43 for PLC5, HepG2, Hep3B, HA59T and SK-Hep1 cells, respectively; and (F), (G), (H), (I) and (J) refer to SC-40 for PLC5, HepG2, Hep3B, HA59T and SK-Hep1 cells, respectively. Points, mean; bars, SD (n=6).
Figure 14:
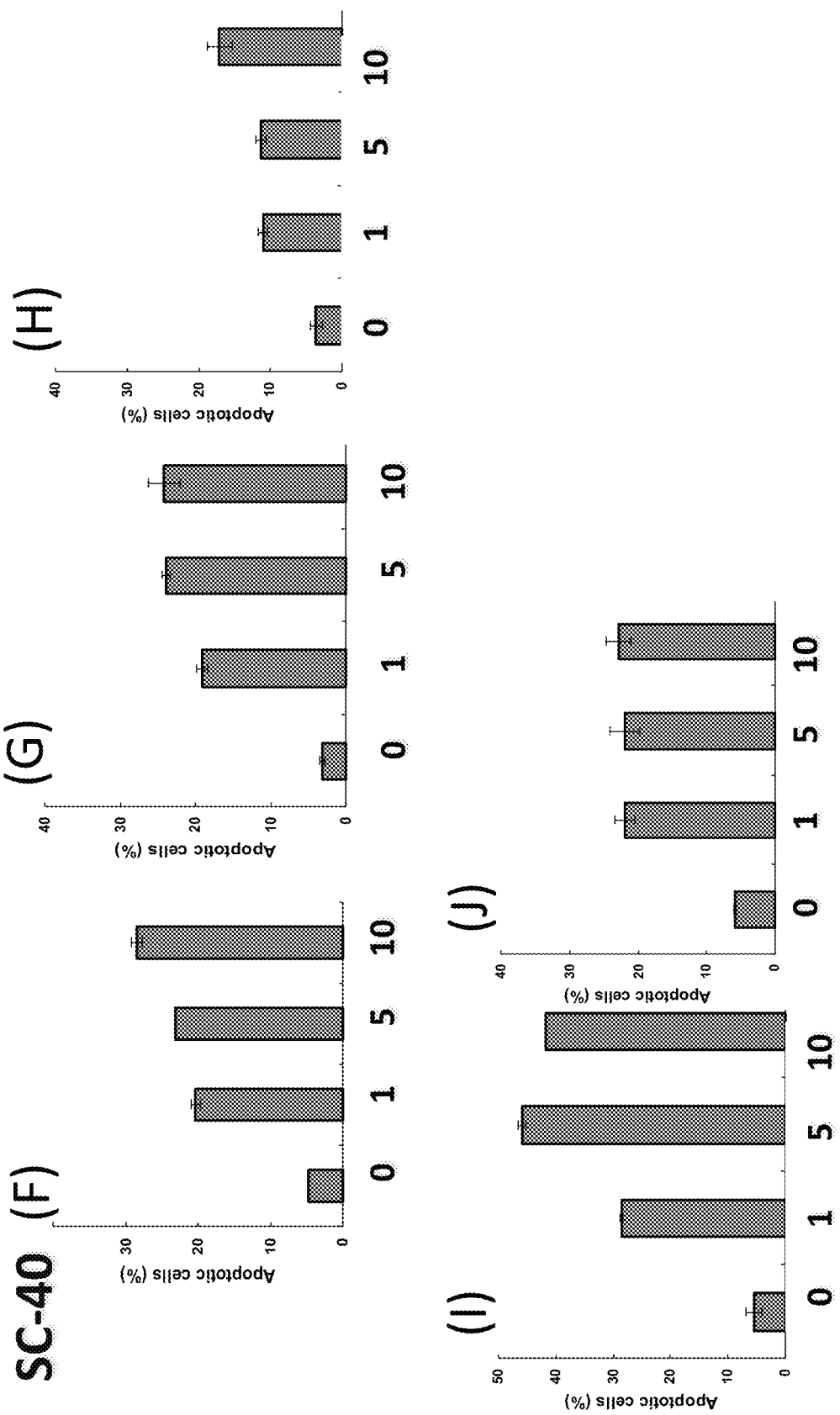

HCC cells were treated with sorafenib derivatives (SC-43 or SC-40) at the indicated dose for 24 h. Collected cells were fixed in 75% Ethanol and stained with 20 ug/ml Propidium Iodide (PI). Sub-G1 analysis was performed by flow-cytometry. FIG. 14 shows that SC-43 and SC-40, sorafenib derivatives, show significant anti-cancer effects in HCC cells, (A), (B), (C), (D) and (E) refer to SC-43 for PLC5, HepG2, Hep3B, HA59T and SK-Hep1 cells, respectively; and (F), (G), (H), (I) and (J) refer to SC-40 for PLC5, HepG2, Hep3B, HA59T and SK-Hep1 cells, respectively. Points, mean; bars, SD (n=6).

2.2.11 Effects of Sorafenib or SC-43 on STAT3-Related Proteins.

Figure 15:
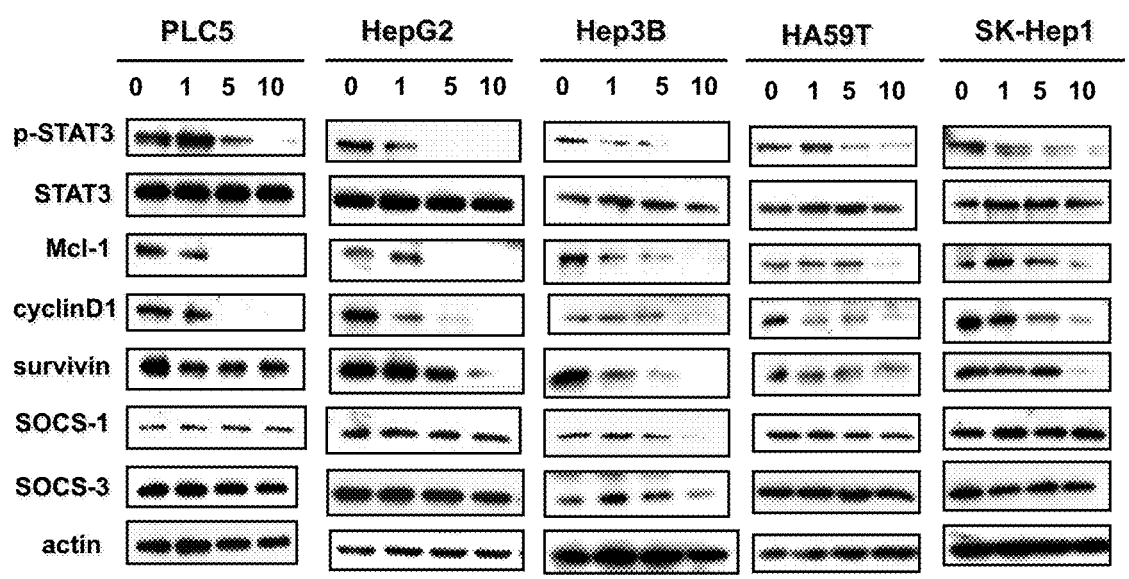
FIG. 15 shows that that SC-43 down-regulates phospho-STAT3-related signaling pathway in HCC cells, including PLC5, HepG2, Hep3B, HA59T and SK-Hep1 cells.

HCC cells treated with SC-43 (10 μM for 24 h) were collected with RIPA lysis buffer. Antibodies for immunoblotting such as cyclin D1 was purchased from Santa Cruz Biotechnology. Other antibodies such as survivin, phospho-STAT3 (Tyr705), STAT3, Mcl-1, SOCS1, and SOCS3 were from Cell Signaling. FIG. 15 shows that SC-43 down-regulates phospho-STAT3-related signaling pathway in HCC.

2.2.12 Effects of Sorafenib or SC-40 on STAT3-Related Proteins.

Figure 16:
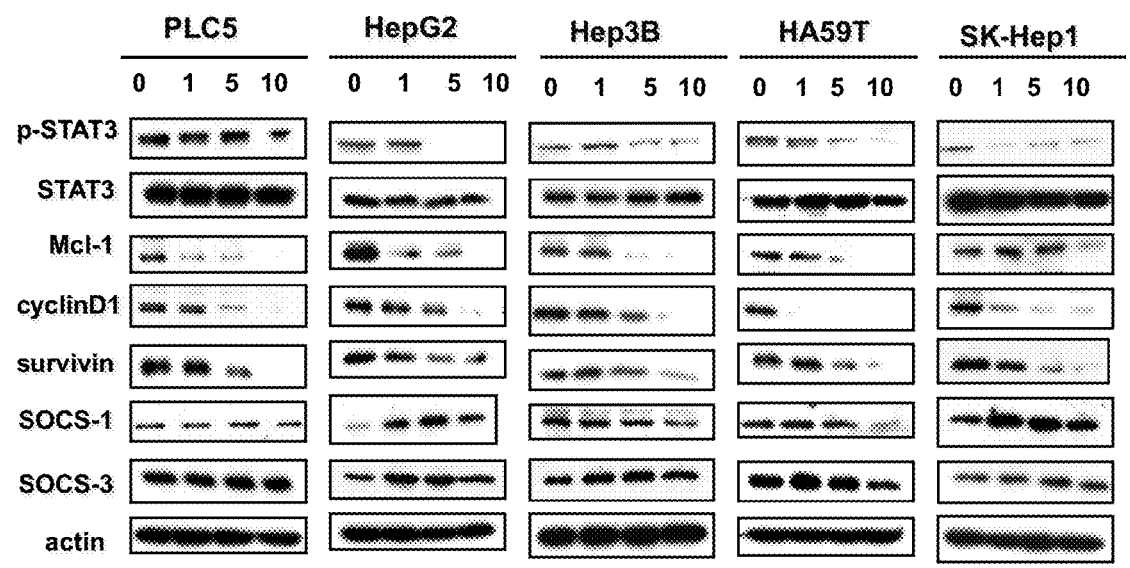
FIG. 16 shows that SC-40 down-regulates phospho-STAT3-related signaling pathway in HCC, cells, including PLC5, HepG2, Hep3B, HA59T and SK-Hep1 cells.

HCC cells treated with SC-40 (10 μM for 24 h) were collected with RIPA lysis buffer. Antibodies for immunoblotting such as cyclin D1 were purchased from Santa Cruz Biotechnology. Other antibodies such as survivin, phospho-STAT3 (Tyr705), STAT3, Mcl-1, SOCS1, and SOCS3 were from Cell Signaling. FIG. 16 shows that SC-40 down-regulates phospho-STAT3-related signaling pathway in HCC.

2.2.13 Effects of Sorafenib or SC-43 on STAT3-Related Proteins

Figure 17:
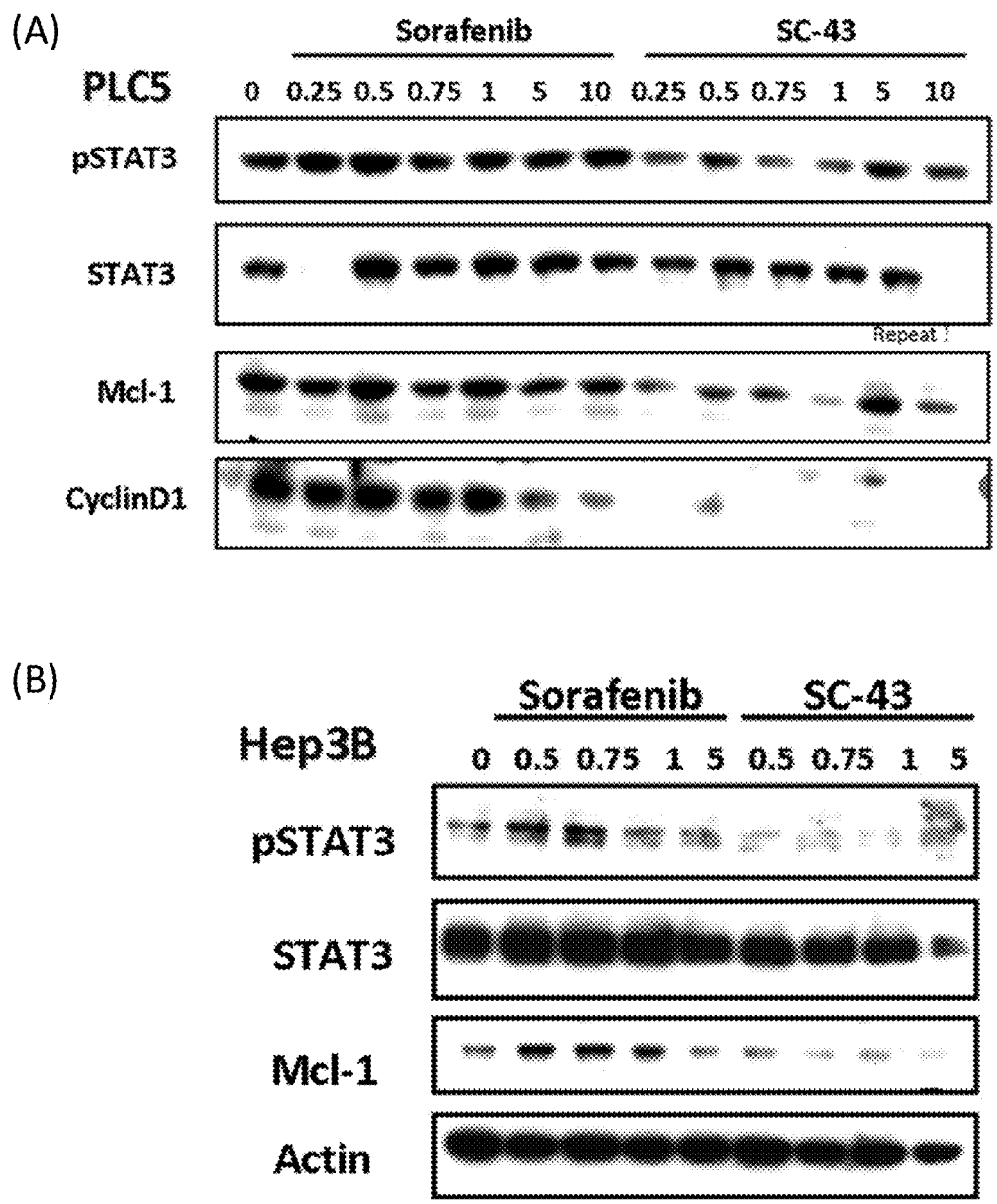
FIG. 17 shows that SC-43 shows better inhibition of p-STAT3-related signaling pathway than sorafenib in HCC cells, (A) PLC5 and (B) Hep 3B.

HCC cells treated with SC-43 (10 μM for 24 h) were collected with RIPA lysis buffer. Antibodies for immunoblotting such as cyclin D1 were purchased from Santa Cruz Biotechnology. Other antibodies such as survivin, phospho-STAT3 (Tyr705), STAT3, and Mcl-1 were from Cell Signaling. FIG. 17 shows that SC-43 shows better inhibition of p-STAT3-related signaling pathway than sorafenib in HCC, (A) PLC5 and (B) Hep 3B. SC-43 shows significant inhibition of p-STAT3-related proteins at low dose treatment than sorafenib.

2.2.14 Effects of SC-43 and SC-40 on STAT3 Activity p-STAT3 activity: PLC5 cells treated with SC derivatives were collected in RIPA buffer and analyzed in p-STAT3 ELISA kit. The assay protocol follows the manufacturer.

STAT3 Reporter Assay:

PLC5 cells were seeded in a 96-well plate.

Cells were pretransfected with STAT3 reporter construct for 24 h and treated with derivatives for another 24 h. The STAT3 Reporter Kit was purchased from SABiosciences.

Figure 18:
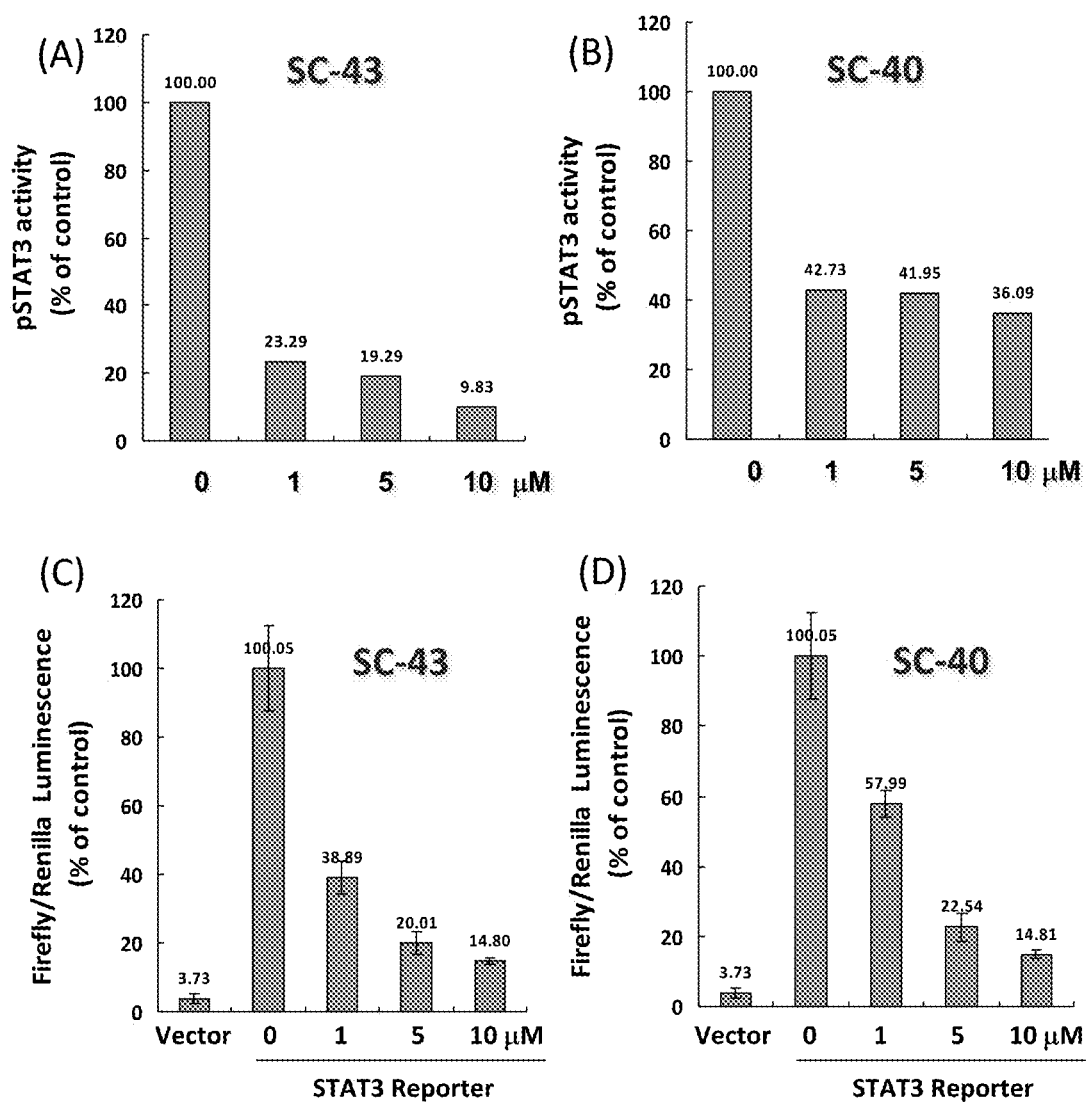
FIG. 18 shows that both SC-43 and SC-40 induce strong inhibition of p-STAT3 activity (A) and (B) p-STAT3 ELISA for SC-43 and SC-40, respectively, and (C) and (D) STAT3 reporter assay for SC-43 and SC-40, respectively.

Cells were treated with SC-43 or SC-40 at 10 µM for 24 h and phospho-STAT3 ELISA or luciferase activity was measured. FIG. 18 shows that both SC-43 and SC-40 induce strong inhibition of p-STAT3 activity, (A) and (B) p-STAT3 ELISA for SC-43 and SC-40, respectively, and (C) and (D) STAT3 reporter assay for SC-43 and SC-40, respectively.

2.2.15 Effects of SC-43/40 on Phosphatase Activity

Figure 19:
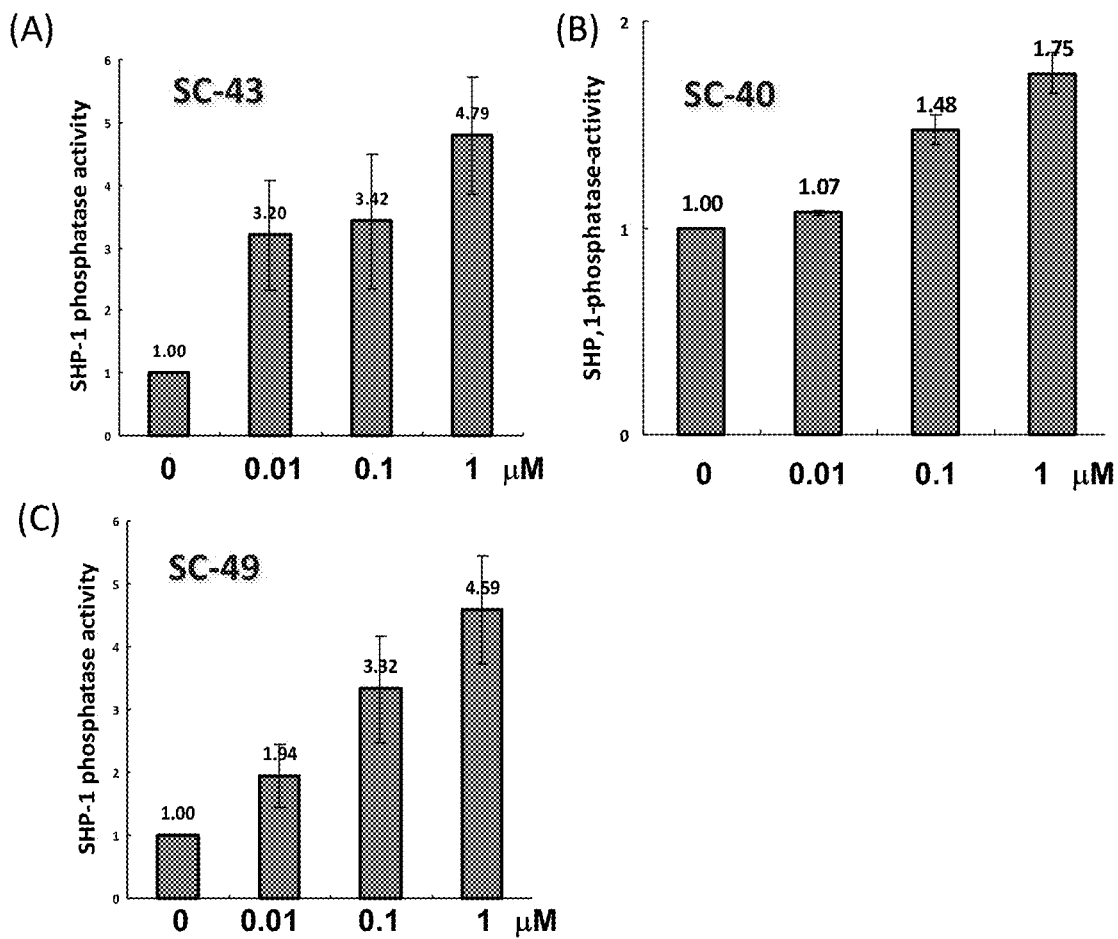
FIG. 19 shows that the SC derivatives increase phosphatase activity of SHP-1 in vitro, (A)SC-43, (B)SC-40, and (C)SC-49.

PLC5 protein extract was incubated with anti-SHP-1 antibody in immunoprecipitation buffer overnight. Protein G Sepharose 4 Fast flow (GE Healthcare Bio-Science) was added to each sample, followed by incubation for 3 hours at 4° C. with rotation. This SHP-1-containing protein extract were further incubated with SC compounds (10 or 100 nmol/L) for 30 min at 4° C. RediPlate 96 EnzChek Tyrosine Phosphatase Assay kit (R-22067) was used for SHP-1 activity assay (Molecular Probes). FIG. 19 shows that the SC derivatives increase phosphatase activity of SHP-1 in vitro, (A)SC-43, (B)SC-40, and (C)SC-49.

2.2.16 Effects of SC Derivatives on Phosphatase Activity in Recombinant SHP-1

Figure 20:
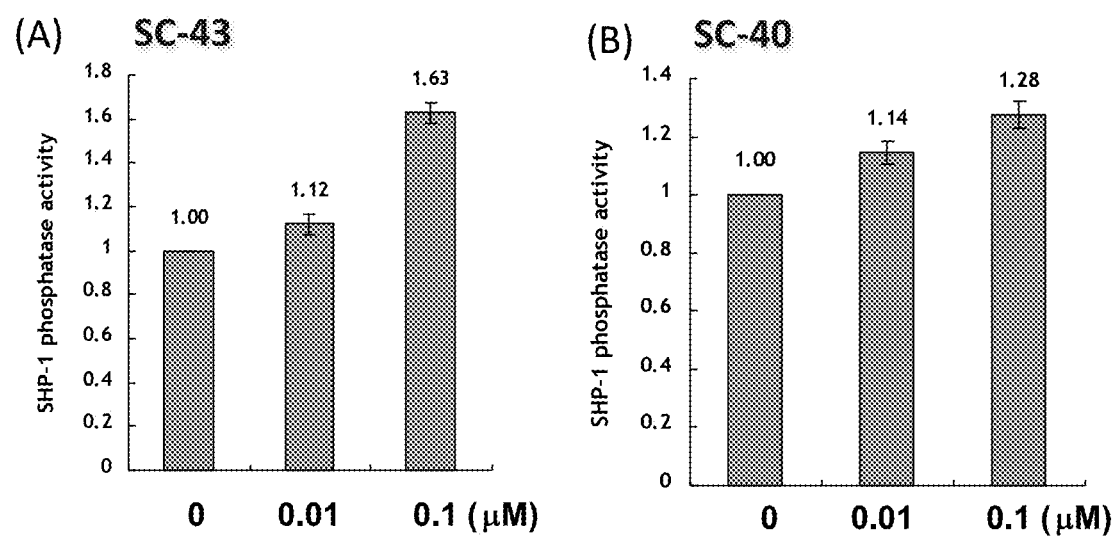
FIG. 20 shows that the SC derivatives increase phosphatase activity of SHP-1 in vitro, (A)SC-43 and (B)SC-40.

RediPlate 96 EnzChek Tyrosine Phosphatase Assay kit (R-22067) was used for SHP-1 activity assay (Molecular Probes). Recombinant SHP-1 protein (25 ng) was incubated with either SC-43 or SC-40 at the indicated dose for 30 minutes and then analyzed by SHP-1 phosphatase activity. FIG. 20 shows that the SC derivatives increase phosphatase activity of SHP-1 in vitro, (A)SC-43 and (B)SC-40.

2.2.17 In Vivo Effect of SC-40 on PLC5-Bearing Xenograft.

Male NCr athymic nude mice (5-7 weeks of age) were obtained from the National Laboratory Animal Center (Taipei, Taiwan). All experimental procedures using these mice were done in accordance with protocols approved by the Institutional Laboratory Animal Care and Use Committee of National Taiwan University. Each mouse was inoculated s.c. in the dorsal flank with 1×106 PLC5 cells suspended in 0.1 mL of serum-free medium containing 50% Matrigel (BD Biosciences). When tumors reached 100 to 200 mm3, mice received SC-40 tosylate (10 or 20 mg/kg) orally once daily. Tumors were measured weekly using calipers, and their volumes were calculated using the following standard formula: width×length×height×0.52.

Figure 21:
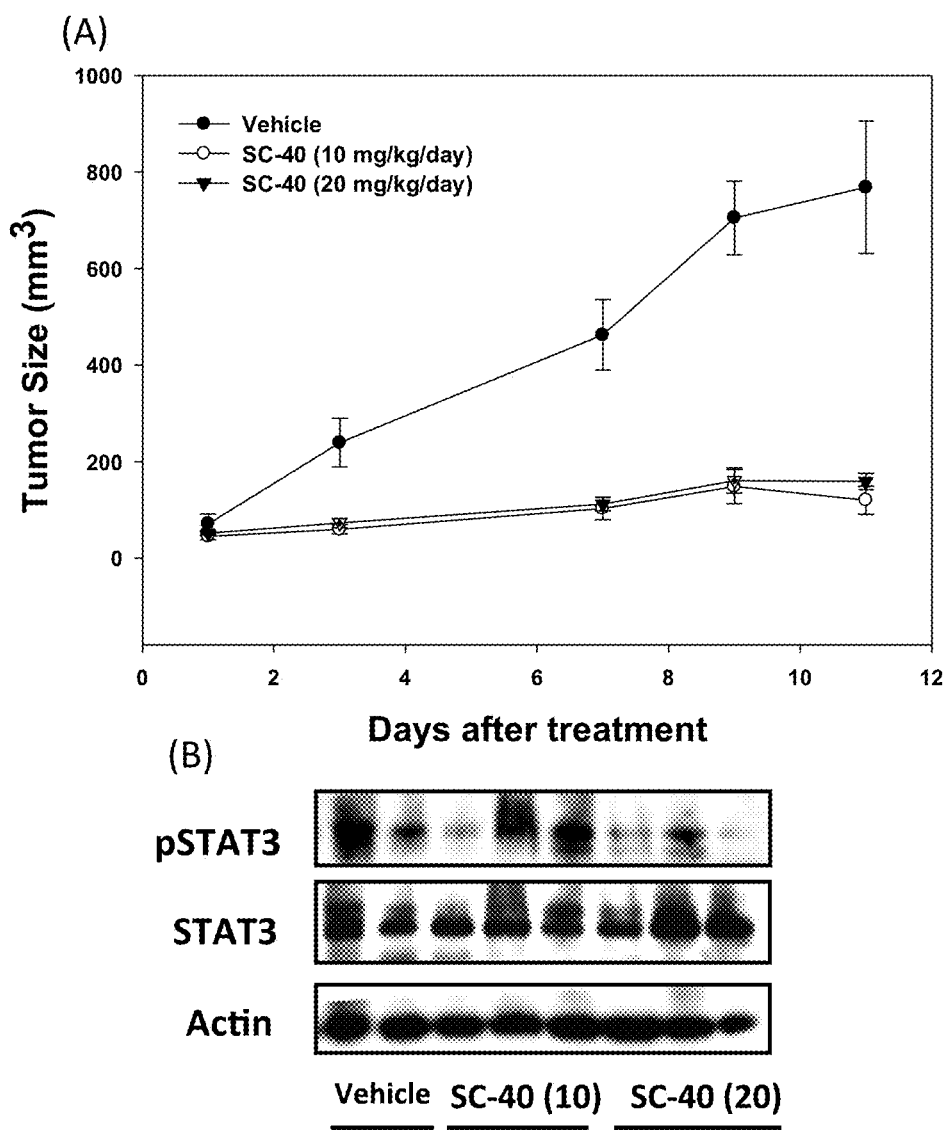
FIG. 21 shows that (A) the antitumor effect of SC-40 on PLC5 tumors; (B) Western blot analysis of p-STAT3 and STAT3 in PLC5 tumors; (C) the body weight of the animals; and (D) the tumor weight and (E) activity of SHP-1 in PLC5 tumors. Points, mean (n=6); bars, SE
Figure 21:
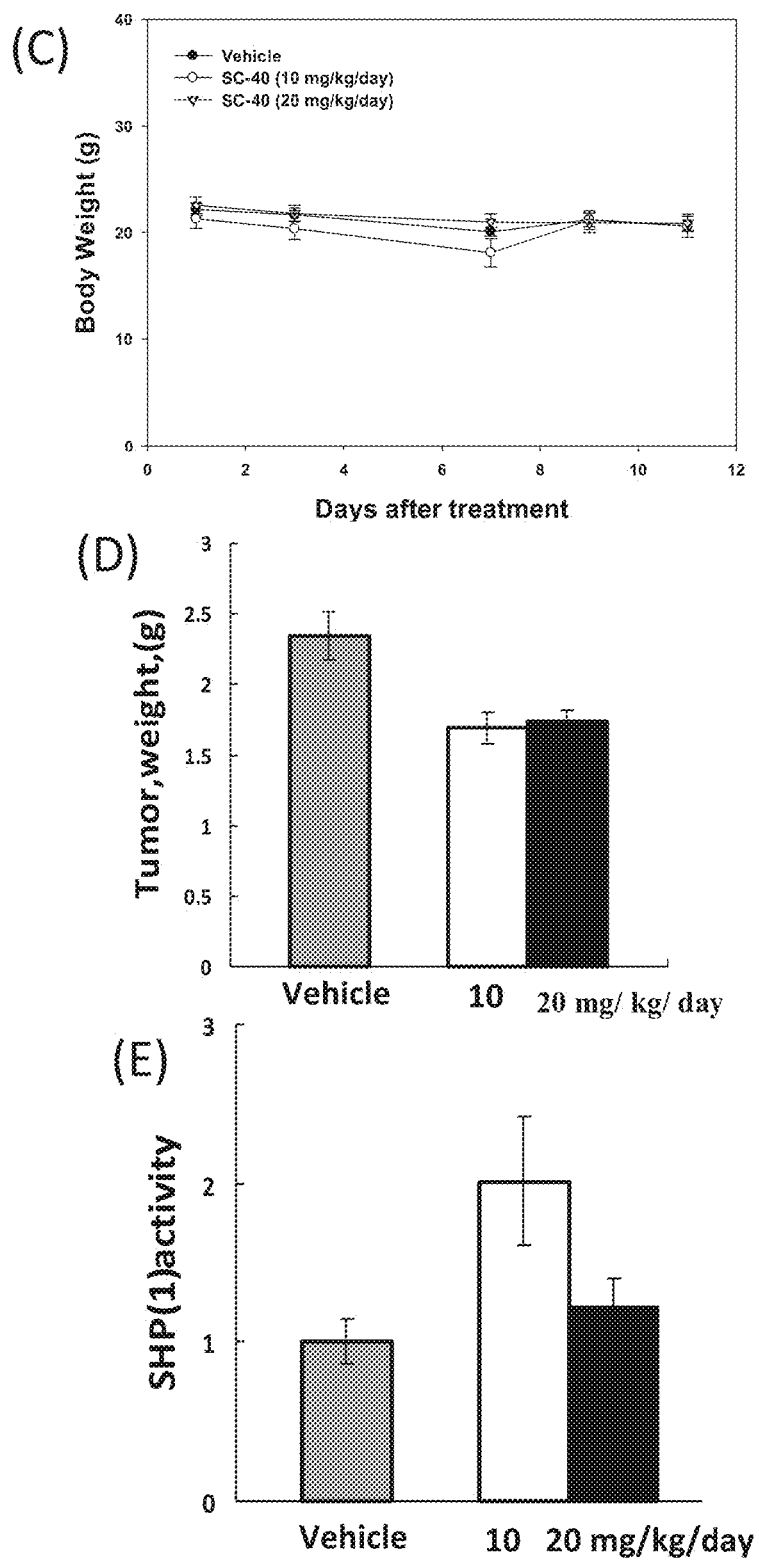

FIG. 21 shows that (A) the antitumor effect of SC-40 on PLC5 tumors; points, mean (n=6); bars, SE; (B) Western blot analysis of p-STAT3 and STAT3 in PLC5 tumors; (C) the body weight of the animals; and (D) tumor weight and (E) activity of SHP-1 in PLC5 tumors. The results show that SC-40 has significant anti-tumor effect on PLC5 tumors, but do not affect body weight of the animals. The body weight has no significant differences between control and SC-40-treated mice.

2.2.18 Antitumor Effect of SC-43

Figure 22:
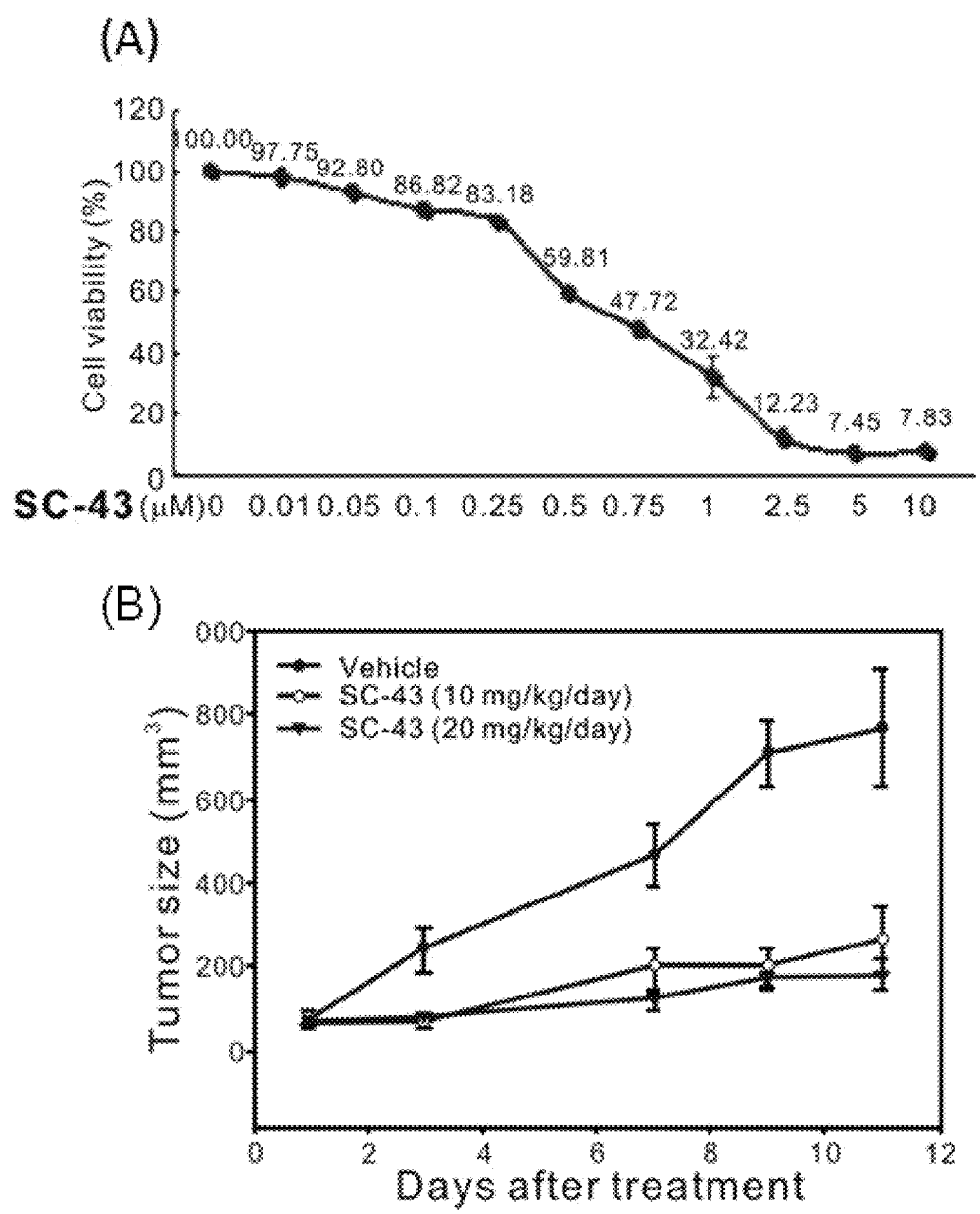
FIG. 22 shows that SC-43 exhibits antitumor effect in vitro and in vivo, (A) the cytotoxicity of SC-43 in HCC cells, (B) the antitumor effect of SC-43 in HCC-bearing mice, (C) the activity of SHP-1 induced by SC-43, and (D) Western blot analysis of p-STAT3 and STAT3 in HCC cells treated by SC-43 (10 μM and 20 μM).
Figure 22:
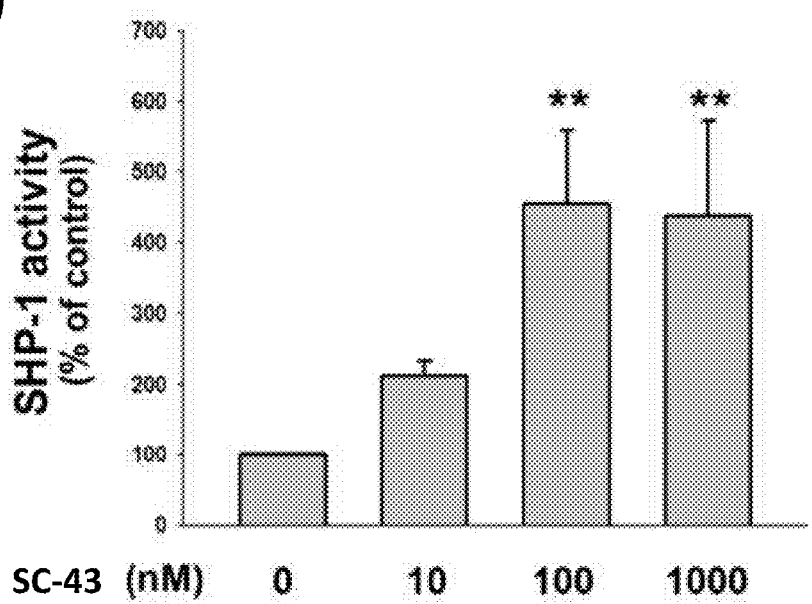
Figure 22:

In this example, we show that SC-43 exhibits antitumor effect in vitro and in vivo. SC-43 shows a significant cytotoxicity in HCC cells (IC50~0.5 µM). Also, SC-43 significantly causes tumor growth inhibition in HCC-bearing mice. SHP-1/STAT3-related signaling pathway acts as a vital target for the anti-tumor effect of SC-43. See FIG. 22 (A) the cytotoxicity of SC-43 in HCC cells, (B) the antitumor effect of SC-43 in HCC-bearing mice, (C) the activity of SHP-1 induced by SC-43, and (D) Western blot analysis of p-STAT3 and STAT3 in HCC cells treated by SC-43 (10 µM and 20 µM).

2.2.19 In Vivo Effect of SC-43 on PLC5/Luc Orthotopic Model

Male NCr athymic nude mice (5-7 weeks of age) were obtained from the National Laboratory Animal Center (Taipei, Taiwan). All experimental procedures using these mice were done in accordance with protocols approved by the Institutional Laboratory Animal Care and Use Committee of National Taiwan University. Each mouse was inoculated within liver in the dorsal flank with 1×104 PLC5/luc cells suspended in 0.1 mL of serum-free medium containing 50% Matrigel (BD Biosciences). When tumors formed, mice received sorafenib or SC-43 tosylate (10 mg/kg) orally once daily. Tumor growth was monitored by non-invasive in vivo imaging system (IVIS) image system twice weekly.

Figure 23:
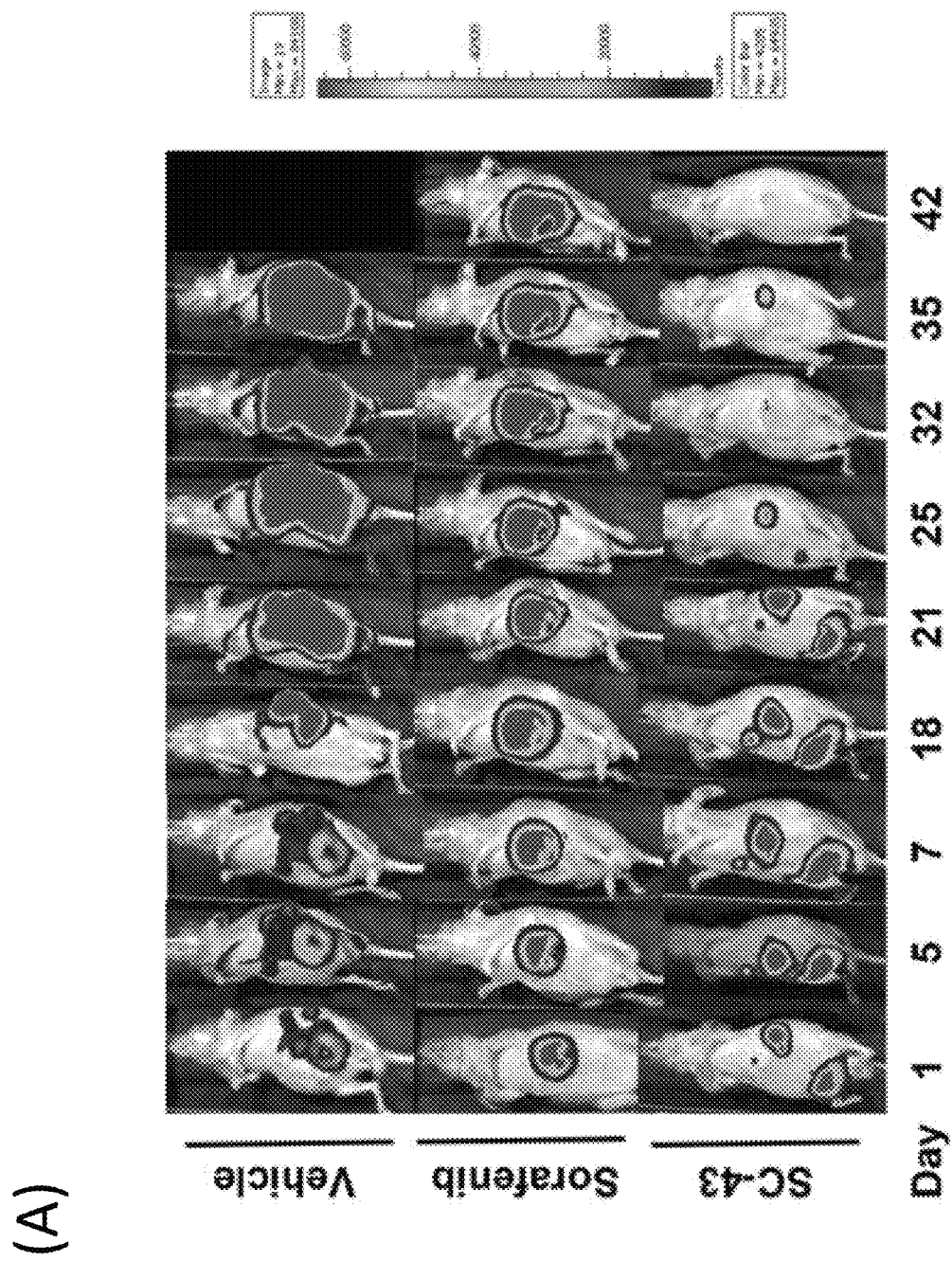
FIG. 23 shows (A) the image obtained by the non-invasive in vivo imaging system of the treated mice, (B) shows the body weight of the mice, and (C) shows the survival curve between control and treated mice.
Figure 23:
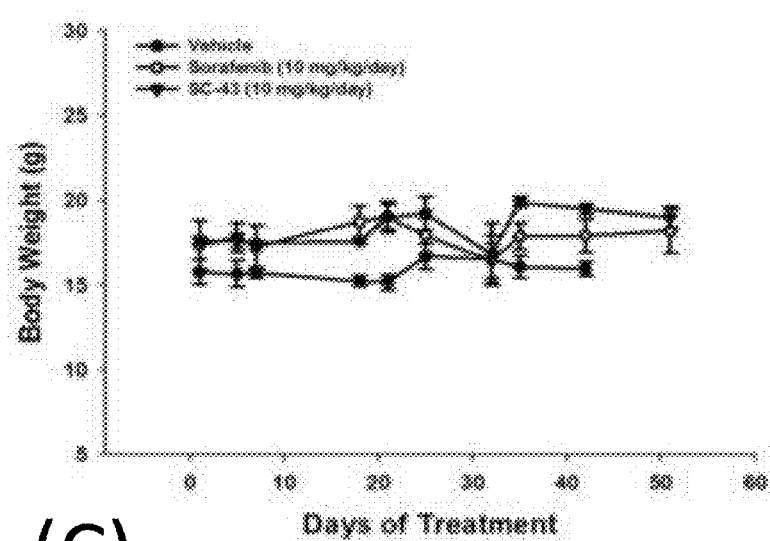
Figure 23:
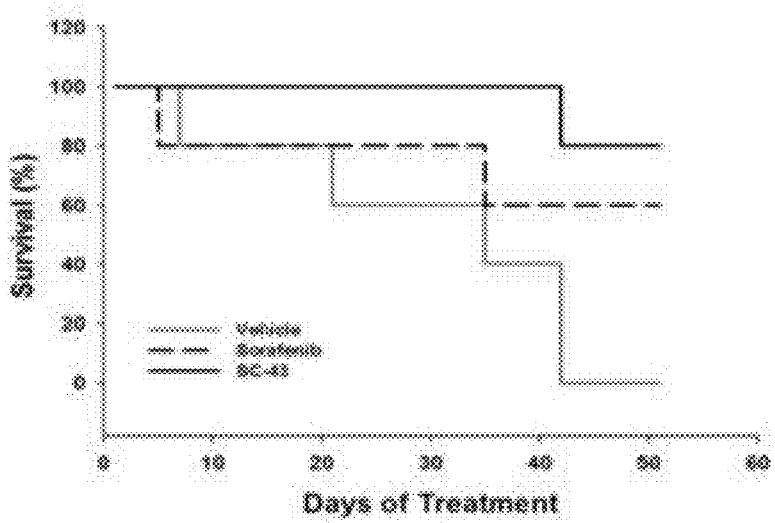

SC-40 shows a significant antitumor effect on PLC5-bearing orthotopic mice. The tumor growth was monitored at the indicated time by IVIS image system. Mice were treated with either vehicle, sorafenib (10 mg/kg) or SC-43 (10 mg/kg). FIG. 23 shows (A) the images of the treated mice, (B) shows the body weight of the mice, and (C) shows the survival curve between control and treated mice. The results show that SC-40 shows a significant antitumor effect on PLC5-bearing orthotopic mice. The body weight has no significant differences between control and SC-43-treated mice.

What is claimed is:

1. A compound which is represented by Formula II(b) or II(c)

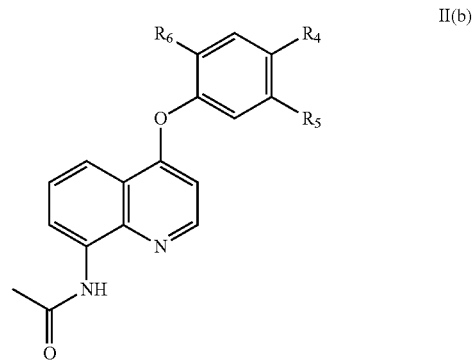

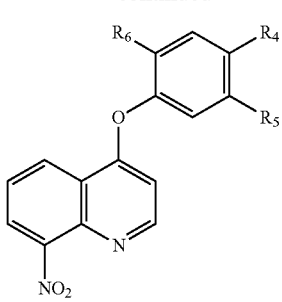

wherein R$_4$, R$_5$ and R$_6$ are independently hydrogen, hydroxyl, optionally substituted alkoxyl, optionally substituted thioalkoxy, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl, —(C)$_q$NHS(O)$_2$R$_c$, or —(C)$_r$(X)NHR$_d$;

wherein at least one R$_4$, R$_5$, or R$_6$ is not hydrogen;

wherein R$_c$, and R$_d$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl;

X=O or S; and q, r=0, 1, or 2.

2. The compound of claim 1, wherein R$_4$, R$_5$ and R$_6$ are independently hydrogen, or —(C)$_q$NHS(O)$_2$R$_c$.

3. The compound of claim 1 or 2, wherein R$_c$, and R$_d$ are independently phenyl or naphthyl, optionally substituted with 1 to 3 groups selected from the group consisting of halo, optionally substituted lower alkyl, optionally substituted alkoxyl and optionally substituted aryloxy.

4. A compound which is represented by Formula III

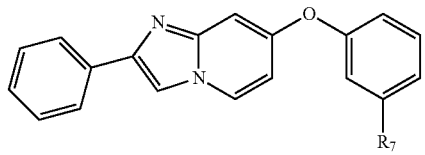

wherein R$_7$ is hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl, —(C)$_m$NHC(X)NH(C)$_n$R$_a$—, —(C)$_p$NHC(X)R$_b$—, —(C)$_q$NHS(O)$_2$R$_c$, —(C)$_r$(X)NHR$_d$, or —(C)$_s$NH(C)$_t$R$_e$;

wherein R$_a$, R$_b$, R$_c$, R$_d$ and R$_e$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl;

X=O or S; and m, n, p, q, r, s, t=0, 1, or 2.

5. The compound of claim 4, wherein R$_7$ is independently hydrogen, optionally substituted lower alkyl, —(C)$_m$NHC(X)NH(C)$_n$R$_a$—, —(C)$_p$NHC(X)R$_b$—, —(C)$_q$NHS(O)$_2$R$_c$, or —(C)$_s$NH(C)$_t$R$_e$.

6. The compound of claim 4 or 5, wherein R$_a$, R$_b$, R$_c$, R$_d$ and R$_e$ are independently phenyl or naphthyl, optionally substituted with 1 to 3 groups selected from the group consisting of halo, optionally substituted lower alkyl, optionally substituted alkoxyl and optionally substituted aryloxy.

7. The compound of claim 4, which is one of the compounds

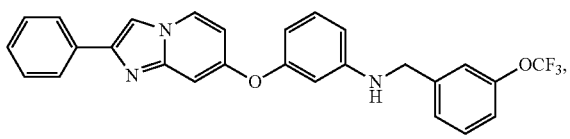

SC-36

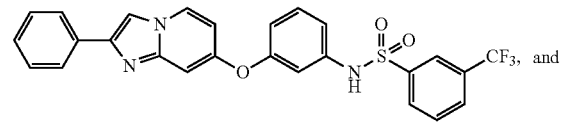

SC-37

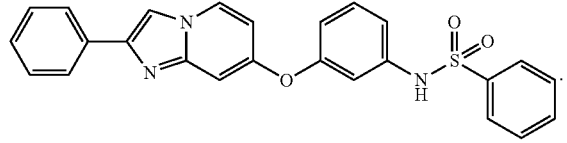

SC-38

8. A pharmaceutical composition comprising a compound as defined in claim 1 or 4 and a pharmacological acceptable carrier.

9. A pharmaceutical composition for increasing Src homology-2 containing protein tyrosine phosphatase-1 (SHP-1) expression in a cell, comprising a compound as defined in claim 1 or 4 and a pharmacological acceptable carrier.

10. A pharmaceutical composition for treating a disease or condition characterized by decreased Src homology-2 containing protein tyrosine phosphatase-1 (SHP-1), comprising a compound as defined in claim 1 or 4 and a pharmacological acceptable carrier, wherein the disease or condition characterized by decreased SHP-1 expression is cancer or osteoporosis.

11. A method for increasing Src homology-2 containing protein tyrosine phosphatase-1 (SHP-1) expression in a cell, comprising contacting the cell with an effective amount of a compound as defined in claim 1 or 4 or a pharmaceutical composition of claim 8.

12. A method for treating a disease or condition characterized by decreased Src homology-2 containing protein tyrosine phosphatase-1 (SHP-1) expression in a subject in need thereof, comprising administering to the subject an effective amount of a compound as defined in claim 1 or 4 or a pharmaceutical composition of claim 8, wherein the disease or condition characterized by decreased SHP-1 expression is cancer and osteoporosis.

13. The method of claim 12, wherein the cancer is hepatocellular carcinoma, leukemia, lung cancer, breast cancer, renal cancer, thyroid cancer colon, head and neck cancer.

14. A method of manufacturing a medicament including a compound as defined in claim 1 or 4 for treating a disease or condition characterized by decreased Src homology-2 containing protein tyrosine phosphatase-1 (SHP-1) expression, wherein the disease or condition characterized by decreased SHP-1 expression is cancer or osteoporosis.

15. The method of claim 14, wherein the cancer is hepatocellular carcinoma, leukemia, lung cancer, breast cancer, renal cancer, thyroid cancer colon, head and neck cancer.

* * * * *